United States Patent
Cai et al.

(10) Patent No.: US 11,267,802 B2
(45) Date of Patent: Mar. 8, 2022

(54) 2,4-BIS(NITROGEN-CONTAINING GROUP)-SUBSTITUTED PYRIMIDINE COMPOUND, PREPARATION METHOD AND USE THEREOF

(71) Applicant: BEBETTER MED INC., Guangdong (CN)

(72) Inventors: Xiong Cai, Guangdong (CN); Changgeng Qian, Guangdong (CN); Yunwo Weng, Guangdong (CN); Bin Liu, Guangdong (CN); Yanyan Wang, Guangdong (CN); Mingsheng Lin, Guangdong (CN); Junqi Li, Guangdong (CN); Yuanhui Qing, Guangdong (CN); Huajin You, Guangdong (CN); Shiqing Zhou, Guangdong (CN); Weicai Xue, Guangdong (CN)

(73) Assignee: BEBETTER MED INC., Guangdong (CN)

( * ) Notice: Subject to any disclaimer, the term of this patent is extended or adjusted under 35 U.S.C. 154(b) by 624 days.

(21) Appl. No.: 15/755,572

(22) PCT Filed: Jul. 26, 2016

(86) PCT No.: PCT/CN2016/091755
§ 371 (c)(1),
(2) Date: Feb. 27, 2018

(87) PCT Pub. No.: WO2017/036263
PCT Pub. Date: Mar. 9, 2017

(65) Prior Publication Data
US 2020/0165227 A1    May 28, 2020
US 2020/0331891 A9    Oct. 22, 2020

(30) Foreign Application Priority Data

Aug. 31, 2015  (CN) .......................... 201510552982.X
Jun. 22, 2016  (CN) .......................... 201610471043.7

(51) Int. Cl.
    C07D 471/04    (2006.01)
    C07D 403/04    (2006.01)
    A61P 35/00     (2006.01)
    C07D 401/14    (2006.01)
    C07D 403/14    (2006.01)
    C07D 413/14    (2006.01)

(52) U.S. Cl.
    CPC ............ C07D 403/04 (2013.01); A61P 35/00 (2018.01); C07D 401/14 (2013.01); C07D 403/14 (2013.01); C07D 413/14 (2013.01); C07D 471/04 (2013.01)

(58) Field of Classification Search
    CPC .................................................. C07D 471/04
    See application file for complete search history.

(56) References Cited

FOREIGN PATENT DOCUMENTS

| CN | 104761544 | 7/2015 |
|----|-----------|--------|
| CN | 104761585 | 7/2015 |
| CN | 105001208 | 10/2015 |
| CN | 105085489 | 11/2015 |
| EP | 3205650   | 8/2017 |
| EP | 3216786   | 9/2017 |
| EP | 3398939   | 11/2018 |
| WO | 2009158571 | 12/2009 |
| WO | 2013014448 | 1/2013 |
| WO | 2015188777 | 12/2015 |

(Continued)

OTHER PUBLICATIONS

Amit Kumar et al., "The Structure and Clinical Relevance of the EGF Receptor in Human Cancer", J Clin Oncol, Apr. 1, 2008, pp. 1742-1751.

(Continued)

*Primary Examiner* — Brian E McDowell
(74) *Attorney, Agent, or Firm* — JCIPRNET

(57) ABSTRACT

Provided are a 2, 4-di-(nitrogen containing group) substituted pyrimidine compound represented by a general formula (I), a pharmaceutically acceptable salt and a stereoisomer thereof, a preparation method thereof, and a use thereof in preparation of anti-tumor drugs. The compound having a structural feature shown in the general formula (I) can selectively suppress activity of mutant epidermal growth factor receptors (EGFR), including single-mutant EGFR (T790M) and double-mutant EGFR (including L858R/T790M and ex19del/T790M), and can suppress activity of single gain-of-function mutant EGFR (including L858R and ex19del) as well. The compound has a weak suppression effect on wild-type EFGR and a very high selectivity, and thus it has a potential to be used in preparation of drugs for treating EGFR mutant tumors, especially non-small cell lung cancer (NSCLC) comprising a T790M EGFR mutation.

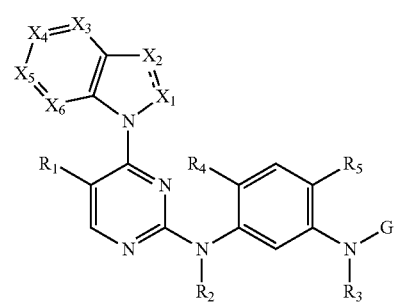

8 Claims, 3 Drawing Sheets

(56) References Cited

FOREIGN PATENT DOCUMENTS

| WO | 2015195228 | 12/2015 |
|---|---|---|
| WO | 2016029839 | 3/2016 |
| WO | 2016054987 | 4/2016 |
| WO | 2016105525 | 6/2016 |
| WO | 2017120429 | 7/2017 |

OTHER PUBLICATIONS

David M. Jackman et al., "Exon 19 Deletion Mutations of Epidermal Growth Factor Receptor Are Associated with Prolonged Survival in Non-Small Cell Lung Cancer Patients Treated with Gefitinib or Erlotinib", Clin Cancer Res, Jul. 1, 2006, pp. 3908-3914.

William Pao and Juliann Chmielecki, "Rational, biologically based treatment of EGFR-mutant non-small-cell lung cancer", Nat Rev Cancer, Nov. 2010, pp. 760-774.

Af Gazdar, "Activating and resistance mutations of EGFR in non-small-cell lung cancer: role in clinical response to EGFR tyrosine kinase inhibitors", Oncogene, Aug. 2009, pp. S24-S31.

Yohann Loriot et al., "Drug Insight: gastrointestinal and hepatic adverse effects of molecular-targeted agents in cancer therapy", Nature Clinical Practice Oncology, Mar. 18, 2008, pp. 268-278.

V. Hirsh, "Managing treatment-related adverse events associated with EGFR tyrosine kinase inhibitors in advanced non-small-cell lung cancer", Current Oncology, Jun. 2011, pp. 126-138.

Makoto Maemondo et al., "Gefitinib or Chemotherapy for Non-Small-Cell Lung Cancer with Mutated EGFR", The New England Journal of Medicine, Jun. 24, 2010, pp. 2380-2388.

Rafael Rosell et al., "Erlotinib versus standard chemotherapy as first-line treatment for European patients with advanced EGFR mutation-positive non-small-cell lung cancer (EURTAC): a multicentre, open-label, randomised phase 3 trial", Lancet Oncol, Jan. 26, 2012, pp. 239-246.

Susumu Kobayashi et al., "EGFR Mutation and Resistance of Non-Small-Cell Lung Cancer to Gefitinib", The New England Journal of Medicine, Feb. 24, 2005, pp. 786-792.

William Pao et al., "Acquired Resistance of Lung Adenocarcinomas to Gefitinib or Erlotinib Is Associated with a Second Mutation in the EGFR Kinase Domain", PLoS Medicine, Feb. 22, 2005, pp. 0225-0235.

Vincent A Miller et al., "Afatinib versus placebo for patients with advanced, metastatic non-small-cell lung cancer after failure of erlotinib, gefitinib, or both, and one or two lines of chemotherapy (LUX-Lung 1): a phase 2b/3 randomised trial", Lancet Oncol, Mar. 26, 2012, pp. 528-538.

Nobuyuki Katakami et al., "LUX-Lung 4: A Phase II Trial of Afatinib in Patients With Advanced Non-Small-Cell Lung Cancer Who Progressed During Prior Treatment With Erlotinib, Gefitinib, or Both", Journal of Clinical Oncology, Jul. 1, 2013, pp. 3335-3341.

M. Raymond V. Finlay et al., "Discovery of a Potent and Selective EGFR Inhibitor (AZD9291) of Both Sensitizing and T790M Resistance Mutations That Spares the Wild Type Form of the Receptor", Journal of Medicinal Chemistry, Oct. 1, 2014, pp. 8249-8267.

Darren A.E. Cross et al., "AZD9291, an Irreversible EGFR TKI, Overcomes T790M-Mediated Resistance to EGFR Inhibitors in Lung Cancer", Cancer Discovery, Jun. 3, 2014, pp. 1046-1061.

Annette O. Walter et al., "Discovery of a Mutant-Selective Covalent Inhibitor of EGFR that Overcomes T790MMediated Resistance in NSCLC", Cancer Discovery, Sep. 24, 2013, pp. 1404-1415.

Robert Tjin Tham Sjin et al., "In Vitro and In Vivo Characterization of Irreversible Mutant-Selective EGFR Inhibitors That Are Wild-Type Sparing", Molecular Cancer Therapeutics, Apr. 10, 2014, pp. 1468-1479.

Pasi A. Janne et al., "AZD9291 in EGFR Inhibitor-Resistant Non-Small-Cell Lung Cancer", The New England Journal of Medicine, Apr. 30, 2015, pp. 1689-1699.

Amy Card et al., "High-Throughput Biochemical Kinase Selectivity Assays: Panel Development and Screening Applications", Journal of Biomolecular Screening, Dec. 2008, pp. 31-42.

Promega Corporation, "CellTiter-Glo® Luminescent Cell Viability Assay," Technical Bulletin, Mar. 2015, pp. 1-14.

"Office Action of Canada Counterpart Application," dated Feb. 26, 2019, p. 1-p. 3.

"Search Report of Europe Counterpart Application", dated Mar. 8, 2019, p. 1-p. 9.

"Office Action of Australia Counterpart Application," dated Oct. 22, 2018, p. 1-p. 3.

"Office Action of Australia Counterpart Application," dated Feb. 1, 2019, p. 1-p. 6.

"Written Opinion of the International Searching Authority (Form PCT/ISA/237) of PCT/CN2016/091755," dated Oct. 26, 2016, with English translation thereof, pp. 1-14.

2,4-BIS(NITROGEN-CONTAINING GROUP)-SUBSTITUTED PYRIMIDINE COMPOUND, PREPARATION METHOD AND USE THEREOF

CROSS-REFERENCE TO RELATED APPLICATION

This application is a 371 of international application of PCT application serial no. PCT/CN2016/091755, filed on Jul. 26, 2016, which claims the priority benefit of China application no. 201510552982.X, filed on Aug. 31, 2015, and China application no. 201610471043.7, filed on Jun. 22, 2016. The entirety of each of the above-mentioned patent applications is hereby incorporated by reference herein and made a part of this specification.

BACKGROUND OF THE INVENTION

1. Field of the Invention

The present disclosure relates to the technical field of pharmaceutical chemistry, and especially relates to a 2,4-bis(nitrogen-containing group)-substituted pyrimidine compound and a preparation method and use thereof.

2. Description of Related Art

The epidermal growth factor receptor (EGFR) family of receptor tyrosine kinases (TKs) includes EGFR (HER1), HER2 (ErbB2), HER3 (ErbB3) and HER4 (ErbB4) that participate in regulation of many developmental, metabolic and physiological processes. The activation of EGFR receptor induces phosphorylation of the intracellular domain of EGFR and thus leads to activation of the Ras/mitogen-activated protein kinase signal pathways, the PI3K/AKT pathways, signal transduction pathways of signal transduction and transcription activation factors (J ClinOncol 2008; 26:1742-1751).

The mutation of EGFR genes and increased expression of EGFR proteins in tumor cells lead to EGFR TK activation, facilitating the survival, proliferation, invasion and metastasis of tumor cells. The epidermal growth factor receptor tyrosine kinase inhibitors (TKIs), such as Erlotinib, Gefitinib and Icotinib are reversible competitive inhibitors which can bind competitively to a receptor Adenosine triphosphate (ATP) binding site of a tyrosine kinase domain. Those drugs have significant curative effects for patents of non-small-cell lung cancer (NSCLC) with EGFR gene activating mutation. The sequence analysis of EGFR genes indicated that 90% of EGFR activating mutations are deletions of exon 19 and L858R mutation of exon 21 (J ClinOncol 2008; 26:1742-1751). There is a response rate of approximately 70% to Erlotinib and Gefitinib in NSCLC patients with EGFR activating mutations (Clin Cancer Res 2006; 12:3908-3914). The percentage of NSCLC with EGFR activating mutations is 10-15% in westerners and 30-40% in Asians (Nat Rev Cancer 2010; 10:760-774; Oncogene 2009; 28 (Suppl 1): S24-S31.). The first generation of reversible and competitive EGFR inhibitors which may cause side effects such as rash and diarrhea due to their simultaneous inhibition of skin and gastrointestinal wild-type EGFR (Nat Clin Pract Oncol 2008; 5:268-278; CurrOncol 2011; 18: 126-138).

The NSCLC patients with EGFR activating mutations, after being administrated with Gefitinib, Erlotinib or Icotinib for 6-14 months, had worsened conditions (N Engl J Med 2010; 362:2380-2388; Lancet Oncol 2012; 13:239-246). 50%-60% of acquired drug-resistant patients had drug resistance mutation at T790M (the second point mutation). The amino acid at position 790 in exon 20 of the wild-type EGFR gene is threonine (T), while the T790M mutation is caused by substitution of threonine (T) by a bulkier methionine (M), at position 790 in exon 20 of the EGFR gene. The T790M mutation changes the affinity of ATP and as a result, the first-generation EGFR-TKI (tyrosine kinases inhibitor) cannot inhibit the signal effectively, which leads to drug resistance (N Eng J Med 2005; 352:786-792; PLoS Med 2005; 2:e73; Oncogene 2009; 28 (Suppl 1): S24-S31.).

The second-generation EGFR inhibitors, such as Dacomitinib, Afatinib, Neratinib, XL647, and the like, are irreversible EGFR-TKIs, capable of non-specific inhibition of wild-type EGFR, L858R activating mutation and T790M drug resistance mutation. Although those compounds are active against EGFR T790M mutation, the drug resistance due to T790M mutation is an unsolved problem in the clinical stage (Lancet Oncol 2012; 13:528-538; J Clin Oncol 2013; 31:3335-3341). Besides, because they inhibit wild-type EGFR non-selectively, dose-limiting toxicity (DLT) is caused, preventing those drugs to reach effective inhibitory concentration of T790M in vivo.

The third-generation EGFR inhibitor can inhibit T790M resistance mutation selectively and has a minimal inhibitory effect on wild-type EGFR. Rociletinib (CO-1686), AZD9291, HM61713 and the like are all selective irreversible T790 EGFR inhibitors (J Med Chem 2014; 57:8249-8267; Cancer Discov 2014; 4:1046-1061; Cancer Discov 2013; 3:1404-1405; Mol Cancer Ther 2014; 13:1468-1479). Osimertinib (AZD9291) and Rociletinib (CO-1686) 1, when clinically administrated to EGFR-TKI drug resistant patients caused by T790M mutation, had shown good safety and anti-tumor activity (N Engl J Med. 2015; 372:1689-1699).

Because the third-generation EGFR inhibitors can inhibit EGFR mutation selectively with a minimal inhibitory effect on wild-type EGFR, they have shown strong anti-tumor activity in pre-clinical research with an obvious reduction of dose-limiting toxicity (DLT), such as rash and diarrhea toxic effects, compared with the first-generation and the second-generation EGFR inhibitors.

SUMMARY OF THE DISCLOSURE

In view of the above, it is necessary to provide a group of compounds, which can selectively inhibit T790M EGFR, including T790M single-point mutation and double-point mutation (such as L858R/T790M and ex19del/T790M) to address the above problem. Such compounds also have inhibitory activity on EGFR single-point activating mutation, such as L858R and ex19del, and have weak inhibitory effect on the wild-type EGFR. In other words, such compounds have good selectivity without causing the problem of DLT.

A 2,4-bis(nitrogen-containing group)-substituted pyrimidine compound of formula I or a pharmaceutically acceptable salt or a stereoisomer thereof is provided herein:

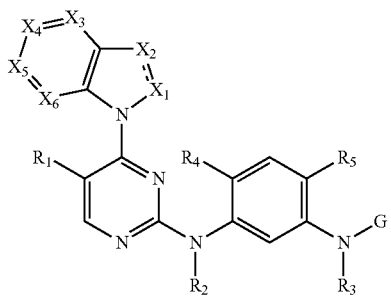

wherein the dash line between $X_1$ and $X_2$ refers to an optional single bond or double bond between $X_1$ and $X_2$;

$R_1$ is selected from the group consisting of H, C1-C6 alkyl, C3-C6 cycloalkyl, C3-C6 cycloalkyl-substituted methyl, halo-substituted C1-C4 alkyl, hydroxyl-substituted C1-C4 alkyl, C1-C3 alkoxy-substituted C1-C4 alkyl, amino-substituted C1-C4 alkyl, C1-C3 alkylamino-substituted C1-C4 alkyl, halogen, nitro, hydroxyl, C1-C6 alkoxy, C1-C6 alkylthio, C1-C6 sulfoxide, C1-C6 sulfone, cyano, amino, C1-C3 alkyl-substituted amino, ester, acyl, amido, and carboxyl;

$R_2$ and $R_3$ are each independently selected from the group consisting of H and C1-C6 alkyl;

$R_4$ is selected from the group consisting of H, OH, C1-C6 alkyl, C1-C6 alkoxy, hydroxyl-substituted C1-C4 alkyl, and C1-C3 alkoxy-substituted C1-C4 alkoxy;

$R_5$ is selected from the group consisting of the groups below:

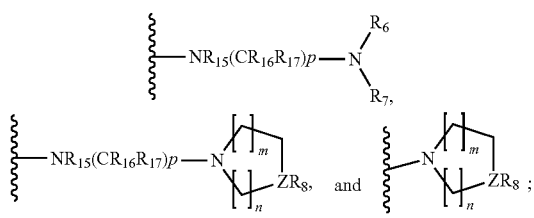

$R_{15}$ is selected from the group consisting of H and C1-C6 alkyl;

$R_{16}$ and $R_{17}$ are each independently selected from the group consisting of H, C1-C6 alkyl, and C1-C6 alkoxy;

Z is selected from the group consisting of C, N, and O, and when Z is O, $R_8$ does not exist;

m is selected from 0, 1, or 2;

n is selected from 1, 2, or 3;

p is selected from 1, 2, 3, 4, 5, or 6;

$R_6$, $R_7$, and $R_8$ are each independently selected from the group consisting of H, C1-C6 alkyl, C3-C6 cycloalkyl, C3-C6 cycloalkyl-substituted methyl, benzyl, phenyl, acyl, methylsulfonyl, halo-substituted C1-C4 alkyl, hydroxyl-substituted C1-C4 alkyl, C1-C3 alkoxy-substituted C1-C4 alkyl, amino-substituted C1-C4 alkyl, C1-C3 alkylamino-substituted C1-C4 alkyl, amino, C1-C3 alkyl-substituted amino, hydroxyl, and C1-C6 alkoxy;

$X_1$ is selected from the group consisting of N, C=O, and C—$R_9$;

$R_9$ is selected from the group consisting of H, C1-C6 alkyl, halo-substituted C1-C6 alkyl, C1-C6 alkyl containing O, N, or S heteroatoms, halogen, cyano, and amino;

$X_2$ is selected from the group consisting of N, N—$R_{10}$, and C—$R_{10}$;

$R_{10}$ is selected from the group consisting of H, halogen, C1-C6 alkyl, C2-C6 alkenyl, C2-C6 alkynyl, C3-C6 cycloalkyl, C3-C6 cycloalkyl methyl, halo-substituted C1-C6 alkyl, and C1-C6 alkyl containing O, N, or S heteroatoms;

$X_3$, $X_4$, $X_5$, and $X_6$ are each independently selected from the group consisting of N, and C—$R_{11}$;

$R_{11}$ is selected from the group consisting of H, C1-C6 alkyl, hydroxyl-substituted C1-C4 alkoxy, C1-C3 alkoxy-substituted C1-C4 alkoxy, C3-C6 cycloalkyl, C3-C6 cycloalkyl methyl, halo-substituted C1-C4 alkyl, hydroxyl-substituted C1-C4 alkyl, C1-C3 alkoxy-substituted C1-C4 alkyl; amino-substituted C1-C4 alkyl, C1-C3 alkylamino-substituted C1-C4 alkyl, halogen, nitro, hydroxyl, C1-C6 alkoxy, C1-C6 alkylthio, C1-C6 sulfoxide, C1-C6 sulfone, cyano, amino, C1-C3 alkyl-substituted amino, ester, acyl, amido, C1-C3 alkyl-substituted amido, and carboxyl;

G is selected from the group consisting of the following groups:

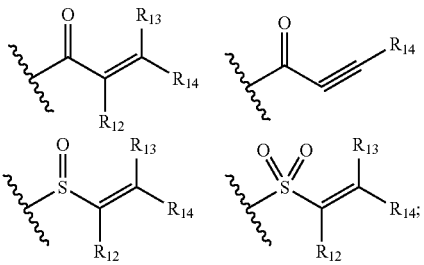

$R_{12}$ and $R_{13}$ are each independently selected from the group consisting of H and C1-C6 alkyl;

$R_{14}$ is selected from the group consisting of H, C1-C6 alkyl, C1-C3 alkoxy-substituted C1-C4 alkyl, amino-substituted C1-C4 alkyl; C1-C3 alkylamino-substituted C1-C4 alkyl, and heterocycle-substituted C1-C4 alkyl; and if $R_1$ is selected from the group consisting of H, halogen, and cyano, $R_4$ is C1-C6 alkoxy, G is

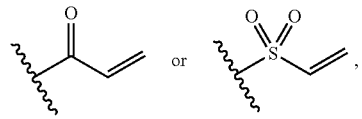

and $R_{10}$ is selected from the group consisting of H, C1-C6 alkyl, C3-C6 alkoxy, and halo-substituted C1-C6 alkyl, then $R_{11}$ is not selected from any one in the group consisting of H, C1-C6 alkyl, C3-C6 cycloalkyl, halo-substituted C1-C4 alkyl, o C1-C6 sulfone; or if $R_1$ is selected from the group consisting of H, halogen, and cyano, $R_4$ is C1-C6 alkoxy, G is

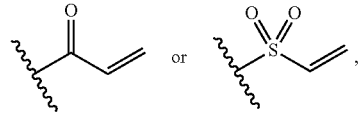

and $R_{11}$ is selected from the group consisting of H, C1-C6 alkyl, C3-C6 cycloalkyl, halo-substituted C1-C4 alkyl, and C1-C6 sulfone, then $R_{10}$ is not selected from any one in the group consisting of H, C1-C6 alkyl, C3-C6 cycloalkyl, and halogen-substituted C1-C6 alkyl.

In some embodiments, the compound disclosed herein is selected from the group consisting of compounds of formula II and formula III:

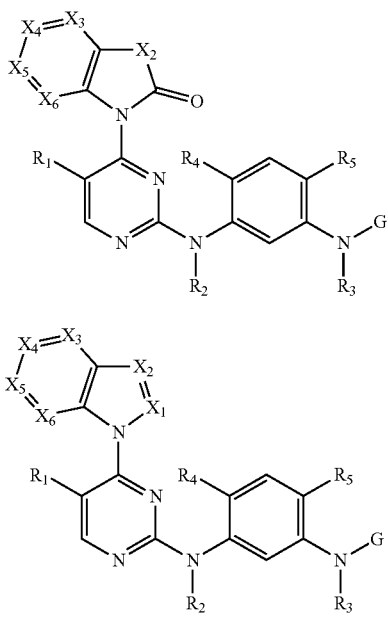

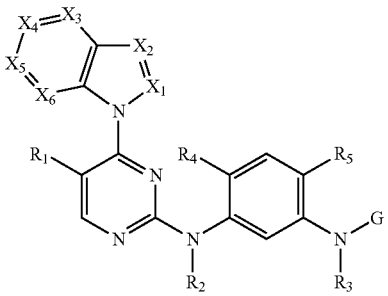

wherein $X_1$ is selected from the group consisting of N and C—$R_9$;

$X_2$, $X_3$, $X_4$, $X_5$, and $X_6$ are each as previously described; and $R_1$, $R_2$, $R_3$, $R_4$, $R_5$, $R_9$, and G are each defined as previously described.

In some embodiments, $X_3$, $X_5$, and $X_6$ are each independently selected from the group consisting of N and CH, $X_4$ is C—$R_{11}$, and $R_{11}$ is as previously described.

In some embodiments, the compound disclosed herein is selected from the group consisting of compounds of formula II below:

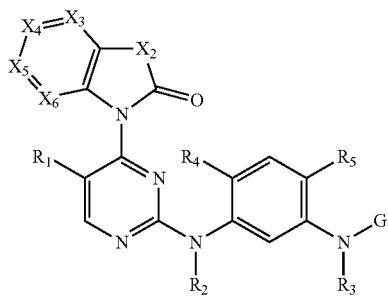

wherein $X_2$ is N—$R_{10}$;

$R_{10}$ is selected from the group consisting of C1-C6 alkyl, C2-C6 alkenyl, C3-C6 cycloalkyl, and C3-C6 cycloalkylmethyl;

$X_3$, $X_5$, and $X_6$ are each independently CH;

$X_4$ is C—$R_{11}$;

$R_{11}$ is selected from the group consisting of C1-C6 alkoxy, halogen, and cyano; and $R_1$, $R_2$, $R_3$, $R_4$, $R_5$, and G are each as previously described.

In some embodiments, the compound disclosed herein is selected from the group consisting of compounds of formula III

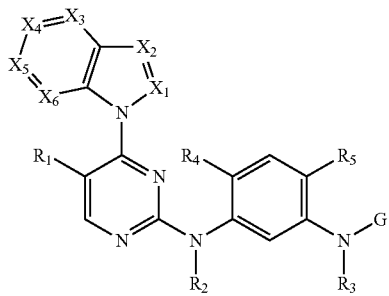

wherein $X_1$ and $X_2$ are each CH;

$X_3$ is N;

$X_4$ is as previously described;

$X_5$ and $X_6$ are each CH; and $R_1$, $R_2$, $R_3$, $R_4$, $R_5$, $R_9$, and G are each as previously described.

In some embodiments, $X_1$ and $X_2$ are each independently selected from the group consisting of C and N—$R_{10}$;

$R_{10}$ is selected from the group consisting of C1-C6 alkyl, C2-C6 alkenyl, C3-C6 cycloalkyl, and C3-C6 cycloalkylmethyl;

$X_3$ is selected from the group consisting of CH and N;

$X_5$, $X_6$ are each independently CH;

$X_4$ is C—$R_{11}$;

$R_{11}$ is selected from the group consisting of C1-C6 alkoxy, halogen, and cyano;

$R_1$, $R_2$, and $R_3$ are each H;

$R_4$ is a methoxy group;

$R_5$ is the group below:

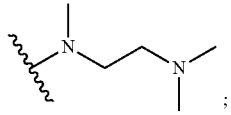 [SMILES: *N(C)CCN(C)C]

and

G is the group below:

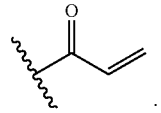 [SMILES: *C(=O)C=C]

In some embodiments, $R_1$ is selected from the group consisting of H, F, Cl, Br, methyl, trifluoromethyl, methoxy, cyano, hydroxyl, dimethylamino, and amido group;

$R_2$ and $R_3$ are each H;

$R_4$ is selected from the group consisting of H, methoxy, ethoxy, methyl, ethyl, OH, and methoxyethoxy;

$R_{12}$ and $R_{13}$ are each H;

$R_{14}$ is selected from the group consisting of H, C1-C6 alkyl, C1-C3 alkoxy-substituted C1-C4 alkyl, amino-substituted C1-C4 alkyl, C1-C3 alkylamino-substituted C1-C4 alkyl, and heterocycle-substituted C1-C4 alkyl.

In some embodiments, $R_5$ is selected from the group consisting of the groups below:

-continued

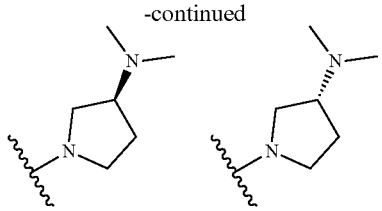

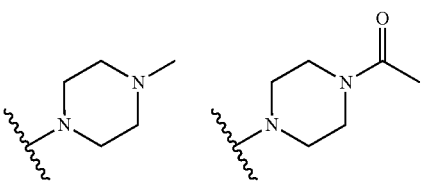

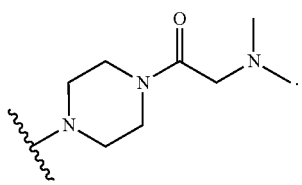

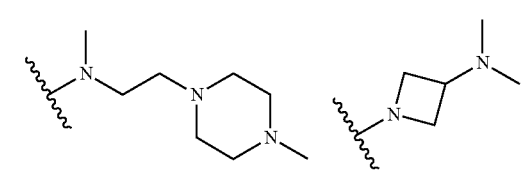

The present disclosure also discloses a preparation method of the 2,4-bis(nitrogen-containing group)-substituted pyrimidine compound as described above, the preparation method comprising the following steps:

reducing a nitro group of an intermediate 101 to obtain an intermediate 102; reacting the intermediate 102 with a nitrate in an acidic condition to obtain an intermediate 103; substituting an amino group of the intermediate 103 by bromo to obtain an intermediate 104, and then reacting the intermediate 104 with an intermediate which has an $R_5$ with N connected to H to obtain an intermediate 105 for later use; or, instead, reacting the intermediate 103 with an intermediate which has an $R_5$ with N connected to H to obtain an intermediate 106 for later use; wherein the reaction scheme is as shown below:

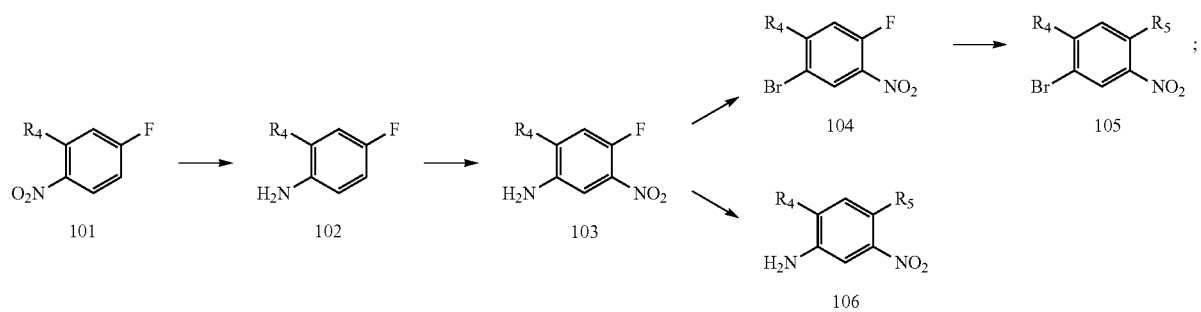

reacting an intermediate 201 with an intermediate 202, 203 or 301 to obtain an intermediate 204, 205, or 302, respectively; substituting a chloride of the intermediate 204 by ammonium hydroxide to obtain an intermediate 205; oxidizing a sulfur of the intermediate 302 to obtain an intermediate 303; reacting the intermediate 303 with ammonium hydroxide to obtain the intermediate 205 for later use; wherein the reaction scheme is as shown below:

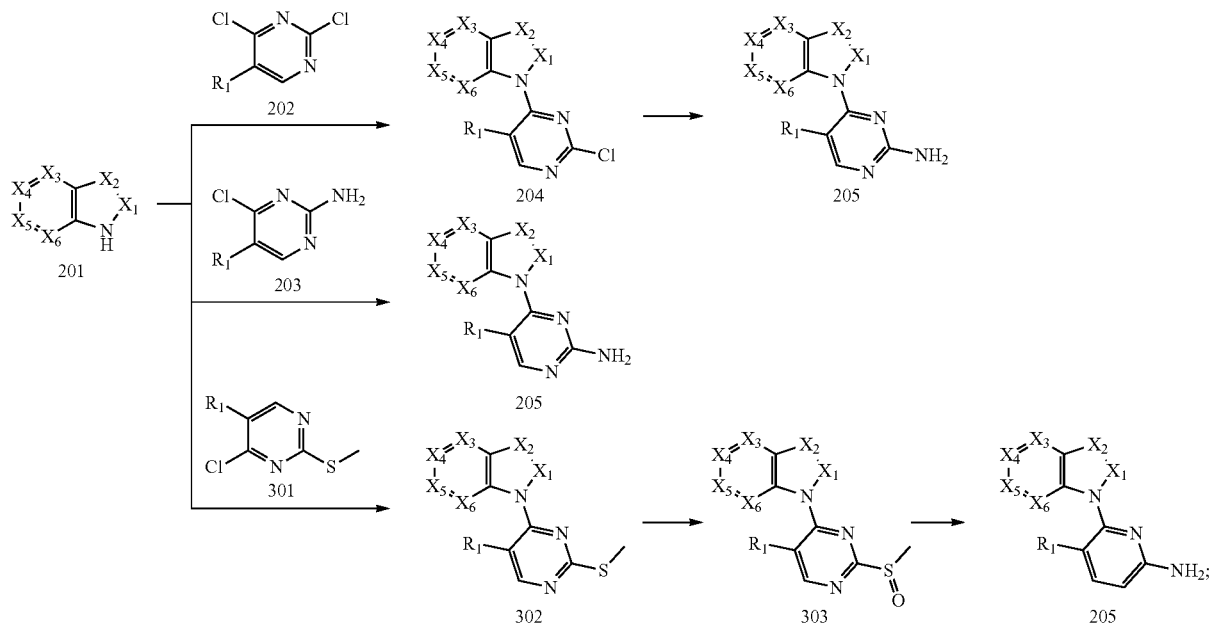

reacting an intermediate 201 with an intermediate 202, 203 or 301 to obtain an intermediate 204, 205, or 302, respectively; substituting a chloride of the intermediate 204 by ammonium hydroxide to obtain an intermediate 205; oxidizing a sulfur of the intermediate 302 to obtain an intermediate 303; reacting the intermediate 303 with ammonium hydroxide to obtain the intermediate 205 for later use; wherein the reaction scheme is as shown below:

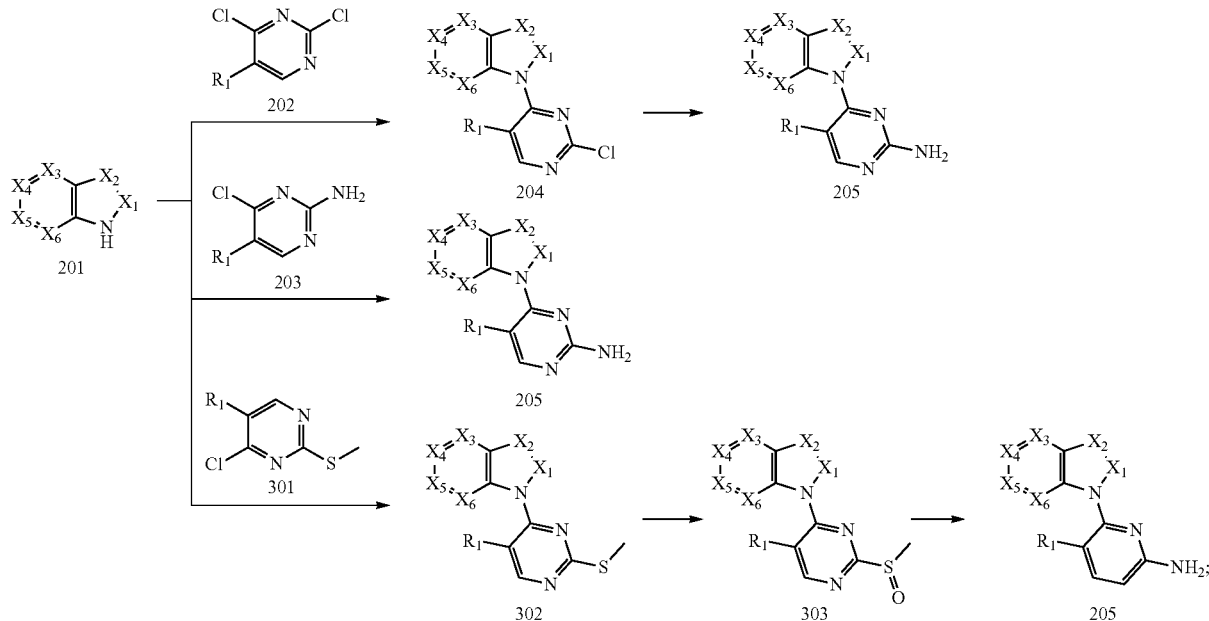

reacting the intermediate 403 with an intermediate containing a G group to obtain a target compound, wherein the reaction scheme is as shown below:

nitrate in an acidic condition to obtain an intermediate 103; substituting an amino group of the intermediate 103 by bromo to obtain an intermediate 104, and then reacting the

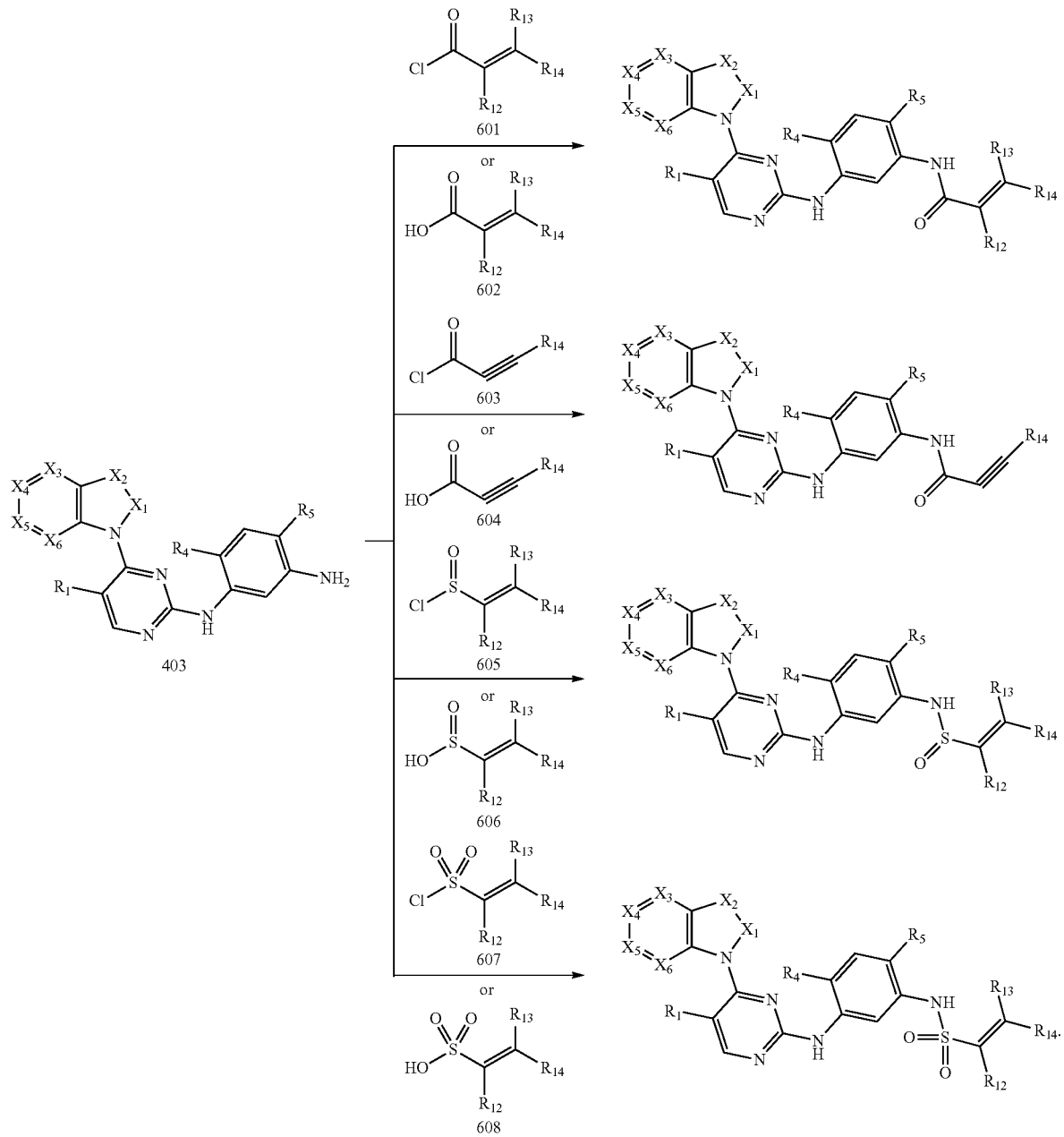

The present disclosure also discloses a preparation method of the aforementioned 2,4-bis(nitrogen-containing group)-substituted pyrimidine compound, the preparation method comprising the following steps:

reducing a nitro group of an intermediate 101 to obtain an intermediate 102; reacting the intermediate 102 with a intermediate 104 with an intermediate which has an $R_5$ with N connected to H to obtain an intermediate 105 for later use; or, instead, reacting the intermediate 103 with a compound which has an $R_5$ with N connected to H to obtain an intermediate 106 for later use; wherein reaction scheme is as shown below:

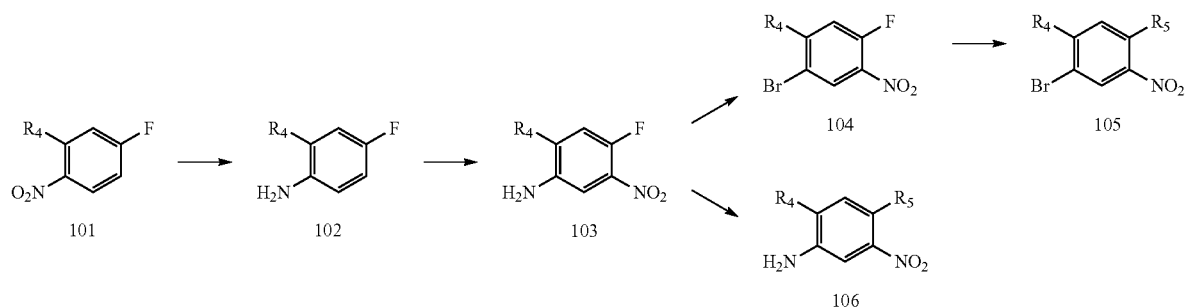

subjecting an intermediate 501 to a ring-closure reaction in presence of N,N'-carbonyl diimidazole (CDI) to produce an intermediate 502; reacting the intermediate 502 with the intermediate 202 to obtain an intermediate 503, then substituting a chloride of the intermediate 503 by amino of ammonium hydroxide to produce an intermediate 504, and reacting the intermediate 504 with the intermediate 105 to obtain an intermediate 505; or instead, reacting the intermediate 503 with the intermediate 106 to obtain an intermediate 505; or instead, reacting the intermediate 503 with the intermediate 103, and then reacting a fluro of the product thereof with the amino-containing $R_5$ to obtain the intermediate 505; and, reducing the nitro group of the intermediate 505 to obtain an intermediate 506 for later use; wherein the reaction scheme is as shown below:

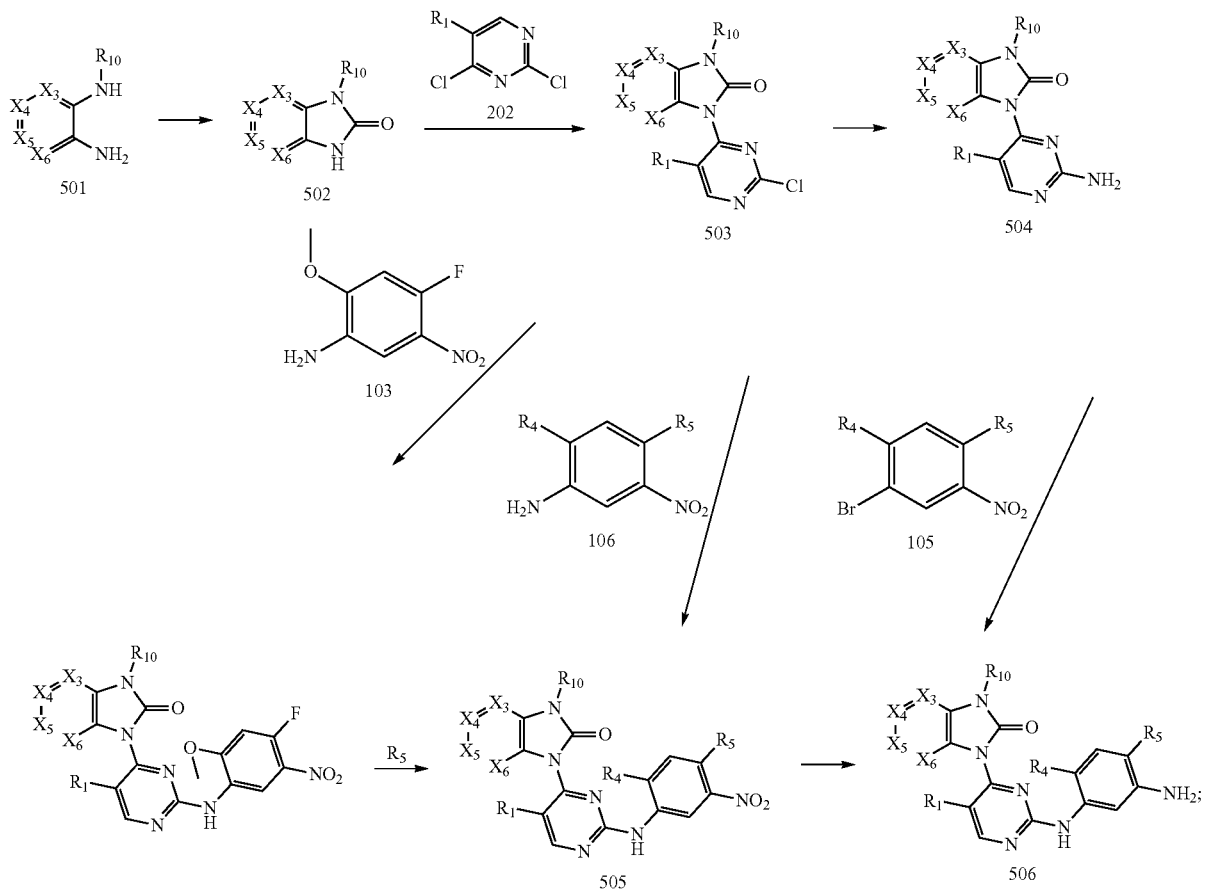

and
reacting the intermediate 506 with an intermediate containing a G group to obtain a target compound, wherein the reaction scheme is as shown below:

The present disclosure also discloses a pharmaceutical composition for treatment or prevention of a tumor, the pharmaceutical composition comprising the 2,4-bis(nitrogen-containing group)-substituted pyrimidine compound or

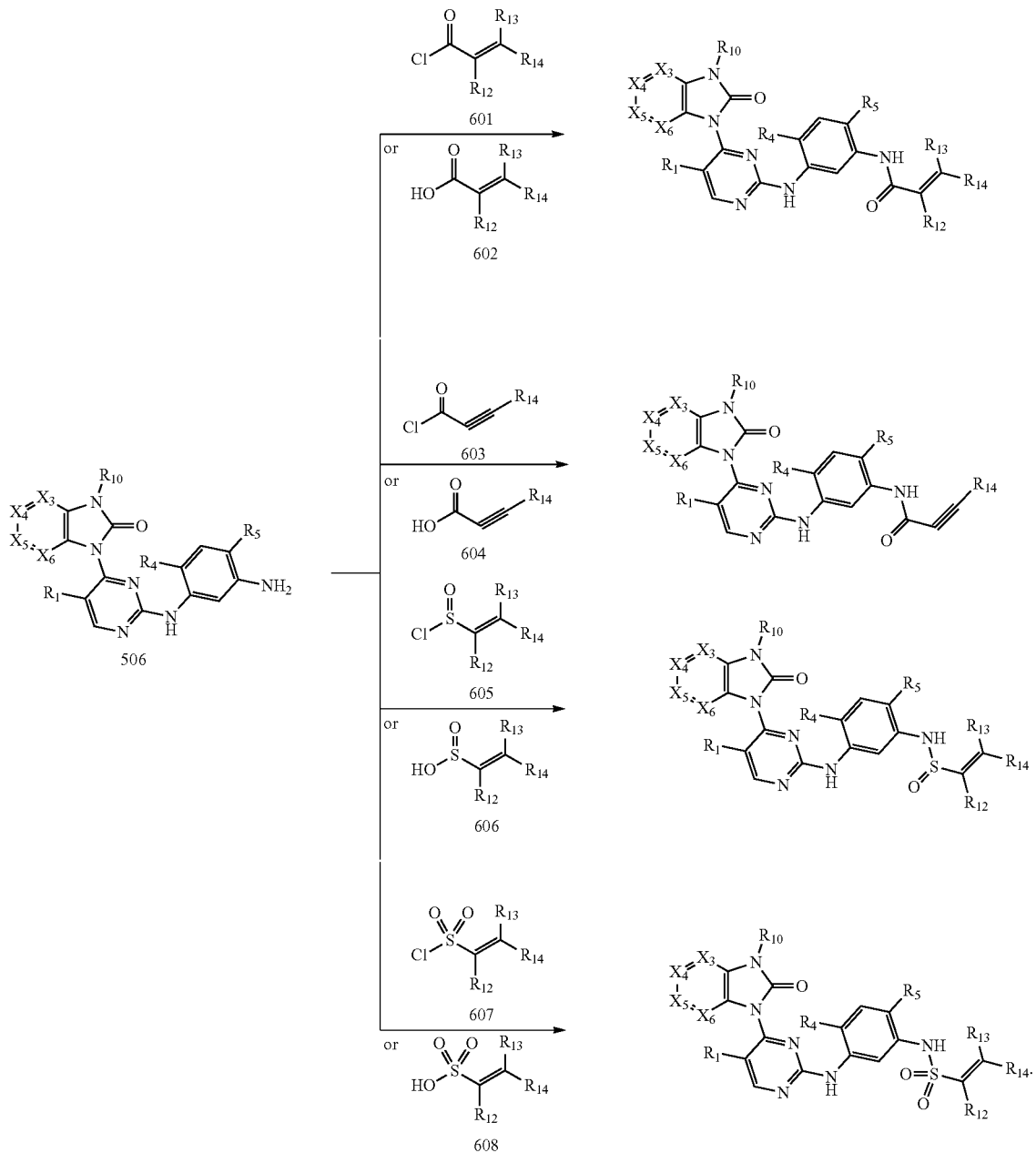

The present disclosure also discloses use of the aforementioned 2,4-bis(nitrogen-containing group)-substituted pyrimidine compound or a pharmaceutically acceptable salt or a stereoisomer thereof in preparation of medicaments for treatment or prevention of a tumor.

In some embodiments, the tumor is a solid tumor.

In some embodiments, the tumor is a malignant tumor with EGFR gene mutation.

In some embodiments, the tumor is non-small-cell lung cancer (NSCLC) with T790M EGFR mutation.

a pharmaceutically acceptable salt or a stereoisomer thereof as an active component, and a pharmaceutically acceptable carrier.

In some embodiments, the tumor is non-small-cell lung cancer (NSCLC) with T790M EGFR mutation.

Compared with the prior art, the present disclosure has following advantageous effects.

The present disclosure provides 2,4-bis(nitrogen-containing group)-substituted pyrimidine compounds which are a series of novel compounds that can selectively inhibit T790M EGFR, including T790M single-point mutation and double-point mutation (such as L858R/T790M and ex19del/ T790M). At the same time, such compounds also have inhibitory activity on EGFR single-point activating mutation, such as L858R and ex19del.

Furthermore, such compounds not only have strong antiproliferation activity on L858R/T790M EGFR mutation cells (such as H1975), but also have weak antiproliferation activity on wild-type EGFR cells (such as LOVO and H358), therefore providing high selectivity.

The 2,4-bis(nitrogen-containing group)-substituted pyrimidine compounds herein have the potential for use as medication to treat a malignant tumor with EGFR mutation, especially NSCLC with T790M EGFR mutation.

DETAILED DESCRIPTION OF EMBODIMENTS

Figure 1:
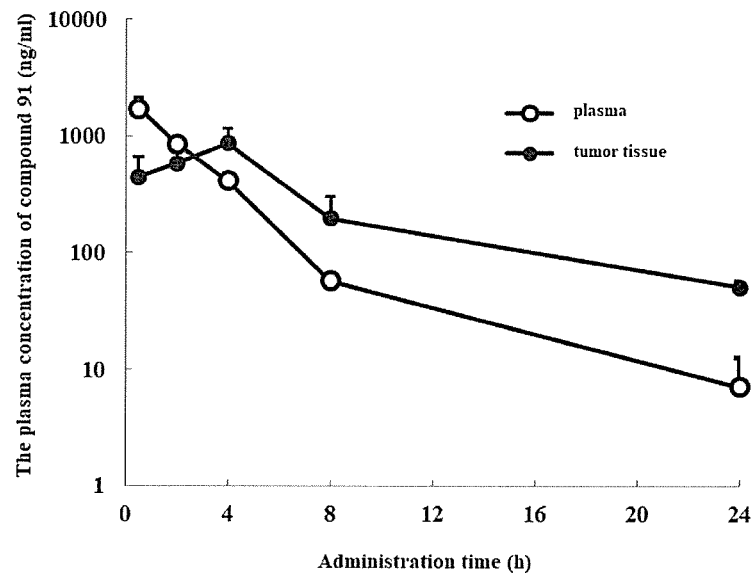
FIG. 1 shows a graph of the drug concentration in plasma and tumor tissues as a function of time after oral administration (30 mg/kg) of the compound 91 in the H1975 tumor xenograft mice, according to an Experimental Example.

The present disclosure will be further illustrated with reference to the specific examples and accompanying drawings, but should not be taken as limiting the disclosure in any way.

The term "alkyl", as used herein, refers to a linear or branched-chain saturated aliphatic hydrocarbon group having a specified number of carbon atoms. For example, the "C1-C6" as in "C1-C6 alkyl" is defined as the group comprising a linear or branched chain having 1, 2, 3, 4, 5, or 6 carbon atom(s). For example, "C1-C6 alkyl" specifically includes methyl, ethyl, propyl, isopropyl, n-butyl, tert-butyl, isobutyl, pentyl, and hexyl.

The term "cycloalkyl" refers to a monocyclic saturated aliphatic hydrocarbon group having a specified number of carbon atoms. For example, "cycloalkyl" includes cyclopropyl, methyl-cyclopropyl, 2,2-dimethyl-cyclobutyl, 2-ethyl-cyclopentyl, cyclohexyl, and the like.

The term "alkoxy" refers to a group with an alkyl directly connected to oxygen, such as methoxy, ethoxy and so on.

The term "alkylthio" refers to a group with an alky directly connected to sulfur.

The term "C1-C3 alkylamino-substituted C1-C4 alkyl" refers to a group with an alkyl containing 1, 2, or 3 carbon atom(s) connected with a nitrogen atom which in turn is connected with an alkyl containing 1, 2, 3, or 4 carbon atom(s), such as methylamino methyl, methylamino ethyl, dimethylamino methyl and so on.

The term "heterocycle" refers to a saturated cycloalkyl or heteroaryl containing heteroatoms, wherein, the heteroatoms can be selected from the group consisting of N, S, O, and any oxidized forms of N, S, and P, preferably, a saturated heterocycloalkyl containing N, such as piperidine and so on.

The term "substituted" refers to the replacement of hydrogen in a given structure by a specified substituent group.

The present disclosure comprises compounds of formula I-III in their free fir's, and also comprises pharmaceutically acceptable salts and stereoisomers thereof. The pharmaceutically acceptable salts of the present disclosure can be synthesized from the compound of the present disclosure which contains a basic or acidic moiety by conventional chemical methods. Generally, salts of basic compounds are prepared either by ion exchange chromatography or by reacting the free base with a stoichiometric amount or an excessive amount of an inorganic or organic acid in the form of a required salt in a suitable solvent or a combination of solvents. Similarly, salts of acidic compounds are formed by reactions with an appropriate inorganic or organic base.

Accordingly, the pharmaceutically acceptable salts of the compounds of this disclosure include conventional non-toxic salts of the compounds of this disclosure as formed by reacting a basic compound of this disclosure with an inorganic or organic acid. For example, the conventional non-toxic salts include the salts prepared from inorganic acids, such as hydrochloric acid, hydrobromic acid, sulfuric acid, sulfamic acid, phosphoric acid, nitric acid, and the like, and also include the salts prepared from organic acids, such as acetic acid, propionic acid, succinic acid, glycolic acid, stearic acid, lactic acid, malic acid, tartaric acid, citric acid, ascorbic acid, pamoic acid, maleic acid, hydroxymaleic acid, toluylic acid, glutamic acid, benzoic acid, salicylic acid, para-aminobenzenesulfonic acid, 2-acetoxy-benzoic acid, fumaric acid, toluenesulfonic acid, methanesulphonic acid, ethane disulfonic acid, oxalic acid, isethionic acid, trifluoroacetic acid and the like.

When the compound of the present disclosure is acidic, the suitable "pharmaceutically acceptable salt" refers to a salt prepared from pharmaceutically acceptable non-toxic bases, including inorganic bases and organic bases. Salts derived from such inorganic bases include aluminum, ammonium, calcium, copper, ferric, ferrous, lithium, magnesium, manganese, manganous, potassium, sodium, zinc salts and the like. Particularly preferred are ammonium, calcium, magnesium, potassium, and sodium salts. Salts derived from pharmaceutically acceptable organic non-toxic bases include salts of primary, secondary, and tertiary amines salts, and the substituted amines include naturally occurring substituted amines, cyclic amines, alkaline ion-exchange resins, such as arginine, betaine, caffeine, choline, N,N'-dibenzylethylenediamine, diethylamine, 2-diethylaminoethanol, 2-dimethylaminoethanol, aminoethanol, ethanolamine, ethylene diamine, N-ethylmorpholine, N-ethylpiperidine, dextrosamine, glucosamine, histidine, hydroxocobalamin, isopropylamine, lysine, methyl glucamine, morpholine, piperazine, piperidine, pyridine, polyamine resin, procaine, purine, theobromine, triethylamine, trimethylamine, tripropylamine, tromethamine and the like.

The compound of this disclosure may be prepared by employing reactions as shown in the following synthetic schemes (scheme 1-7), in addition to other standard procedures that are known in the literature or exemplified in experimental procedures. The compounds and synthetic processes of the present disclosure will be better understood in connection with the following synthetic schemes which illustrate the method by which the compound of the disclosure may be prepared. Such description is intended to be illustrative rather than limiting the scope of the present disclosure.

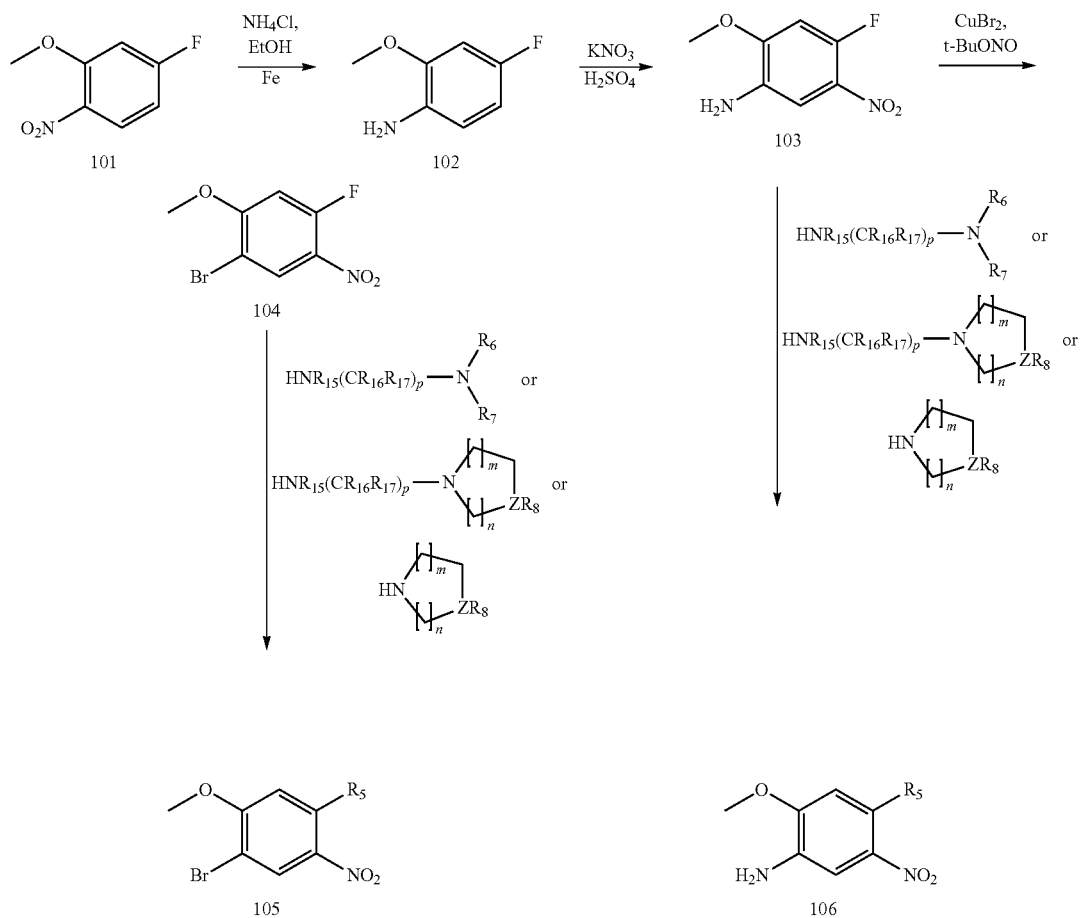
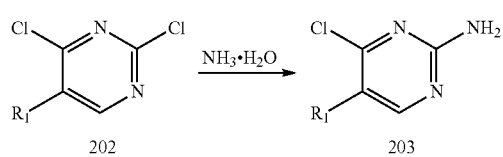

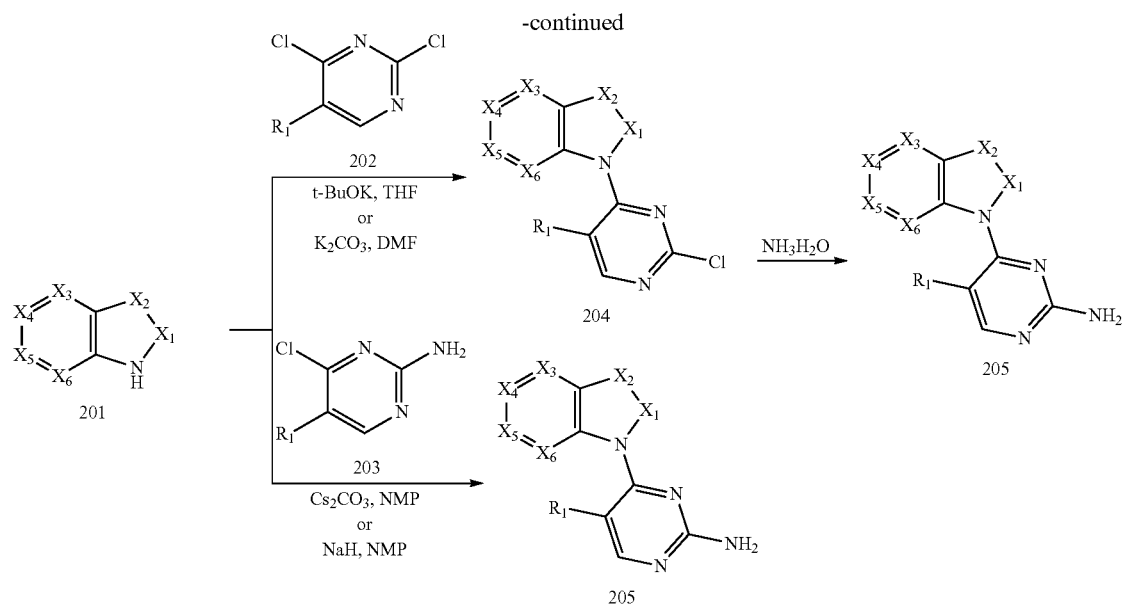
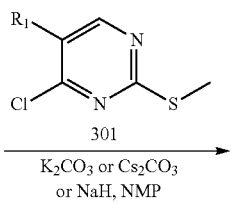
Scheme 3
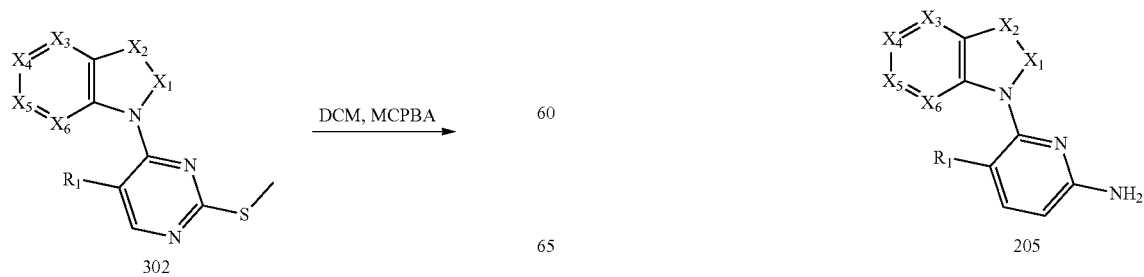

Scheme 4
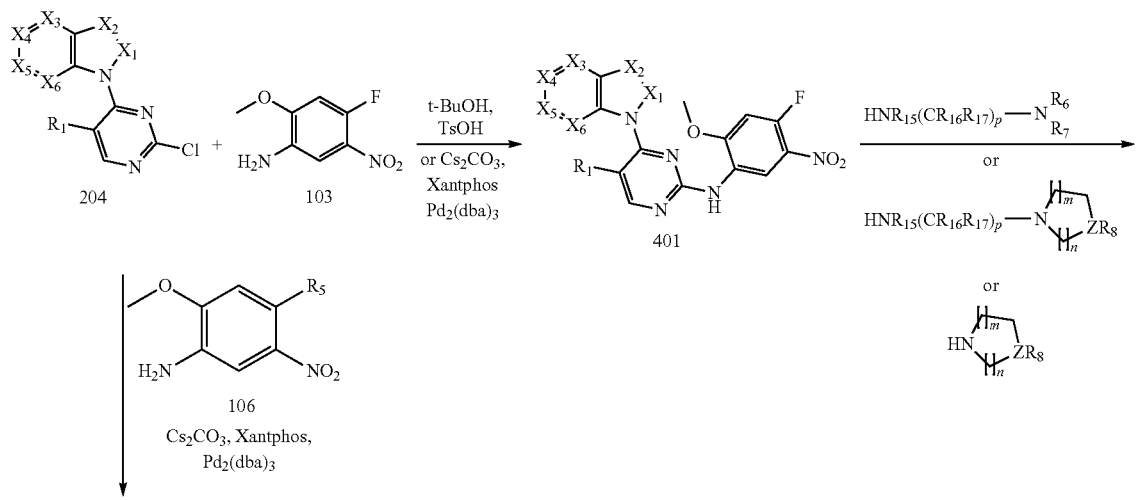
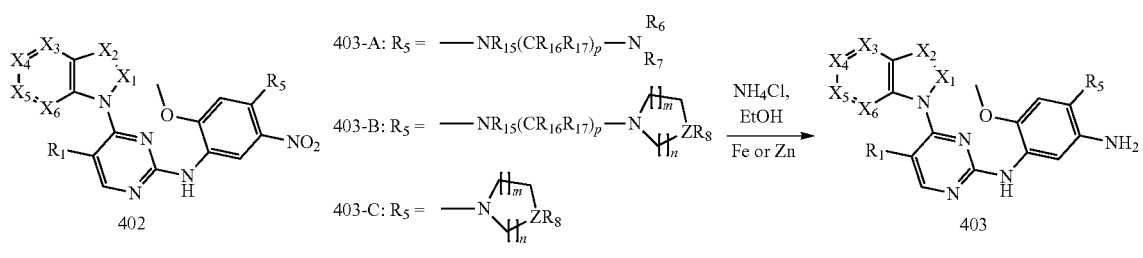
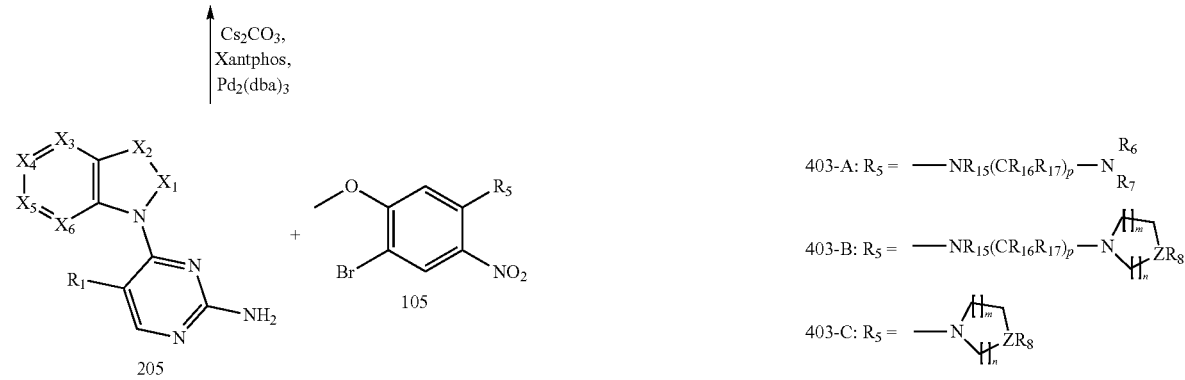

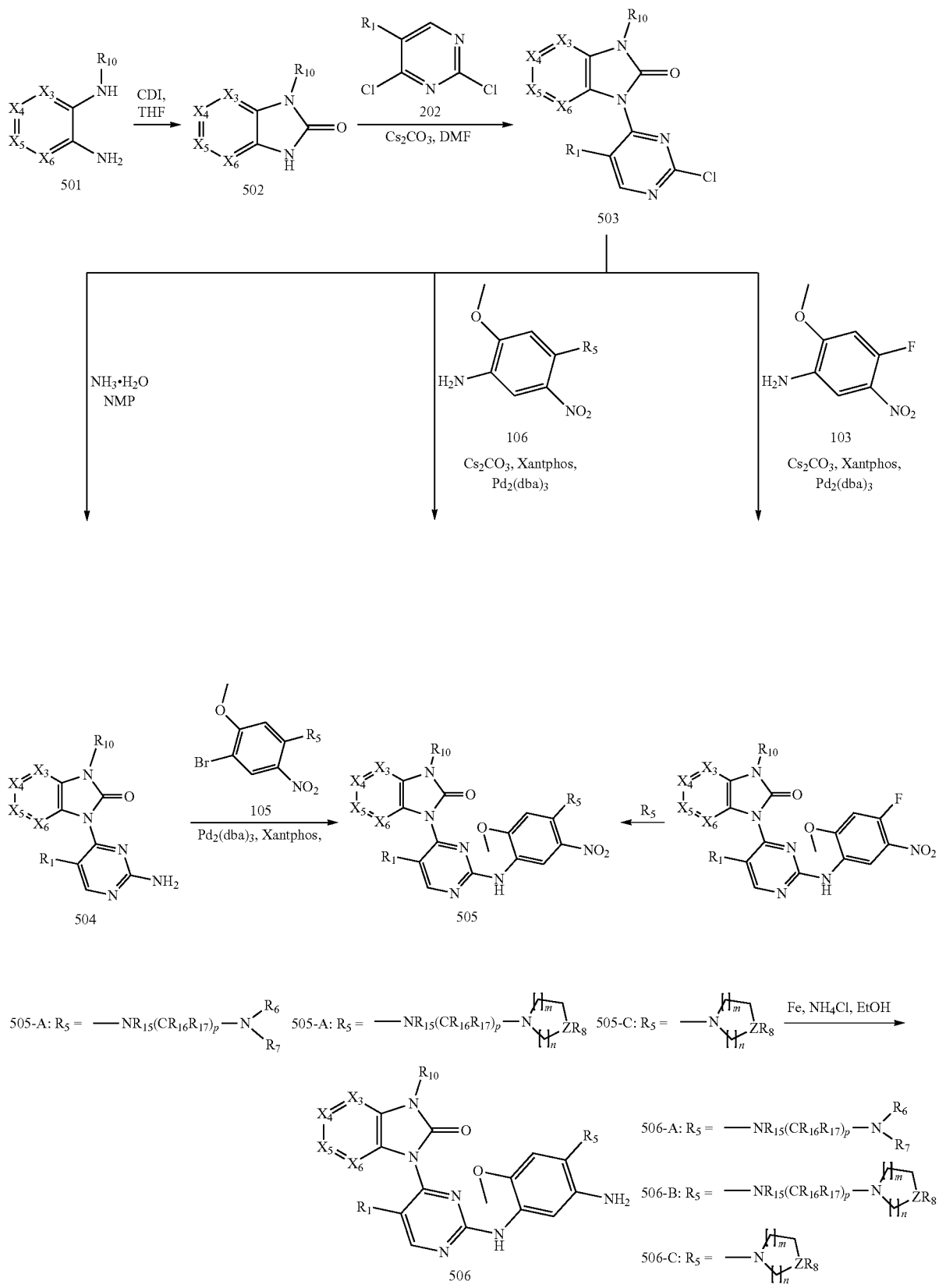
Scheme 5

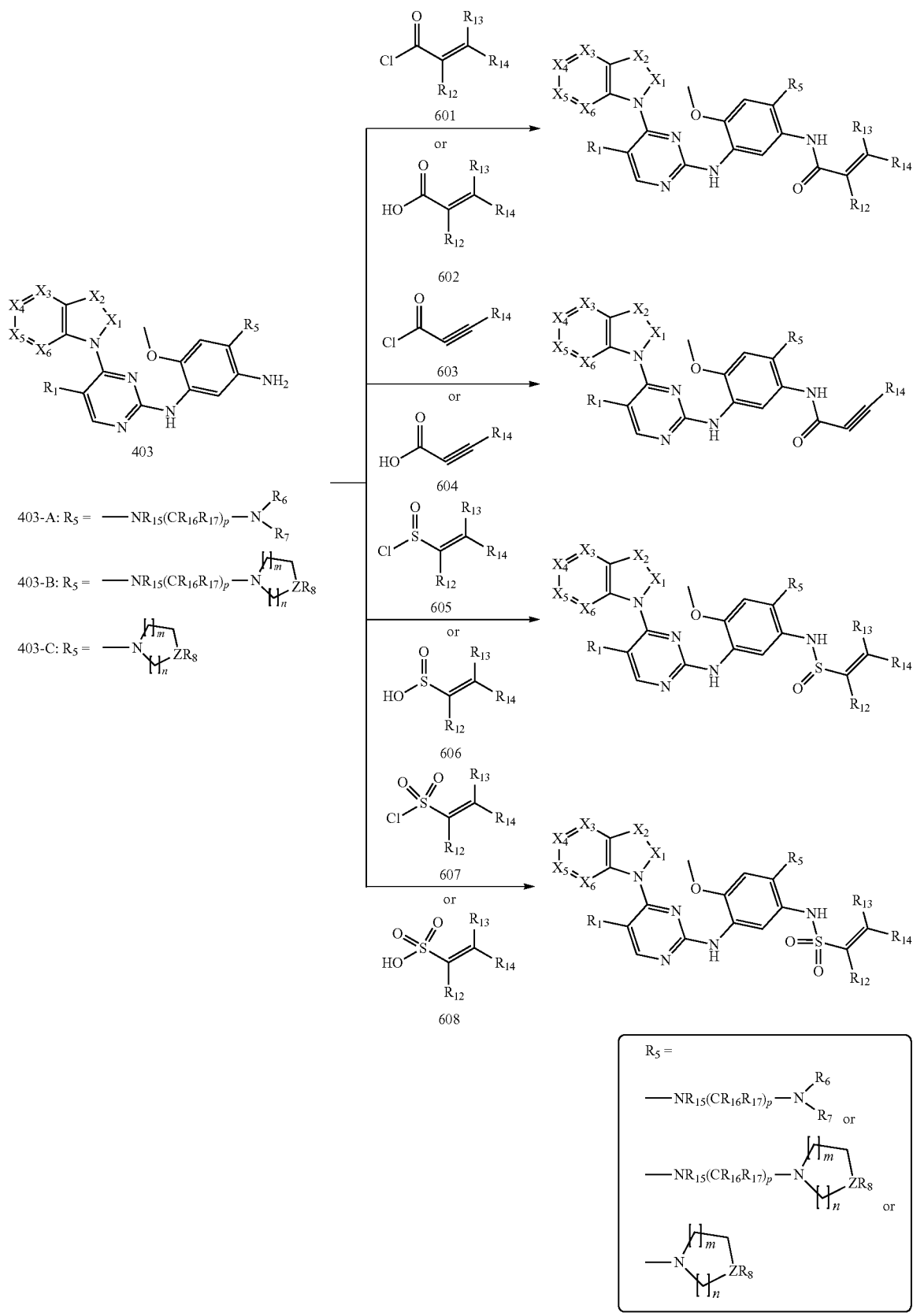

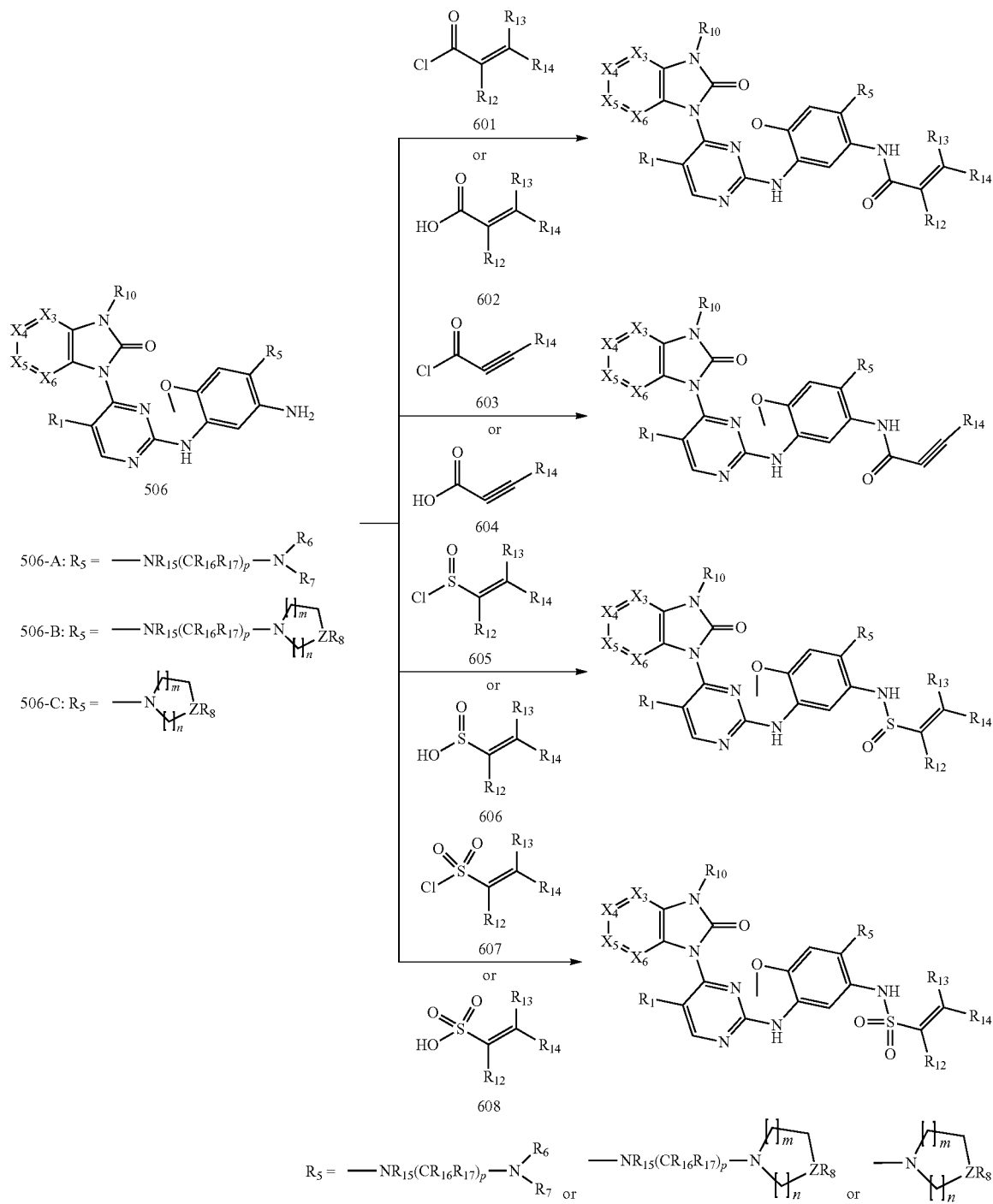

Example 1: Preparation of Intermediates 103, 104, 105 and 106 (Prepared According to Scheme 1)

Step 1a: Preparation of 4-fluoro-2-methoxyaniline (Intermediate 102): 2-Methoxy-4-fluoro-1-nitrobenzene (Intermediate 101) (20 g, 0.12 mol, 1.0 eq), ammonium chloride (13 g, 0.24 mol, 2.0 eq) and water (50 mL) were dissolved in ethanol (200 mL). After heated to 55° C., iron powder (13 g, 0.24 mol, 2.0 eq) was added portionwise. The temperature was raised to 85° C. and after reaction for 2 hours, the temperature was lowered to room temperature, filtration was performed and the solvent was rotary evaporated. The residue was dissolved in ethyl acetate which was then washed with water, washed with saturated brine, dried over anhydrous sodium sulfate, filtered and rotary evaporated to obtain 4-fluoro-2-methoxyaniline as a light green product (15 g, yield: 91%). LCMS (ESI): m/z 142[M+H]$^+$.

Step 1b: Preparation of 4-fluoro-2-methoxy-5-nitroaniline (Intermediate 103): Under an ice bath condition, 4-fluoro-2-methoxyaniline (Intermediate 102) (15 g, 106.4 mmol, 1.0 eq) was added dropwise to a concentrated sulfuric acid (150 mL) while controlling the temperature around 0° C. during the course of addition. After the forming solid was dissolved completely, potassium nitrate (11 g, 106.4 mmol, 1.0 eq) was added portionwise and the reaction was continued for 1 hour under this condition. The reaction was poured into ice water and the pH was adjusted to basic by sodium hydroxide. A vast amount of solid was precipitated out which was filtered and washed with water, petroleum ether, dried in air to give 4-fluoro-2-methoxy-5-nitroaniline as a brown solid (18 g, yield: 77%). LCMS (ESI): m/z 187 [M+H]$^+$.

Step 1c: Preparation of 1-bromo-4-fluoro-2-methoxy-5-nitrobenzene (Intermediate 104): Under nitrogen atmosphere, cupric bromide (3.568 g, 16 mmol, 1.5 eq) and tert-Butyl nitrite (3.399 g, 33 mmol, 3 eq) were mixed in acetonitrile (250 mL) and heated to 50° C. A solution of 4-fluoro-2-methoxy-5-nitroaniline (103) (2 g, 11 mmol, 1 eq) in acetonitrile (20 mL) was added dropwise to the system and stirred for reaction for additional 2.5 hours. The reaction temperature was lowered to room temperature and extraction was performed with ethyl acetate and water. The organic phase was washed with water, washed with brine, dried over anhydrous sodium sulfate, and concentrated in vacuo to yield the crude product as a brown oil which was purified by silica gel column chromatography (petroleum ether/ethyl acetate=10/1) to give 1-bromo-4-fluoro-2-methoxy-5-nitrobenzene as a yellow solid (1.87 g, yield: 69.57%).

Step 1d: Preparation of $N^1$-(4-bromo-5-methoxy-2-nitrophenyl)-$N^1$,$N^2$,$N^2$-trimethylethane-1,2-diamine (Intermediate 105-A-5): 1-Bromo-4-fluoro-2-methoxy-5-nitrobenzene (Intermediate 104) (1.87 g, 7.48 mmol, 1 eq), N, N-diisopropylethylamine (2.41 g, 17.8 mmol, 2.5 eq) and $N^1$,$N^1$,$N^2$-trimethylethane-1,2-diamine (1.146 g, 11.22 mmol, 1.5 eq) were dissolved in ethanol (50 mL) and heated to reflux and react under stirring for 16 hours. After the reaction was completed, the temperature was lowered to room temperature and extraction was performed with dichloromethane. The organic phase was washed with water and brine, dried over anhydrous sodium sulfate, concentrated in vacuo to give $N^1$-(4-bromo-5-methoxy-2-nitrophenyl)-$N^1$,$N^2$,$N^2$-trimethylethane-1,2-diamine as a red oil (2.3 g, crude) which was used for next step directly.

Step 1e: Preparation of $N^1$-(2-(dimethylamino)ethyl)-5-methoxy-$N^1$-methyl-2-nitrobenzene-1,4-diamine (Intermediate 106-A-11): 4-Fluoro-2-methoxy-5-nitroaniline (Intermediate 103) (2 g, 10.75 mmol, 1 eq), DIPEA (2.77 g, 21.5 mmol, 2 eq) and $N^1$,$N^1$,$N^2$-trimethylethane-1,2-diamine (1.644 g, 16.125 mmol, 1.5 eq) were mixed in tetrahydrofuran (50 mL). The mixture was stirred under reflux to react for 3 days. After the reaction was completed, the reaction temperature was lowered to room temperature and extraction was performed with dichloromethane and water. The organic phase was washed with water and brine, dried over anhydrous sodium sulfate, concentrated in vacuo and purified by silica gel column chromatography (dichloromethane/methanol/ammonium hydroxide=100/1/0.01) to give $N^1$-(2-(dimethylamino)ethyl)-5-methoxy-$N^1$-methyl-2-nitrobenzene-1,4-diamine as a red oil (1.8 g, crude).

Example 2: Preparation of Intermediate 204 (Prepared According to Scheme 2)

Preparation of 1-(2-chloro-5-methoxypyrimidin-4-yl)-1H-indole (Intermediate 204-6): 1H-indole (201-6) (1 g, 8.55 mmol, 1.0 eq) was dissolved in tetrahydrofuran (30 mL) and potassium tert-butoxide (1.44 g, 12.82 mmol, 1.5 eq) was added portionwise at 0° C. under nitrogen protection and reacted at room temperature for one hour. The reaction was re-cooled to room temperature and 2,4-dichloro-5-methoxypyrimidine (202-6) (2.3 g, 12.82, 1.5 eq) in tetrahydrofuran (20 mL) was added dropwise. After addition, the reaction was warmed to room temperature and continued reacting overnight. The reaction was poured into water, extracted with ethyl acetate which was then washed with saturated brine, dried over anhydrous sodium sulfate and rotary evaporated to obtain a residue which was washed with petroleum ether to give 1-(2-chloro-5-methoxypyrimidin-4-yl)-1H-indole as a beige solid (2.2 g, yield: 100%). LCMS (ESI): m/z 260 [M+H]$^+$.

The following Intermediates (204-8, 204-10, and 204-11) were prepared according to the method described above for the preparation of Intermediate 204-6, except that the Intermediates 201-6 and 202-6 therein were replaced by the corresponding Intermediates 201 and 202.

Preparation of Intermediate 204-8: 1-(2-chloro-5-methylpyrimidin-4-yl)-1H-indole (Intermediate 204-8) was prepared by reacting 1H-indole (201-6) with 2,4-dichloro-5-methylpyrimidine (202-8). LCMS (ESI): m/z 244[M+H]$^+$.

Preparation of Intermediate 204-10: 2-chloro-4-(1H-indol-1-yl)-N,N-dimethylpyrimidin-5-amine (Intermediate 204-10) was prepared by reacting 1H-indole (201-6) with 2,4-dichloro-N,N-dimethylpyrimidin-5-amine (202-10). LCMS (ESI): m/z 273[M+H]$^+$.

Preparation of Intermediate 204-11: 2-chloro-4-(1H-indol-1-yl)-N-methylpyrimidin-5-amine (Intermediate 204-11) was prepared by reacting 1H-indole (201-6) with 2,4-dichloro-N-methylpyrimidin-5-amine (202-11). LCMS (ESI): m/z 259[M+H]$^+$.

Example 3: Preparation of Intermediate 205 (Prepared According to Scheme 2 or 3)

Intermediate 205 was prepared by one of the three methods, the methods 3-1, 3-2 and 3-3, as described below:

Method 3-1 (Scheme 2):

Preparation of 4-(1H-indol-1-yl)-5-methoxypyrimidin-2-amine (Intermediate 205-6): Compound 1-(2-chloro-5-methoxypyrimidin-4-yl)-1H-indole (Intermediate 204-6) (1 g, 3.9 mmol, 1.0 eq), ammonium hydroxide (2 mL) and N,N-diisopropylethylamine (1 mL) were dissolved in N-methylpyrrolidone (10 mL) in a sealed reactor and heated to 110° C. reacting overnight. The reaction was cooled to room temperature and poured into water, extracted with ethyl acetate which was then washed with saturated brine, dried over anhydrous sodium sulfate and rotary evaporated. The residue was purified by silica gel column chromatography (eluent: petroleum ether/ethyl acetate=20/1 to 1/1) to give 4-(1H-indol-1-yl)-5-methoxypyrimidin-2-amine as a white solid (240 mg, yield: 26%). LCMS (ESI): m/z 241 [M+H]$^+$.

Method 3-2 (Scheme 2):

Preparation of 4-(1H-indol-1-yl)-5-(trifluoromethyl)pyrimidin-2-amine (Intermediate 205-5): Sodium hydride (210 mg, 7.0 mmol, 5.0 eq) was added to N-methylpyrrolidone (15 mL) at room temperature and then cooled in an ice bath and 1H-Indole (201-6) (410 mg, 3.5 mmol, 2.5 eq) was then added. After reaction at room temperature for 1 hour, the reaction was cooled in an ice bath and 4-chloro-5-(trifluoromethyl)pyrimidin-2-amine (203-5) (279 mg, 1.4 mmol, 1.0 eq) in N-methylpyrrolidone (1 mL) was added to the above mixture and stirred at room temperature for 1 hour.

Water and ethyl acetate were added and the layers were separated. The organic phase was dried, concentrated in vacuo and purified by silica gel column chromatography (eluent: petroleum ether/ethyl acetate=4/1 to 1/1) to give 4-(1H-indol-1-yl)-5-(trifluoromethyl)pyrimidin-2-amine as a yellow solid (220 mg, yield: 56%). LCMS (ESI): m/z 279[M+H]$^+$.

Preparation of 4-(5-methoxy-1H-pyrrolo[3,2-b]pyridin-1-yl)pyrimidin-2-amine (Intermediate 205-20): 5-Methoxy-1H-pyrrolo[3,2-b]pyridine (201-20) (200 mg, 1.35 mmol, 1 eq), cesium carbonate (877.5 mg, 2.7 mmol, 2 eq) and 4-chloropyrimidin-2-amine (203-20) (261 mg, 2.025 mmol, 1.5 eq) were mixed in N-methylpyrrolidone (5 mL). The mixture was heated to 150° C. and stirred to react for 2 hours. After the reaction was completed, the temperature was lowered to room temperature, and the reaction mixture was quenched with water, filtered and the residue was washed with water, dried in vacuum to give a gray solid (300 mg, yield: 92.13%). LCMS (ESI): m/z 242[M+H]$^+$.

Preparation of 4-(5-fluoro-1H-indol-1-yl)pyrimidin-2-amine (Intermediate 205-28): 5-Fluoro-1H-indole (201-28) (500 mg, 3.7 mmol, 1.0 eq), cesium carbonate (2.4 g, 7.4 mmol, 2.0 eq) and 4-chloropyrimidin-2-amine (203-28) (480 mg, 5.1 mmol, 1.0 eq) were dissolved in NMP (50 mL) and reacted at 150° C. for 1 hour. The reaction temperature was lowered to room temperature and the mixture was poured into water, filtered, and the residue was washed with water and dried to give 4-(5-fluoro-1H-indol-1-yl)pyrimidin-2-amine as a pink solid (500 mg, 59%). LCMS (ESI): m/z 229[M+H]$^+$.

Method 3-3 (Scheme 3):

Preparation of 4-(5-nitro-indol-1-yl)-pyrimidin-2-ylamine (Intermediate 205-34): 5-Nitro-1H-indole (201-34) (3 g, 18.5 mmol) and 4-chloro-2-(methylthio)pyrimidine (301-34) (2.98 g, 18.5 mmol) were dissolved in N, N-dimethylformamide (100 mL) at room temperature and potassium carbonate (5.1 g, 37 mmol) was then added and the mixture was heated to 80° C. to react overnight. Water (500 mL) was then added and the mixture was filtered directly and dried in vacuum to give 1-(2-(methylthio)pyrimidin-4-yl)-5-nitro-1H-indole (302-34) as a gray solid (5.2 g, yield: 98%). LCMS (ESI): m/z 287[M+H]$^+$. Compound 302-34 (0.5 g, 1.7 mmol) was dissolved in dichloromethane (15 mL) and 3-chloroperbenzoic acid (0.3, 1.7 mmol) was then added. After stirring at room temperature for 4 hours, a saturated aqueous sodium carbonate solution (20 mL) was added and the mixture was extracted with dichloromethane (20 mL) three times, which was dried and concentrated to give 1-(2-(methylsulfinyl)pyrimidin-4-yl)-5-nitro-1H-indole (303-34) as a yellow solid (0.51 g, yield: 98%). LCMS (ESI): m/z 303[M+H]$^+$. Compound 303-34 (0.51 g, 1.69 mmol) was dissolved in tetrahydrofuran (10 mL) and 20% ammonium hydroxide (2 mL) was then added. The mixture was reacted at 80° C. overnight in a sealed tube and water (20 mL) was then added and extracted with dichloromethane (20 mL) three times, which was dried and concentrated to give 4-(5-nitro-1H-indol-1-yl)pyrimidin-2-amine (205-34) as a yellow solid (0.37 g, yield: 99.5%). LCMS (ESI): m/z 256 [M+H]$^+$.

Preparation of 4-(5-((tert-butyldiphenylsilyl)oxy)-1H-indol-1-yl)pyrimidin-2-amine (Intermediate 205-36): Under nitrogen atmosphere, 5-((tert-butyldiphenylsilyl)oxy)-1H-indole (201-36) (800 mg, 2.15 mmol, 1.2 eq), 4-chloro-2-(methylthio)pyrimidine (301-34) (286 mg, 1.79 mmol, 1 eq), cesium carbonate (1160 mg, 3.57 mmol, 2 eq), Pd$_2$(dba)$_3$ (77 mg, 0.086 mmol, 0.05 eq) and Xantphos (91 mg, 0.16 mmol, 0.09 eq) were mixed in toluene (20 mL) and stirred at 110° C. to react for 1 hour. After the reaction was completed, the reaction temperature was lowered to room temperature, and the mixture was concentrated in vacuo and purified by silica gel column chromatography (petroleum ether/ethyl acetate=20/1) to give 5-((tert-butyldiphenylsilyl)oxy)-1-(2-(methylthio)pyrimidin-4-yl)-1H-indole (compound 302-36) as a gray solid (980 mg, crude). LCMS (ESI): m/z 496 [M+H]$^+$. Under nitrogen atmosphere and in an ice bath, compound 302-36 (240 mg, 0.485 mmol, 1 eq) was dissolved in dichloromethane (5 mL) and a solution of 3-chloroperbenzoic acid (118 mg, 0.528 mmol, 1.2 eq) in dichloromethane (2 mL) was then added to it dropwise. The mixture was reacted at room temperature for 30 minutes. After the reaction was completed, the mixture was quenched with a saturated sodium carbonate solution and extracted with dichloromethane and water. The organic phase was dried over anhydrous sodium sulfate and concentrated in vacuo to give 5-((tert-butyldiphenylsilyl)oxy)-1-(2-(methylsulfinyl)pyrimidin-4-yl)-1H-indole (303-36) as a gray solid (300 mg, crude). LCMS (ESI): m/z 512 [M+H]$^+$. Compound 303-36 (300 mg, 0.587 mmol, 1 eq) and ammonium hydroxide (5 mL) were dissolved in tetrahydrofuran (10 mL) in a sealed reactor. The mixture was stirred at 80° C. for 2 hours. After the reaction was completed, the reaction temperature was lowered to room temperature, and the mixture was concentrated in vacuo and purified by silica gel column chromatography (petroleum ether/ethyl acetate=1/1) to give 4-(5-((tert-butyldiphenylsilyl)oxy)-1H-indol-1-yl)pyrimidin-2-amine (205-36) as a white solid (200 mg, yield: 73.53%). LCMS (ESI): m/z 464 [M+H]$^+$.

Preparation of 4-(5-methoxy-1H-indol-1-yl)pyrimidin-2-amine (Intermediate 205-27): Under an ice bath condition, 5-methoxy-1H-indole (210-27) (500 mg, 3.4 mmol, 1 eq) was dissolved in N-methylpyrrolidone (5 mL) and sodium hydride (272 mg, 6.8 mmol, 2 eq) was then added and the mixture was stirred at room temperature for 30 minutes. Compound 4-chloro-2-(methylthio)pyrimidine (301-15) (544 mg, 3.4 mmol, 1 eq) was added dropwise to the system and stirred for reaction for additional 1 hour. After the reaction was completed, water was added to quench the reaction and filtered. The residue was washed with water and dried to give methoxy-1-(2-(methylthio)pyrimidin-4-yl)-1H-indole (302-27) as a yellow solid (1.02 g, crude). LCMS (ESI): m/z 272 [M+H]$^+$. Compound 5-methoxy-1-(2-(methylthio)pyrimidin-4-yl)-1H-indole (302-27) (500 mg, 1.845 mmol, 1 eq) was dissolved in dichloromethane (20 mL) and cooled to about 0° C. under nitrogen protection condition, and to which was added dropwise 3-chloroperbenzoic acid (374.4 mg, 1.845 mmol, 1.2 eq) in dichloromethane (2 mL). After addition, the mixture was reacted at room temperature for 1 hour. The reaction solution was washed with sodium carbonate aqueous solution and saturated brine, dried over anhydrous sodium sulfate and rotary evaporated to give a yellow solid 5-methoxy-1-(2-(methylsulfinyl)pyrimidin-4-yl)-1H-indole (303-27) as a yellow solid (580 mg, crude). LCMS (ESI): m/z 288 [M+H]$^+$. Compound 5-methoxy-1-(2-(methylsulfinyl)pyrimidin-4-yl)-1H-indole (580 mg, 2.02 mmol, 1 eq) and ammonium hydroxide (5 mL) were dissolved in tetrahydrofuran (10 mL) and heated to 80° C. and continued reacting for 2 hours in a sealed reactor. The reaction solution temperature was lowered to room temperature and rotary evaporation was performed to leave a residue which was purified by silica gel column chromatography (dichloromethane/methanol=200/1) to give 4-(5-methoxy-1H-indol-1-yl)pyrimidin-2-amine (205-27) as a light yellow solid (407 mg, yield: 89.92%). LCMS (ESI): m/z 241 [M+H]$^+$.

The following Intermediates (205-8, 205-10) were prepared according to the method for Intermediate 205-6 in the synthetic method 3-1 described above, except that the Intermediate 204-6 therein was replaced by corresponding Intermediate 204.

Preparation of Intermediate 205-8: The synthetic method was similar to method 3-1 of EXAMPLE 3 for the preparation of Intermediate 205-6, except that 1-(2-chloro-5-methoxypyrimidin-4-yl)-1H-indole (204-6) therein was replaced by 1-(2-chloro-5-methylpyrimidin-4-yl)-1H-indole (204-8). 4-(1H-indol-1-yl)-5-methylpyrimidin-2-amine (Intermediate 205-8) was prepared. LCMS (ESI): m/z 225 [M+H]$^+$.

Preparation of Intermediate 205-10: The synthetic method was similar to method 3-1 of EXAMPLE 3 for the preparation of Intermediate 205-6, except that in which 1-(2-chloro-5-methoxypyrimidin-4-yl)-1H-indole (204-6) therein was replaced by 2-chloro-4-(1H-indol-1-yl)-N,N-dimethylpyrimidin-5-amine (204-10). 4-(1H-indol-1-yl)-N$^5$,N$^5$-dimethylpyrimidine-2,5-diamine (Intermediate 205-10) was prepared. LCMS (ESI): m/z 254 [M+H]$^+$.

The following Intermediates (205-8, 205-10) were prepared according to the method of Intermediate 205-28 of the synthetic method 3-2 described above, except that the Intermediates 201-28 and 203-28 therein were replaced by Intermediates 201 and 203, respectively.

Preparation of Intermediate 205-29: The synthetic method was similar to method 3-2 of EXAMPLE 3 for the preparation of Intermediate 205-28, except that 5-fluoro-1H-indole (201-28) therein was replaced by 6-fluoro-1H-indole (201-29) and 4-chloro-5-(trifluoromethyl)pyrimidin-2-amine (203-5) therein was replaced by 4-chloropyrimidin-2-amine (203-28). 4-(6-Fluoro-1H-indol-1-yl)pyrimidin-2-amine (Intermediate 205-29) was prepared. LCMS (ESI): m/z 229 [M+H]$^+$.

Preparation of Intermediate 205-30: The synthetic method was similar to method 3-2 of EXAMPLE 3 for the preparation of Intermediate 205-28, except that 5-fluoro-1H-indole (201-28) therein was replaced by 4-fluoro-1H-indole (201-30) and 4-chloro-5-(trifluoromethyl)pyrimidin-2-amine (203-5) therein was replaced by 4-chloropyrimidin-2-amine (203-28). 4-(4-Fluoro-1H-indol-1-yl)pyrimidin-2-amine (Intermediate 205-30) was prepared. LCMS (ESI): m/z 229 [M+H]$^+$.

Preparation of Intermediate 205-31: The synthetic method was similar to method 3-2 of EXAMPLE 3 for the preparation of Intermediate 205-28, except that 5-fluoro-1H-indole (201-28) therein was replaced by 5-chloro-1H-indole (201-31) and 4-chloro-5-(trifluoromethyl)pyrimidin-2-amine (203-5) therein was replaced by 4-chloropyrimidin-2-amine (203-28). 4-(5-Chloro-1H-indol-1-yl)pyrimidin-2-amine (Intermediate 205-31) was prepared. LCMS (ESI): m/z 245 [M+H]$^+$.

Preparation of Intermediate 205-124: The synthetic method was similar to method 3-2 of EXAMPLE 3 for the preparation of Intermediate 205-20, except that 5-methoxy-1H-pyrrolo[3,2-b]pyridine (201-20) therein was replaced by 5-chloro-1H-pyrrolo[3,2-b]pyridine (201-124). 4-(5-Chloro-1H-pyrrolo[3,2-b]pyridin-1-yl)pyrimidin-2-amine (Intermediate 205-124) was prepared. LCMS (ESI): m/z 246 [M+H]$^+$.

The following Intermediate (205-39) was prepared according to the method of Intermediate 205-34 of the synthetic method 3-3 described above, except that the Intermediate 201-34 therein was replaced by corresponding Intermediate 201.

Preparation of Intermediate 205-39: The synthetic method was similar to method 3-3 of EXAMPLE 3 for the preparation of Intermediate 205-34, except that 5-nitro-1H-indole (201-34) therein was replaced by (1H-indol-5-yl)methanol (201-39). 1-(2-Aminopyrimidin-4-yl)-1H-indol-5-yl)methanol (Intermediate 205-39) was prepared. LCMS (ESI): m/z 241 [M+H]$^+$.

The following Intermediates (205-37, 205-38) were prepared according to the method of Intermediate 205-36 of the synthetic method 3-3, except that the Intermediate 201-36 therein was replaced by corresponding Intermediate 201.

Preparation of Intermediate 205-37: The synthetic method was similar to method 3-3 of EXAMPLE 3 for the preparation of Intermediate 205-36, except that 5-((tert-butyldiphenylsilyl)oxy)-1H-indole (201-36) therein was replaced by 5-(2-((tert-butyldiphenylsilyl)oxy)ethoxy)-1H-indole (201-37). 4-(5-(2-((tert-Butyldiphenylsilyl)oxy)ethoxy)-1H-indol-1-yl)pyrimidin-2-amine (Intermediate 205-37) was prepared. LCMS (ESI): m/z 509 [M+H]$^+$.

Preparation of Intermediate 205-38: The synthetic method was similar to method 3-3 of EXAMPLE 3 for the preparation of Intermediate 205-36, except that 5-((tert-butyldiphenylsilyl)oxy)-1H-indole (201-36) therein was replaced by 5-(2-methoxyethoxy)-1H-indole (201-38). 4-(5-(2-Methoxyethoxy)-1H-indol-1-yl)pyrimidin-2-amine (Intermediate 205-38) was prepared. LCMS (ESI): m/z 285 [M+H]$^+$.

The following Intermediates (205-33-205-46) were prepared according to the method of Intermediate 205-27 of the synthetic method 3-3, except that the Intermediate 201-27 therein was replaced by corresponding Intermediate 201.

Preparation of Intermediate 205-33: The synthetic method was similar to method 3-3 of EXAMPLE 3 for the preparation of Intermediate 205-27, except that 5-methoxy-1H-indole (201-27) therein was replaced by 1H-indole-5-carbonitrile (201-33). 1-(2-Aminopyrimidin-4-yl)-1H-indole-5-carbonitrile (Intermediate 205-33) was prepared. LCMS (ESI): m/z 236 [M+H]$^+$.

Preparation of Intermediate 205-46: The synthetic method was similar to method 3-3 of EXAMPLE 3 for the preparation of Intermediate 205-27, except that 5-methoxy-1H-indole (201-27) therein was replaced by 3-chloro-1H-indole (201-46). 4-(3-Chloro-1H-indol-1-yl)pyrimidin-2-amine (Intermediate 205-46) was prepared. LCMS (ESI): m/z 245 [M+H]$^+$.

Example 4: Preparation of Intermediate 403
(Prepared According to Scheme 4)

Intermediate 403 was prepared by one of the three methods, methods 4-1, 4-2 and 4-3, as described below:
Method 4-1 (Prepared Through Intermediates 103 and 204):
Step 4-1a: Preparation of N-(4-fluoro-2-methoxy-5-nitrophenyl)-4-(1H-indol-1-yl)pyrimidin-2-amine (Intermediate 401-77): A mixed solution of compound 1-(2-chloropyrimidin-4-yl)-1H-indole (204-6) (500 mg, 2.18 mmol, 1 eq), 4-methylbenzenesulfonic acid (450.47 mg, 2.616 mmol, 1.2 eq) and compound 4-fluoro-2-methoxy-5-nitroaniline (103) (405.5 mg, 2.18 mmol, 1 eq) in tert-butanol (15 mL) was stirred to react at 110° C. for 16 hours in a sealed reactor. The reaction temperature was lowered to room temperature and concentration was performed in vacuo to give a yellow solid. The yellow solid was washed with a 2N aqueous sodium hydroxide solution and petroleum ether/ethyl acetate 10/1, concentrated in vacuo to give N-(4-fluoro-2-methoxy-5- nitrophenyl)-4-(1H-indol-1-yl)pyrimidin-2-amine as a yellow solid (570 mg, yield: 68.88%). LCMS (ESI): m/z 380 [M+H]$^+$.

Step 4-1b: Preparation of N-(4-(3-(dimethylamino)azetidin-1-yl)-2-methoxy-5-nitrophenyl)-4-(1H-indol-1-yl)pyrimidin-2-amine (Intermediate 401-C-77): N-(4-fluoro-2-methoxy-5-nitrophenyl)-4-(1H-indol-1-yl)pyrimidin-2-amine (401-77) (150 mg, 0.4 mmol, 1.0 eq) was dissolved in 30 mL tetrahydrofuran, and then N,N-diisopropylethylamine (153 mg, 1.2 mmol, 3.0 eq) and N,N-dimethylazetidin-3-amine hydrochloride (81 mg, 0.6 mmol, 1.5 eq) were added in sequence. The mixture was heated to 80° C. and stirred for 5 hours. After the reaction was completed, the temperature was lowered to room temperature and extraction was performed with ethyl acetate and water. The organic phase was washed with water and brine, dried over anhydrous sodium sulfate, concentrated in vacuo and purified by silica gel column chromatography (dichloromethane/methanol=150/1~100/1) to give N-(4-(3-(dimethylamino)azetidin-1-yl)-2-methoxy-5-nitrophenyl)-4-(1H-indol-1-yl)pyrimidin-2-amine (402-C-77) as a red solid (170 mg, yield: 93%). LCMS (ESI): m/z 460[M+H]$^+$.

Step 4-1c: Preparation of N$^1$-(4-(1H-indol-1-yl)pyrimidin-2-yl)-4-(3-(dimethylamino) azetidin-1-yl)-6-methoxybenzene-1,3-diamine (Intermediate 403-C-77): N-(4-(3-(dimethylamino)azetidin-1-yl)-2-methoxy-5-nitrophenyl)-4-(1H-indol-1-yl)pyrimidin-2-amine (402-C-77) (170 mg, 0.37 mmol, 1.0 eq) and ammonia chloride (65 mg, 1.2 mmol, 8.0 eq) were mixed in ethanol (30 mL) and water (7 mL) and heated to 50° C. Reduced iron powder (165 mg, 2.96 mmol, 8.0 eq) was then added to it and heated to 80° C. to react for 2 hours. After the reaction was completed, the mixture was filtered and the filtrate was concentrated and extracted with dichloromethane. The organic phase was dried over anhydrous sodium sulfate and rotary evaporated in vacuo to give product N$^1$-(4-(1H-indol-1-yl)pyrimidin-2-yl)-4-(3-(dimethylamino)azetidin-1-yl)-6-methoxybenzene-1,3-diamine (179 mg, crude). LCMS (ESI): m/z 430[M+H]$^+$.

Method 4-2 (Prepared Through Intermediates 105 and 205):

Step 4-2a: Preparation of N$^1$-(4-(1H-indol-1-yl)-5-(trifluoromethyl)pyrimidin-2-yl)-N$^4$-(2-(dimethylamino)ethyl)-2-methoxy-N$^4$-methyl-5-nitrobenzene-1,4-diamine (Intermediate 402-A-5): Under nitrogen protection, 4-(1H-indol-1-yl)-5-(trifluoromethyl)pyrimidin-2-amine (205-5) (265 mg, 0.95 mmol, 1.2 eq), N$^1$-(4-bromo-5-methoxy-2-nitrophenyl)-N$^1$,N$^2$,N$^2$-trimethylethane-1,2-diamine (105-A-1) (266 mg, 0.80 mmol, 1.0 eq), cesium carbonate (782 mg, 2.4 mmol, 3.0 eq), 4,5-bisdiphenylphosphine-9,9-dimethylxanthene (46 mg, 0.08 mmol, 0.1 eq) and Pd$_2$(dba)$_3$ (46 mg, 0.04 mmol, 0.05 eq) were added to toluene (35 mL) and refluxed to react for 6 hours. After cooling to room temperature, the reaction was filtered and the filtrate was concentrated in vacuo and purified by silica gel column chromatography (eluent: dichloromethane/methanol=50/1 to 10/1) to give N$^1$-(4-(1H-indol-1-yl)-5-(trifluoromethyl)pyrimidin-2-yl)-N$^4$-(2-(dimethylamino)ethyl)-2-methoxy-N$^4$-methyl-5-nitrobenzene-1,4-diamine as a red solid (152 mg, yield: 36%). LCMS (ESI): m/z 530[M+H]$^+$.

Step 4-2b: Preparation of N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (Intermediate 403-A-5): N$^1$-(4-(1H-indol-1-yl)-5-(trifluoromethyl)pyrimidin-2-yl)-N$^4$-(2-(dimethylamino)ethyl)-2-methoxy-N$^4$-methyl-5-nitrobenzene-1,4-diamine (402-5) (140 mg, 0.26 mmol, 1.0 eq) and ammonia chloride (114 mg, 2.12 mmol, 8.0 eq) were added to ethanol (30 mL) and water (8 mL), and heated to 50° C. Reduced iron powder (127 mg, 2.26 mmol, 8.5 eq) was added portionwise and heated to reflux to react for 1 hour. The reaction temperature was lowered to room temperature and concentration was performed in vacuo and extraction was performed with dichloromethane. The organic phase was dried over anhydrous sodium sulfate and concentrated in vacuo to give N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine as a brown oil (130 mg, yield: 98%). LCMS (ESI): m/z 500[M+H]$^+$.

Method 4-3 (Prepared Through Intermediates 204 and 106)

Step 4-3a: Preparation of N$^2$-(4-((2-(dimethylamino)ethyl)(methyl)amino)-2-methoxy-5-nitrophenyl)-4-(1H-indol-1-yl)-N$^5$-methylpyrimidine-2,5-diamine (Intermediate 402-A-11): 2-chloro-4-(1H-indol-1-yl)-N-methylpyrimidin-5-amine (204-11) (268 mg, 1.036 mmol) was dissolved in toluene (40 mL) and then N$^1$-(2-(dimethylamino)ethyl)-5-methoxy-N$^1$-methyl-2-nitrobenzene-1,4-diamine (106-A-11) (278 mg, 1.036 mmol, 1.0 eq), Pd$_2$(dba)$_3$ (94.8 mg, 0.1036 mmol, 0.1 eq), cesium carbonate (675 mg, 2.072 mmol, 2.0 eq) and 4,5-bisdiphenylphosphine-9,9-dimethylxanthene (60 mg, 0.1036 mmol, 0.1 eq) were added to it in sequence. The mixture was protected under nitrogen and stirred at 100° C. for 4 hours. The mixture was cooled to room temperature, concentrated and purified by silica gel column chromatography (dichloromethane/methanol=40/1) to give N$^2$-(4-((2-(dimethylamino)ethyl)(methyl)amino)-2-methoxy-5-nitrophenyl)-4-(1H-indol-1-yl)-N$^5$-methylpyrimidine-2,5-diamine as a yellow solid (263 mg, yield: 51.8%). LCMS (ESI): m/z 491[M+H]$^+$.

Step 4-3b: Preparation of N$^4$-(4-(1H-indol-1-yl)-5-(methylamino)pyrimidin-2-yl)-N$^1$-(2-(dimethylamino)ethyl)-5-methoxy-N$^1$-methylbenzene-1,2,4-triamine (Intermediate 403-A-11): N$^2$-(4-((2-(Dimethylamino)ethyl)(methyl)amino)-2-methoxy-5-nitrophenyl)-4-(1H-indol-1-yl)-N$^5$-methylpyrimidine-2,5-diamine (402-A-11) (260 mg, 0.537 mmol, 1.0 eq) was dissolved in methanol (40 mL) and then zinc powder (279 mg, 4.297 mmol, 8.0 eq) and ammonia chloride (230 mg, 4.297 mmol, 8.0 eq) were added. The mixture was stirred at 60° C. for 4 hours and then cooled to room temperature. Dichloromethane was added to it and filtered. The filtrate was washed with water and saturated brine. The organic phase was dried over anhydrous sodium sulfate, concentrated to give N$^4$-(4-(1H-indol-1-yl)-5-(methylamino)pyrimidin-2-yl)-N$^1$-(2-(dimethylamino)ethyl)-5-methoxy-N$^1$-methylbenzene-1,2,4-triamine as a yellow solid (226 mg, crude). LCMS (ESI): m/z 461[M+H]$^+$.

The following Intermediates (403-C-78, 403-C-79, 403-B-80, 403-B-81, 403-B-82, 403-C-84) were prepared according to the synthetic method 4-1.

Preparation of Intermediate 403-C-78: The synthetic method was similar to that described for the synthesis of 403-C-77 in method 4-1 of EXAMPLE 4, except that compound N,N-dimethylazetidin-3-amine hydrochloride therein was replaced by (S)—N,N-dimethylpyrrolidin-3-amine. (S)—N$^1$-(4-(1H-Indol-1-yl)pyrimidin-2-yl)-4-(3-(dimethylamino)pyrrolidin-1-yl)-6-methoxybenzene-1,3-diamine (403-C-78) was prepared. LCMS (ESI): m/z 444 [M+H]$^+$.

Preparation of Intermediate 403-C-79: The synthetic method was similar to that described for the synthesis of Intermediate 403-C-77 in method 4-1 of EXAMPLE 4, except that N,N-dimethylazetidin-3-amine hydrochloride therein was replaced by (R)—N,N-dimethylpyrrolidin-3-amine. (R)—N$^1$-(4-(1H-Indol-1-yl)pyrimidin-2-yl)-4-(3-

(dimethylamino)pyrrolidin-1-yl)-6-methoxybenzene-1,3-diamine (403-C-79) was repaired. LCMS (ESI): m/z 444 [M+H]$^+$.

Preparation of Intermediate 403-B-80: The synthetic method was similar to method 4-1 of EXAMPLE 4. N-(4-fluoro-2-methoxy-5-nitrophenyl)-4-(1H-indol-1-yl)pyrimidin-2-amine (401-6) (250 mg, 0.659 mmol, 1.0 eq) was dissolved in ethanol (30 mL) and N, N-diisopropylethylamine (255 mg, 1.978 mmol, 1.0 eq) and N-methyl-2-(pyrrolidin-1-yl)ethan-1-amine (380 mg, crude) were added to it. The mixture was heated to 100° C. and continued to react overnight in a sealed tube. After the reaction was completed, the reaction temperature was lowered to room temperature and dilution was performed with ethyl acetate. The organic phase was washed with water and saturated brine, dried over anhydrous sodium sulfate, concentrated and purified by silica gel column chromatography (eluent: dichloromethane/methanol=60/1 to 50/1) to give N$^1$-(4-(1H-indol-1-yl)pyrimidin-2-yl)-2-methoxy-N$^4$-methyl-5-nitro-N$^4$-(2-(pyrrolidin-1-yl)ethyl)benzene-1,4-diamine (402-B-80) as a yellow solid (257 mg, yield: 80.0%). LCMS (ESI): m/z 488[M+H]$^+$. N$^1$-(4-(1H-indol-1-yl)pyrimidin-2-yl)-2-methoxy-N$^4$-methyl-5-nitro-N$^4$-(2-(pyrrolidin-1-yl)ethyl)benzene-1,4-diamine (402-B-80) (257 mg, 0.527 mmol, 1.0 eq) was dissolved in methanol (40 mL) and then zinc powder (274 mg, 4.216 mmol, 8.0 eq) and ammonia chloride (225 mg, 4.216 mmol, 8.0 eq) were added. The mixture was stirred at 60° C. for 4 hours, cooled to room temperature, diluted with dichloromethane and filtered. The filtrate was washed with water and saturated brine. The organic phase was dried over anhydrous sodium sulfate, concentrated to give N$^4$-(4-(1H-indol-1-yl)pyrimidin-2-yl)-5-methoxy-N$^1$-methyl-N$^1$-(2-(pyrrolidin-1-yl)ethyl)benzene-1,2,4-triamine (403-B-80) as a yellow solid (169 mg, crude). LCMS (ESI): m/z 458 [M+H]$^+$.

Preparation of Intermediate 403-B-81: The synthetic method was similar to that described for the synthesis of Intermediate 403-B-80 in method 4-1 of EXAMPLE 4, except that N-methyl-2-(pyrrolidin-1-yl)ethan-1-amine therein was replaced by N-methyl-2-(piperidin-1-yl)ethan-1-amine. N$^4$-(4-(1H-Indol-1-yl)pyrimidin-2-yl)-5-methoxy-N$^1$-methyl-N$^1$-(2-(piperidin-1-yl)ethyl)benzene-1,2,4-triamine (Intermediate 403-B-81) was prepared. LCMS (ESI): m/z 472 [M+H]$^+$.

Preparation of Intermediate 403-B-82: The synthetic method was similar to that described for the synthesis of Intermediate 403-B-80 in method 4-1 of EXAMPLE 4, except that N-methyl-2-(pyrrolidin-1-yl)ethan-1-amine therein was replaced by N-methyl-2-morpholinoethan-1-amine. N$^4$-(4-Indol-1-yl-pyrimidin-2-yl)-5-methoxy-N$^1$-methyl-N$^1$-(2-morpholin-4-yl-ethyl)-benzene-1,2,4-triamine (Intermediate 403-B-82) was prepared. LCMS (ESI): m/z 474 [M+H]$^+$.

Preparation of Intermediate 403-C-84: The synthetic method was similar to that described for the synthesis of Intermediate 403-C-77 in method 4-1 of EXAMPLE 4, except that N,N-dimethylazetidin-3-amine hydrochloride therein was replaced by N-methylpiperazine. N$^1$-(4-(1H-Indol-1-yl)pyrimidin-2-yl)-6-methoxy-4-(4-methylpiperazin-1-yl)benzene-1,3-diamine (Intermediate 403-C-84) was obtained. LCMS (ESI): m/z 444 [M+H]$^+$.

The following Intermediates (403-A-6, 403-A-8, 403-A-10, 402-A-20, 403-A-27, 403-A-28, 403-A-29, 403-A-30, 403-A-31, 403-A-33, 403-A-34, 403-A-36, 403-A-37, 403-A-38, 403-A-39, 403-A-41, 403-A-46, 403-A-124) were prepared according to the synthetic method 4-2, except that the Intermediate 205-5 therein was replaced by corresponding Intermediate 205.

Preparation of Intermediate 403-A-6: The synthetic method was similar to method 4-2 of EXAMPLE 4, except that 4-(1H-indol-1-yl)-5-(trifluoromethyl)pyrimidin-2-amine (205-5) therein was replaced by 4-(1H-indol-1-yl)-5-methoxypyrimidin-2-amine (205-6). N$^4$-(4-(1H-Indol-1-yl)-5-methoxypyrimidin-2-yl)-N$^1$-(2-(dimethylamino)ethyl)-5-methoxy-N$^1$-methylbenzene-1,2,4-triamine (Intermediate 403-A-6) was prepared. LCMS (ESI): m/z 462 [M+H]$^+$.

Preparation of Intermediate 403-A-8: The synthetic method was similar to method 4-2 of EXAMPLE 4, except that 4-(1H-indol-1-yl)-5-(trifluoromethyl)pyrimidin-2-amine (205-5) was replaced by 4-(1H-indol-1-yl)-5-methylpyrimidin-2-amine (205-8). N$^4$-(4-(1H-Indol-1-yl)-5-methylpyrimidin-2-yl)-N$^1$-(2-(dimethylamino)ethyl)-5-methoxy-N$^1$-methylbenzene-1,2,4-triamine (Intermediate 403-A-8) was prepared. LCMS (ESI): m/z 446 [M+H]$^+$.

Preparation of Intermediate 403-A-10: The synthetic method was similar to method 4-2 of EXAMPLE 4, except that 4-(1H-indol-1-yl)-5-(trifluoromethyl)pyrimidin-2-amine (205-5) therein was replaced by 4-(1H-indol-1-yl)-N$^5$,N$^5$-dimethylpyrimidine-2,5-diamine (205-10). N$^4$-(5-(Dimethylamino)-4-(1H-indol-1-yl)pyrimidin-2-yl)-N$^1$-(2-(dimethylamino)ethyl)-5-methoxy-N$^1$-methylbenzene-1,2,4-triamine (Intermediate 403-A-10) was prepared. LCMS (ESI): m/z 475 [M+H]$^+$.

Preparation of Intermediate 403-A-20: The synthetic method was similar to method 4-2 of EXAMPLE 4, except that 4-(1H-indol-1-yl)-5-(trifluoromethyl)pyrimidin-2-amine (205-5) therein was replaced by 4-(5-methoxy-1H-pyrrolo[3,2-b]pyridin-1-yl)pyrimidin-2-amine (205-20). N$^1$-(2-(Dimethylamino)ethyl)-5-methoxy-N$^4$-(4-(5-methoxy-1H-pyrrolo[3,2-b]pyridin-1-yl)pyrimidin-2-yl)-N$^1$-methyl-2-nitrobenzene-1,4-diamine (Intermediate 403-A-20) was prepared. LCMS (ESI): m/z 493 [M+H]$^+$.

Preparation of Intermediate 403-A-27: The synthetic method was similar to method 4-2 of EXAMPLE 4, except that 4-(1H-indol-1-yl)-5-(trifluoromethyl)pyrimidin-2-amine (205-5) therein was replaced by 4-(5-methoxy-1H-indol-1-yl)pyrimidin-2-amine (205-27). N$^1$-(2-(Dimethylamino)ethyl)-5-methoxy-N$^4$-(4-(5-methoxy-1H-indol-1-yl)pyrimidin-2-yl)-N$^1$-methylbenzene-1,2,4-triamine (Intermediate 403-A-27) was prepared. LCMS (ESI): m/z 462 [M+H]$^+$.

Preparation of Intermediate 403-A-28: The synthetic method was similar to that described in method 4-2 of EXAMPLE 4, except that 4-(1H-indol-1-yl)-5-(trifluoromethyl)pyrimidin-2-amine (205-5) therein was replaced by 4-(5-fluoro-1H-indol-1-yl)pyrimidin-2-amine (205-28). N$^1$-(2-(Dimethylamino)ethyl)-N$^4$-(4-(5-fluoro-1H-indol-1-yl)pyrimidin-2-yl)-5-methoxy-N$^1$-methylbenzene-1,2,4-triamine (Intermediate 403-A-28) was prepared. LCMS (ESI): m/z 450 [M+H]$^+$.

Preparation of Intermediate 403-A-29: The synthetic method was similar to method 4-2 of EXAMPLE 4, except that 4-(1H-indol-1-yl)-5-(trifluoromethyl)pyrimidin-2-amine (205-5) therein was replaced by 4-(6-fluoro-1H-indol-1-yl)pyrimidin-2-amine (205-29). N$^1$-(2-(Dimethylamino)ethyl)-N$^4$-(4-(6-fluoro-1H-indol-1-yl)pyrimidin-2-yl)-5-methoxy-N$^1$-methylbenzene-1,2,4-triamine (Intermediate 403-A-29) was prepared. LCMS (ESI): m/z 450 [M+H]$^+$.

Preparation of Intermediate 403-A-30: The synthetic method was similar to method 4-2 of EXAMPLE 4, except that 4-(1H-indol-1-yl)-5-(trifluoromethyl)pyrimidin-2- amine (205-5) therein was replaced by 4-(4-fluoro-1H-indol-1-yl)pyrimidin-2-amine (205-30). N$^1$-(2-(Dimethylamino)ethyl)-N$^4$-(4-(4-fluoro-1H-indol-1-yl)pyrimidin-2-yl)-5-methoxy-N$^1$-methylbenzene-1,2,4-triamine (Intermediate 403-A-30) was obtained. LCMS (ESI): m/z 450 [M+H]$^+$.

Preparation of Intermediate 403-A-31: The synthetic method was similar to method 4-2 of EXAMPLE 4, except that 4-(1H-indol-1-yl)-5-(trifluoromethyl)pyrimidin-2-amine (205-5) therein was replaced by 4-(5-chloro-1H-indol-1-yl)pyrimidin-2-amine (205-31). N$^1$-(2-(Dimethylamino)ethyl)-N$^4$-(4-(5-chloro-1H-indol-1-yl)pyrimidin-2-yl)-5-methoxy-N$^1$-methylbenzene-1,2,4-triamine (Intermediate 403-A-31) was prepared. LCMS (ESI): m/z 466 [M+H]$^+$.

Preparation of Intermediate 403-A-33: The synthetic method was similar to method 4-2 of EXAMPLE 4, except that 4-(1H-indol-1-yl)-5-(trifluoromethyl)pyrimidin-2-amine (205-5) therein was replaced by 1-(2-aminopyrimidin-4-yl)-1H-indole-5-carbonitrile (205-33). 1-(2-((5-Amino-4-((2-(dimethylamino)ethyl)(methyl)amino)-2-methoxyphenyl)amino) pyrimidin-4-yl)-1H-indole-5-carbonitrile (Intermediate 403-A-33) was prepared. LCMS (ESI): m/z 457 [M+H]$^+$.

Preparation of Intermediate 403-A-34: The synthetic method was similar to method 4-2 of EXAMPLE 4, except that 4-(1H-indol-1-yl)-5-(trifluoromethyl)pyrimidin-2-amine (205-5) therein was replaced by 4-(5-nitro-1H-indol-1-yl)pyrimidin-2-amine (205-34). N$^1$-(2-Dimethylaminoethyl)-5-methoxy-N$^1$-methyl-N$^4$-[4-(5-nitro-indol-1-yl)-pyrimidin-2-yl]-benzene-1,2,4-triamine (Intermediate 403-A-34) was prepared. LCMS (ESI): m/z 477 [M+H]$^+$.

Preparation of Intermediate 403-A-36: The synthetic method was similar to method 4-2 of EXAMPLE 4, except that 4-(1H-indol-1-yl)-5-(trifluoromethyl)pyrimidin-2-amine (205-5) therein was replaced by 4-(5-((tert-butyldiphenylsilyl)oxy)-1H-indol-1-yl)pyrimidin-2-amine (205-36). 1-(2-((5-Amino-4-((2-(dimethylamino)ethyl)(methyl)amino)-2-methoxyphenyl)amino)pyrimidin-4-yl)-1H-indol-5-ol (Intermediate 403-A-36) was prepared. LCMS (ESI): m/z 448 [M+H]$^+$.

Preparation of Intermediate 403-A-37: The synthetic method was similar to method 4-2 of EXAMPLE 4, except that 4-(1H-indol-1-yl)-5-(trifluoromethyl)pyrimidin-2-amine (205-5) therein was replaced by 4-(5-(2-((tert-butyldiphenylsilyl)oxy)ethoxy)-1H-indol-1-yl)pyrimidin-2-amine (205-37). N$^4$-(4-(5-(2-((tert-Butyldiphenylsilyl)oxy)ethoxy)-1H-indol-1-yl)pyrimidin-2-yl)-N$^1$-(2-(dimethylamino)ethyl)-5-methoxy-N$^1$-methylbenzene-1,2,4-triamine (Intermediate 403-A-37) was prepared. LCMS (ESI): m/z 730 [M+H]$^+$.

Preparation of Intermediate 403-A-38: The synthetic method was similar to method 4-2 of EXAMPLE 4, except that 4-(1H-indol-1-yl)-5-(trifluoromethyl)pyrimidin-2-amine (205-5) therein was replaced by 4-(5-(2-methoxyethoxy)-1H-indol-1-yl)pyrimidin-2-amine (205-38). N$^1$-(2-(Dimethylamino)ethyl)-5-methoxy-N$^4$-(4-(5-(2-methoxyethoxy)-1H-indol-1-yl)pyrimidin-2-yl)-N$^1$-methylbenzene-1,2,4-triamine (Intermediate 403-A-38) was obtained. LCMS (ESI): m/z 730 [M+H]$^+$.

Preparation of Intermediate 403-A-39: The synthetic method was similar to method 4-2 of EXAMPLE 4, except that 4-(1H-indol-1-yl)-5-(trifluoromethyl)pyrimidin-2-amine (205-5) therein was replaced by (1-(2-aminopyrimidin-4-yl)-1H-indol-5-yl)methanol (205-39). (1-(2-((5-Amino-4-((2-(dimethylamino)ethyl)(methyl)amino)-2-methoxyphenyl)amino)pyrimidin-4-yl)-1H-indol-5-yl) methanol (Intermediate 403-A-39) was prepared. LCMS (ESI): m/z 462 [M+H]$^+$.

Preparation of 403-A-41: Compound 1-(2-aminopyrimidin-4-yl)-1H-indole-5-carbonitrile (205-33) (120 mg, 0.51 mmol, 1.2 eq), compound N$^1$-(4-bromo-5-methoxy-2-nitrophenyl)-N$^1$,N$^2$,N$^2$-trimethylethane-1,2-diamine (105-A-1) (139.4 mg, 0.42 mmol, 1 eq), cesium carbonate (273 mg, 0.84 mmol, 2 eq), tris (dibenzylideneacetone) dipalladium (19 mg, 0.021 mmol, 0.05 eq) and 4,5-bisdiphenylphosphine-9,9-dimethylxanthene (21.85 mg, 0.038 mmol, 0.09 eq) were dissolved in toluene (20 mL), and heated to 110° C. and reacted for 6 hours under nitrogen protection. The reaction temperature was lowered to room temperature and the solvent was rotary evaporated. The residue was purified by silica gel column chromatography (dichloromethane/methanol=100/1) to give 1-(2-((4-((2-(dimethylamino)ethyl)(methyl)amino)-2-methoxy-5-nitrophenyl)amino)pyrimidin-4-yl)-1H-indole-5-carbonitrile (402-A-33) as a red solid (200 mg, yield: 98.03%). LCMS (ESI): m/z 487[M+H]$^+$. The compound obtained above (500 mg, 1.03 mmol, 1 eq) was dissolved in a mixed solvent of ethanol (10 mL) and dimethyl sulfoxide (1 mL), and then sodium hydroxide (1 ml, 1M aqueous solution) was added and stirred in an ice bath to mix well. Hydrogen peroxide (1 ml, 30% aqueous solution) was added dropwise slowly and stir continued for 5 minutes in an ice bath. The reaction was quenched with a saturated aqueous sodium sulfite solution, extracted with ethyl acetate and purified by silica gel column chromatography to give 1-(2-((4-((2-(dimethylamino)ethyl)(methyl)amino)-2-methoxy-5-nitrophenyl)amino)pyrimidin-4-yl)-1H-indole-5-carboxamide (402-A-41) (417 mg, yield: 80.3%). LCMS (ESI): m/z 505[M+H]$^+$. The compound obtained above (417 mg, 0.827 mmol, 1 eq) was dissolved in a mixed solvent of ethanol (30 mL) and aqueous ammonium chloride solution (3 mL) and heated to 60° C. Reduced iron powder (185 mg, 3.0 mmol, 4 eq) was added and the stir continued for 2 hours and then filtered. The filtrate was extracted with dichloromethane which was rotary evaporated to give the crude product which was purified by silica gel column chromatography to give 1-(2-((5-amino-4-((2-(dimethylamino)ethyl)(methyl)amino)-2-methoxyphenyl)amino)pyrimidin-4-yl)-1H-indole-5-carboxamide (403-A-41) (377 mg, 0.794 mmol, yield: 96.0%). LCMS (ESI): 475 m/z [M+H]$^+$.

Preparation of Intermediate 403-A-38: The synthetic method was similar to method 4-2 of EXAMPLE 4, except that 4-(1H-indol-1-yl)-5-(trifluoromethyl)pyrimidin-2-amine (205-5) therein was replaced by 4-(3-chloro-1H-indol-1-yl)pyrimidin-2-amine (205-46). N$^4$-(4-(3-Chloro-1H-indol-1-yl)pyrimidin-2-yl)-N$^1$-(2-(dimethylamino)ethyl)-5-methoxy-N$^1$-methylbenzene-1,2,4-triamine was prepared (Intermediate 403-A-46). LCMS (ESI): m/z 466 [M+H]$^+$.

Preparation of Intermediate 403-A-124: The synthetic method was similar to method 4-2 of EXAMPLE 4, except that 4-(1H-indol-1-yl)-5-(trifluoromethyl)pyrimidin-2-amine (205-5) therein was replaced by 4-(5-chloro-1H-pyrrolo[3,2-b]pyridin-1-yl)pyrimidin-2-amine (205-124). N$^4$-(4-(5-Chloro-1H-pyrrolo[3,2-b]pyridin-1-yl)pyrimidin-2-yl)-N$^1$-(2-(dimethylamino)ethyl)-5-methoxy-N$^1$-methylbenzene-1,2,4-triamine was prepared (Intermediate 403-A-124). LCMS (ESI): m/z 467 [M+H]$^+$.

Example 5: Preparation of Intermediate 506
(Prepared According to Scheme 5)

Intermediate 506 was prepared by one of the three methods, methods 5-1, 5-2 and 5-3, as described below:

Method 5-1: Prepared Through Intermediates 503 and 504.

Method 5-2 (Prepared Through Intermediates 503 and 106):

Step 5-2a: Preparation of 6-chloro-1-methyl-1H-benzo[d] imidazol-2(3H)-one (Intermediate 502-51): 5-Chloro-$N^1$-methylbenzene-1,2-diamine (501-51) (3.3 g, 21 mmol, 1.0 eq) was dissolved in dichloromethane (150 mL) and triethylamine (4.4 mL, 31.5 mmol, 1.5 eq) was added. The mixture temperature was lowered to 0° C. and triphosgene (2.6 g, 8.4 mmol, 0.4 eq) in dichloromethane (30 mL) was added dropwise slowly under nitrogen protection. The mixture was reacted for half an hour and then the pH of the reaction was adjusted to 7~8 by aqueous sodium carbonate. The solid was precipitated out which was filtered and dried to give the product 6-chloro-1-methyl-1H-benzo[d]imidazol-2(3H)-one (2.65 g, yield: 69%). LCMS (ESI): m/z 183[M+H]$^+$.

Step 5-2b: Preparation of 5-chloro-1-(2-chloropyrimidin-4-yl)-3-methyl-1H-benzo[d]imidazol-2(3H)-one (Intermediate 503-51): 6-Chloro-1-methyl-1H-benzo[d]imidazol-2(3H)-one (502-51) (500 mg, 2.7 mmol, 1.0 eq) and caesium carbonate (670 mg, 4.05 mmol, 1.5 eq) were mixed in N,N-dimethylformamide (70 mL), and then 2,4-dichloropyrimidine (410 mg, 2.7 mmol, 1.0 eq) was added under nitrogen protection and stifled at room temperature for 2 h. After the reaction was completed, a large amount of water was added and the solid was precipitated out which was filtered and dried to give the product 5-chloro-1-(2-chloropyrimidin-4-yl)-3-methyl-1H-benzo[d]imidazol-2(3H)-one (410 mg, yield: 50%). LCMS (ESI): m/z 295[M+H]$^+$.

Step 5-2c: Preparation of 5-chloro-1-(2-(4-((2-(dimethylamino)ethyl)(methyl)amino)-2-methoxy-5-nitrophenylamino)pyrimidin-4-yl)-3-methyl-1H-benzo[d]imidazol-2(3H)-one (Intermediate 505-A-51): 5-Chloro-1-(2-chloropyrimidin-4-yl)-3-methyl-1H-benzo[d]imidazol-2(3H)-one (503-51) (240 mg, 0.81 mmol, 1.0 eq), $N^1$-(2-(dimethylamino)ethyl)-5-methoxy-$N^1$-methyl-2-nitrobenzene-1,4-diamine (106-A-11) (216 mg, 0.81 mmol, 1.0 eq), caesium carbonate (528 mg, 1.62 mmol, 2.0 eq), tris(dibenzylideneacetone)dipalladium (40 mg, 0.04 mmol, 0.05 eq) and 9,9-dimethyl-4,5-bis(diphenylphosphino)xanthene (48 mg, 0.08 mmol, 0.1 eq) were mixed in toluene (50 mL). Under nitrogen protection, the reaction was placed in a preheated 110° C. oil bath and stirred to react for 3 hours. The mixture was concentrated under vacuo and purified by silica gel column chromatography (dichloromethane/methanol: 300:1~150:1) to give the product 5-chloro-1-(2-(4-((2-(dimethylamino)ethyl)(methyl)amino)-2-methoxy-5-nitrophenylamino)pyrimidin-4-yl)-3-methyl-1H-benzo[d]imidazol-2(3H)-one (150 mg, yield: 35%). LCMS (ESI): m/z 527[M+H]$^+$.

Step 5-2d: Preparation of 1-(2-(5-amino-4-((2-(dimethylamino)ethyl)(methyl)amino)-2-methoxyphenylamino)pyrimidin-4-yl)-5-chloro-3-methyl-1H-benzo[d]imidazol-2(3H)-one (Intermediate 506-A-51): 5-Chloro-1-(2-(4-((2-(dimethylamino)ethyl)(methyl)amino)-2-methoxy-5-nitrophenylamino)pyrimidin-4-yl)-3-methyl-1H-benzo[d]imidazol-2(3H)-one (505-A-51) (150 mg, 0.28 mmol, 1.0 eq) and ammonium chloride (126 mg, 2.38 mmol, 8.5 eq) were mixed in ethanol (30 mL) and water (7 mL) and heated to 50° C. Reduced iron powder (125 mg, 2.24 mmol, 8.0 eq) was added and the mixture was heated to 80° C. to react for 2 hours. After the reaction was completed, the mixture was filtered and the filtrate was concentrated which was extracted with dichloromethane. The organic phase was dried over anhydrous sodium sulfate and rotary evaporated in vacuo to leave a residue which was purified by silica gel column chromatography (dichloromethane/MeOH: 150:1~50:1) to give the product 1-(2-(5-amino-4-((2-(dimethylamino)ethyl)(methyl)amino)-2-methoxyphenylamino)pyrimidin-4-yl)-5-chloro-3-methyl-1H-benzo[d]imidazol-2(3H)-one (140 mg, yield: 99%). MS (ESI): m/z 497[M+H]$^+$.

The following Intermediates (506-A-52, 506-A-53, 506-A-57, 506-A-99, 506-A-133, 506-A-135) were prepared according to method 5-2, except that the Intermediate 503-51 therein was replaced by corresponding Intermediate 503.

Preparation of Intermediate 506-A-52: The synthetic method was similar to method 5-2 of EXAMPLE 5, except that compound 5-chloro-1-(2-chloropyrimidin-4-yl)-3-methyl-1H-benzo[d]imidazol-2(3H)-one (503-51) therein was replaced by 1-(2-chloropyrimidin-4-yl)-3-methyl-2-oxo-2,3-dihydro-1H-benzo[d]imidazole-5-carbonitrile (503-52). 1-(2-((5-Amino-4-((2-(dimethylamino)ethyl)(methyl)amino)-2-methoxyphenyl)amino)pyrimidin-4-yl)-3-methyl-2-oxo-2,3-dihydro-1H-benzo[d]imidazole-5-carbonitrile (Intermediate 506-A-52) was prepared. LCMS (ESI): m/z 488[M+H]$^+$.

Preparation of Intermediate 506-A-53: The synthetic method was similar to method 5-2 of EXAMPLE 5, except that compound 5-chloro-1-(2-chloropyrimidin-4-yl)-3-methyl-1H-benzo[d]imidazol-2(3H)-one (503-51) therein was replaced by 1-(2-chloropyrimidin-4-yl)-5-methoxy-3-methyl-1,3-dihydro-2H-benzo[d]imidazol-2-one (503-53). 1-(2-((5-Amino-4-((2-(dimethylamino)ethyl)(methyl)amino)-2-methoxyphenyl)amino)pyrimidin-4-yl)-5-methoxy-3-methyl-1H-benzo[d]imidazol-2(3H)-one (Intermediate 506-A-53) was prepared. LCMS (ESI): m/z 493[M+H]$^+$.

Preparation of Intermediate 506-A-57: The synthetic method was similar to method 5-2 of EXAMPLE 5, except that compound 5-chloro-1-(2-chloropyrimidin-4-yl)-3-methyl-1H-benzo[d]imidazol-2(3H)-one (503-51) therein was replaced by 1-(2-chloro-5-methoxypyrimidin-4-yl)-3-methyl-1,3-dihydro-2H-benzo[d]imidazol-2-one (503-57). 1-(2-((5-Amino-4-((2-(dimethylamino)ethyl)(methyl)amino)-2-methoxyphenyl)amino)-5-methoxypyrimidin-4-yl)-3-methyl-1H-benzo[d]imidazol-2(3H)-one (Intermediate 506-A-57) was prepared. LCMS (ESI): m/z 493[M+H]$^+$.

Preparation of Intermediate 506-A-99: The synthetic method was similar to method 5-2 of EXAMPLE 5, except that compound 5-chloro-1-(2-chloropyrimidin-4-yl)-3-methyl-1H-benzo[d]imidazol-2(3H)-one (503-51) therein was replaced by 5-chloro-1-(2-chloropyrimidin-4-yl)-3-cyclopropyl-1,3-dihydro-2H-benzo[d]imidazol-2-one (503-99). 1-(2-((5-Amino-4-((2-(dimethylamino)ethyl)(methyl)amino)-2-methoxyphenyl)amino)pyrimidin-4-yl)-5-chloro-3-cyclopropyl-1,3-dihydro-2H-benzo[d]imidazol-2-one (Intermediate 506-A-99) was prepared. LCMS (ESI): m/z 523[M+H]$^+$.

Preparation of Intermediate 506-A-133: The synthetic method was similar to method 5-2 of EXAMPLE 5, except that compound 5-chloro-1-(2-chloropyrimidin-4-yl)-3-methyl-1H-benzo[d]imidazol-2(3H)-one (503-51) therein was replaced by 1-(2-chloro-5-methoxypyrimidin-4-yl)-3-isopropyl-benzo[d]imidazol-2(3H)-one (503-133). 1-(2-((4-((2-(Dimethylamino)ethyl)(methyl)amino)-2-methoxy-5-aminophenyl)amino)-5-methoxypyrimidin-4-yl)-3-isopropyl-1H-benzo[d]imidazol-2(3H)-one (Intermediate 506-A-133) was obtained. LCMS (ESI): m/z 521[M+H]$^+$.

Preparation of Intermediate 506-A-135: The synthetic method was similar to method 5-2 of EXAMPLE 5, except that compound 5-chloro-1-(2-chloropyrimidin-4-yl)-3-methyl-1H-benzo[d]imidazol-2 (3H)-one (503-51) therein was replaced by 1-(2-chloro-5-(dimethylamino)pyrimidin-4-yl)-3-isopropyl-1,3-dihydro-2H-benzo[d]imidazol-2-one (503-135). 1-(2-((5-Amino-4-((2-(dimethylamino)ethyl)(methyl)amino)-2-methoxyphenyl) amino)-5-(dimethylamino)pyrimidin-4-yl)-3-isopropyl-1,3-dihydro-2H-benzo[d]imidazol-2-one (Intermediate 506-A-135) was prepared. LCMS (ESI): m/z 534[M+H]$^+$.

Method 5-3: (Prepared Through Intermediates 503 and 103):

Step 5-3a: Preparation of 1-(3-methylbut-2-enyl)-1H-benzo[d]imidazol-2(3H)-one (Intermediate 502-62): o-Nitroaniline (5 g, 36 mmol, 1.0 eq) was dissolved in N-methylpyrrolidone (100 mL) and to it was added cesium carbonate (23 g, 72 mmol, 2.0 eq). 1-Bromo-3-methyl-2-butene (7 g, 46.8 mmol, 1.3 eq) was then added dropwise to the above mixture and heated to 100° C. to react overnight. The reaction was quenched with water, extracted with ethyl acetate which was then washed with saturated brine several times. The organic phase was dried over anhydrous sodium sulfate, concentrated in vacuo to give a yellow oil which was finally purified by silica gel column chromatography (ethyl acetate/petroleum ether=1/5~1/3) to give the product N$^1$-(3-methyl-2-butene) benzene-1,2-diamine (501-62) (3 g, yield: 40%). LCMS (ESI): m/z 207[M+H]$^+$.

Compound 501-62 (1.28 g, 7.2 mmol, 1.0 eq) was dissolved in tetrahydrofuran (100 mL) and to it was added triethylamine (1.5 mL, 10.8 mmol, 1.5 eq). Under nitrogen protection, N,N'-carbonyldiimidazole (3.5 g, 21.6 mmol, 3.0 eq) was added and the mixture was heated to 50° C. to react overnight. After the reaction was completed, the mixture was extracted with dichloromethane which was then concentrated in vacuo and purified by silica gel column chromatography (dichloromethane/methanol=200/1~100/1) to give 1-(3-methylbut-2-enyl)-1H-benzo[d]imidazol-2(3H)-one (1.3 g, yield: 89%). LCMS (ESI): m/z 203[M+H]$^+$.

Step 5-3b: Preparation of 1-(2-chloropyrimidin-4-yl)-3-(3-methylbut-2-enyl)-1H-benzo[d]imidazol-2 (3H)-one (Intermediate 503-62): 1-(3-Methyl-2-butene)-1H-benzo[d]imidazol-2(3H)-one (502-62) (600 mg, 2.97 mmol, 1.0 eq) and cesium carbonate (1.93 g, 5.94 mmol, 2.0 eq) were mixed in N, N-dimethylformamide (10 mL). Under nitrogen protection, 2,4-dichloropyrimidine (659 mg, 4.45 mmol, 1.5 eq) was added and stirred to react at room temperature for 2 h. After the reaction was completed, a large amount of water was added and the solid was precipitated out which was filtered and dried to give the product 1-(2-chloropyrimidin-4-yl)-3-(3-methylbut-2-enyl)-1H-benzo[d]imidazol-2(3H)-one (755 mg, yield: 81%). LCMS (ESI): m/z 315[M+H]$^+$.

Step 5-3c: Preparation of 1-(2-(4-((2-(dimethylamino) ethyl)(methyl)amino)-2-methoxy-5-nitrophenylamino)pyrimidin-4-yl)-3-(3-methylbut-2-enyl)-1H-benzo[d]imidazol-2 (3H)-one (Intermediate 505-A-62): 1-(2-Chloropyrimidin-4-yl)-3-(3-methylbut-2-enyl)-1H-benzo[d]imidazol-2(3H)-one (350 mg, 1.27 mmol, 1.0 eq) and 4-fluoro-2-methoxy-5-nitroaniline (103) (261 mg, 1.4 mmol, 1.3 eq) were mixed in isopropanol (60 mL) and then concentrated hydrochloric acid (1.5 mL) was added. The mixture was stirred and reacted at 100° C. overnight. After the reaction was completed, the temperature was lowered to room temperature and concentration was performed in vacuo to give a yellow solid. The solid obtained was dissolved in ethyl acetate, and then a saturated sodium carbonate solution was added to neutralize the remaining acid. The organic phase was concentrated in vacuo and recrystallized from petroleum ether/ethyl acetate (10/1) to give a yellow solid (213 mg, yield: 41%). LCMS (ESI): m/z 465 [M+H]$^+$. The compound obtained above (213 mg, 0.458 mmol, 1.0 eq) was dissolved in tetrahydrofuran (30 mL) and then N, N, N-trimethylethylenediamine (140 mg, 1.37 mmol, 3.0 eq) and N, N-diisopropylethylamine (177 mg, 1.37 mmol, 3.0 eq) were added to the system. The reaction was stirred at 80° C. overnight. After the reaction was completed, the temperature was lowered to room temperature and then extraction was performed with ethyl acetate and water. The organic phase was washed with water and saturated brine several times. The organic phase was dried over anhydrous sodium sulfate and concentrated in vacuo and purified by silica gel column chromatography (dichloromethane/methanol=200/1~100/1) to give the product 1-(2-(4-((2-(dimethylamino)ethyl)(methyl)amino)-2-methoxy-5-nitrophenylamino)pyrimidin-4-yl)-3-(3-methylbut-2-enyl)-1H-benzo[d]imidazol-2 (3H)-one as a red solid (132 mg, yield: 52%). LCMS (ESI): m/z 547[M+H]$^+$.

Step 5-3d: Preparation of 1-(2-(5-amino-4-((2-(dimethylamino) ethyl)(methyl)amino)-2-methoxyphenylamino)pyrimidin-4-yl)-3-(3-methylbut-2-enyl)-1H-benzo[d]imidazol-2 (3H)-one (Intermediate 506-A-62): 1-(2-(4-((2-(Dimethylamino)ethyl)(methyl)amino)-2-methoxy-5-nitrophenylamino)pyrimidin-4-yl)-3-(3-methylbut-2-enyl)-1H-benzo[d]imidazol-2 (3H)-one (505-A-62) (132 mg, 0.24 mmol, 1.0 eq) and ammonium chloride (108 mg, 2.04 mmol, 8.5 eq) were mixed in ethanol (40 mL) and water (10 mL) and heated to 50° C. Reduced iron powder (108 mg, 1.92 mmol, 8.0 eq) was then added and the mixture was heated to 80° C. to react for 2 hours. After the reaction was completed, it was filtered and the filtrate was concentrated and extracted with dichloromethane. The organic phase was dried over anhydrous sodium sulfate, rotary evaporated in vacuo and purified by silica gel column chromatography (dichloromethane/methanol=200/1~50/1) to give the product 1-(2-(5-amino-4-((2-(dimethylamino) ethyl)(methyl)amino)-2-methoxyphenylamino)pyrimidin-4-yl)-3-(3-methylbut-2-enyl)-1H-bezo[d]imidazol-2(3H)-one (110 mg, yield: 88%). LCMS (ESI): m/z 517[M+H]$^+$.

The following Intermediates (506-A-50, 506-A-63, 506-A-91, 506-A-98, 506-A-101, 506-A-102, 506-A-105, 506-A-118, 506-A-120, 506-A-125, 506-A-127, 506-A-128, 506-A-132, 506-A-138, 506-A-139) were prepared according to method 5-3, except that the Intermediate 502-62 therein was replaced by corresponding Intermediate 502.

Preparation of Intermediate 506-A-50: The synthetic method was similar to method 5-3 of EXAMPLE 5, except that compound 1-(3-methylbut-2-enyl)-1H-benzo[d]imidazol-2(3H)-one (502-62) therein was replaced by 6-fluoro-1-methyl-1H-benzo[d]imidazol-2(3H)-one (502-50). 1-(2-((5-Amino-4-((2-(dimethylamino) ethyl)(methyl)amino)-2-methoxyphenyl)amino)pyrimidin-4-yl)-5-fluoro-3-methyl-1,3-dihydro-2H-benzo[d]imidazol-2-one (Intermediate 506-A-50) was prepared. LCMS (ESI): m/z 481 [M+H]$^+$.

Preparation of Intermediate 506-A-62: The synthetic method was similar to method 5-3 of EXAMPLE 5, except that compound 1-(3-methylbut-2-enyl)-1H-benzo[d]imidazol-2(3H)-one (502-62) therein was replaced by 1-(3-methylbut-2-enyl)-1H-benzo[d]imidazol-2(3H)-one (502-62). 1-(2-(5-Amino-4-((2-(dimethylamino) ethyl)(methyl)amino)-2-methoxyphenylamino)pyrimidin-4-yl)-3-(3-methylbut-2-enyl)-1H-benzo[d]imidazol-2(3H)-one (Intermediate 506-A-62) was prepared. LCMS (ESI): m/z 517 [M+H]$^+$.

Preparation of Intermediate 506-A-63: The synthetic method was similar to method 5-3 of EXAMPLE 5, except that compound 1-(3-methylbut-2-enyl)-1H-benzo[d]imidazol-2(3H)-one (502-62) therein was replaced by 1-cyclopropylmethyl-1,3-dihydro-2H-benzo[d]imidazol-2-one (502-

63). 1-(2-((5-Amino-4-((2-(dimethylamino)ethyl) (methyl) amino)-2-methoxyphenyl)amino)pyrimidin-4-yl)-3-(cyclopropylmethyl)-1,3-dihydro-2H-benzo[d]imidazol-2-one (Intermediate 506-A-63) was prepared. LCMS (ESI): m/z 503 [M+H]$^+$.

Preparation of Intermediate 506-A-91: The synthetic method was similar to method 5-3 of EXAMPLE 5, except that compound 1-(3-methylbut-2-enyl)-1H-benzo[d]imidazol-2(3H)-one (502-62) therein was replaced by 6-fluoro-1-isopropyl-1,3-dihydro-2H-benzo[d]imidazol-2 (3H)-one (502-91). 1-(2-(5-Amino-4-((2-(dimethylamino)ethyl) (methyl)amino)-2-methoxyphenylamino)pyrimidin-4-yl)-5-fluoro-3-isopropyl-1H-benzo[d]imidazol-2(3H)-one (Intermediate 506-A-91) was obtained. LCMS (ESI): m/z 509 [M+H]$^+$.

Preparation of Intermediate 506-A-98: The synthetic method was similar to method 5-3 of EXAMPLE 5, except that compound 1-(3-methylbut-2-enyl)-1H-benzo[d]imidazol-2(3H)-one (502-62) therein was replaced by 1-cyclopropyl-6-fluoro-1H-benzo[d]imidazol-2(3H)-one (502-98). 1-(2-(5-Amino-4-((2-(dimethylamino)ethyl) (methyl) amino)-2-methoxyphenylamino)pyrimidin-4-yl)-3-cyclopropyl-5-fluoro-1H-benzo[d]imidazol-2(3H)-one (Intermediate 506-A-98) was prepared. LCMS (ESI): m/z 507 [M+H]$^+$.

Preparation of Intermediate 506-A-101: The synthetic method was similar to method 5-3 of EXAMPLE 5, except that compound 1-(3-methylbut-2-enyl)-1H-benzo[d]imidazol-2(3H)-one (502-62) therein was replaced by 3-cyclopropyl-2-oxo-2,3-dihydro-1H-benzo[d]imidazole-5-cyano (502-101). 1-(2-((5-Amino-4-((2-(dimethylamino)ethyl) (methyl)amino)-2-methoxyphenyl)amino)pyrimidin-4-yl)-3-cyclopropyl-2-oxo-2,3-dihydro-1H-benzo[d]imidazole-5-carbonitrile (Intermediate 506-A-101) was prepared. LCMS (ESI): m/z 514 [M+H]$^+$.

Preparation of Intermediate 506-A-102: The synthetic method was similar to method 5-3 of EXAMPLE 5, except that compound 1-(3-methylbut-2-enyl)-1H-benzo[d]imidazol-2(3H)-one (502-62) therein was replaced by 1-cyclopropyl-6-methoxy-1H-benzo[d]imidazol-2 (3H)-one (502-102). 1-(2-((5-Amino-4-((2-(dimethylamino)ethyl)(methyl)amino)-2-methoxyphenyl)amino)pyrimidin-4-yl)-3-cyclopropyl-5-methoxy-1,3-dihydro-2H-benzo[d]imidazol-2-one (Intel mediate 506-A-102) was obtained. LCMS (ESI): m/z 519 [M+H]$^+$.

Preparation of Intermediate 506-A-105: The synthetic method was similar to method 5-3 of EXAMPLE 5, except that compound 1-(3-methylbut-2-enyl)-1H-benzo[d]imidazol-2(3H)-one (502-62) therein was replaced by 1-cyclopropylmethyl-6-fluoro-1,3-dihydro-2H-benzo[d]imidazol-2 (3H)-one (502-105). 1-(2-(5-amino-4-((2-(dimethylamino)ethyl)(methyl)amino)-2-methoxyphenylamino)pyrimidin-4-yl)-3-(cyclopropylmethyl)-5-fluoro-1H-benzo[d]imidazol-2 (3H)-one (Intermediate 506-A-105) was prepared. LCMS (ESI): m/z 521 [M+H]$^+$.

Preparation of Intermediate 506-A-118 (the synthetic method was similar to method 5-3 of EXAMPLE 5): 4-Fluoro-2-methyl-5-nitroaniline (103-118) (340 mg, 2.0 mmol, 1.0 eq), 1-(2-chloropyrimidin-4-yl)-3-methyl-1H-benzo[d]imidazol-2 (3H)-one (600 mg, 2.3 mmol, 1.15 eq) and concentrated hydrochloric acid (5 mL, 59.0 mmol, 29.5 eq) were added to isopropanol (100 mL) and then reacted at 100° C. overnight. The temperature was lowered to room temperature and neutralization was performed with a saturated aqueous sodium carbonate solution. The mixture was then extracted with ethyl acetate which was then washed with water and saturated brine, dried over anhydrous sodium sulfate, concentrated in vacuo and purified by silica gel column chromatography (eluent: ethyl acetate/petroleum ether=1/1) to give 1-(2-(4-fluoro-2-methyl-5-nitroanilino) pyrimidin-4-yl)-3-methyl-1, 3-dihydro-2H-benzo[d]imidazole-2-one as a white solid (120 mg, yield: 15%). LCMS (ESI): m/z 395[M+H]$^+$. The solid obtained above (120 mg, 0.3 mmol, 1.0 eq), N, N, N'-trimethyl-1,2-ethanediamine (0.08 mL, 0.6 mmol, 2.0 eq) and diisopropylethylamine (0.1 mL, 0.6 mmol, 2.0 eq) were added into tetrahydrofuran (30 mL), and heated to reflux and stirred overnight. The reaction temperature was lowered to room temperature and concentration was performed in vacuo. The residue was dissolved in ethyl acetate which was then washed with water and brine, dried over anhydrous sodium sulfate and concentrated in vaccuo to give 1-(2-(4-((2-dimethylamino)ethyl) (methyl) amino)-2-methyl-5-nitrophenylamino) pyrimidin-4-yl)-3-methyl-1,3-dihydro-2H-benzo[d]imidazol-2-one (505-A-118) as a red solid (140 mg, yield: 98.6%). LCMS (ESI): m/z 476[M+H]$^+$. The solid obtained above (140 mg, 0.3 mmol, 1.0 eq) and ammonium chloride (128 mg, 2.4 mmol, 8.0 eq) were added to a mixed liquid of ethanol (30 mL) and water (6 mL) and heated to 65° C. Reduced iron powder (143 mg, 2.4 mmol, 8.5 eq) was then added in portions. The mixture was heated to reflux to react for 1 hour. The reaction temperature was lowered to room temperature and dichloromethane was added and filtered. The filtrate was washed with water and brine. The organic phase was dried over anhydrous sodium sulfate, concentrated in vacuo and purified by silica gel column chromatography (eluent: dichloromethane/methanol=40/1~15/1) to give 1-(2-(5-amino-4-((2-dimethylamino)ethyl) (methyl) amino)-2-methylphenylamino) pyrimidin-4-yl)-3-methyl-1,3-dihydro-2H-benzo[d]imidazol-2-one (506-A-118) (72 mg, yield: 54%). LCMS (ESI): m/z 446[M+H]$^+$.

Preparation of Intermediate 506-A-120: The synthetic method was similar to method 5-3 of EXAMPLE 5 for the preparation of Intermediate 506-A-118, except that compound 4-fluoro-2-methyl-5-nitroaniline (103-118) therein was replaced by 4-fluoro-2-(2-methoxy-ethoxy)-5-nitroaniline (103-120). 1-{2-[5-Amino-4-[(2-dimethylamino-ethyl)-methyl-amino]-2-(2-methoxy-ethoxy)-phenyl amino]-pyrimidin-4-yl}-3-methyl-1,3-dihydro-benzoimidazol-2-one (Intermediate 506-A-120) was prepared. LCMS (ESI): m/z 507 [M+H]$^+$.

Preparation of Intermediate 506-A-125: The synthetic method was similar to method 5-3 of EXAMPLE 5 for the preparation of Intermediate 506-A-118, except that compound 4-fluoro-2-methyl-5-nitroaniline (103-118) therein was replaced by 4-fluoro-3-nitroaniline (103-125). 1-(2-((3-Amino-4-((2-(dimethylamino)ethyl)(methyl) amino)phenyl)amino) pyrimidin-4-yl)-3-methyl-1,3-dihydro-2H-benzo[d]imidazol-2-one (Intermediate 506-A-125) was prepared. LCMS (ESI): m/z 433 [M+H]$^+$.

Preparation of Intermediate 506-A-127: The synthetic method was similar to method 5-3 of EXAMPLE 5 for the preparation of Intermediate 506-A-118, except that compound 1-(2-Chloropyrimidin-4-yl)-3-methyl-1H-benzo[d]imidazol-2(3H)-one therein was replaced by 1-(2-Chloropyrimidin-4-yl)-3-isopropyl-1,3-dihydro-2H-benzo[d]imidazol-2-one. 1-(2-((5-Amino-4-((2-(dimethylamino) ethyl)(methyl)amino)-2-methylphenyl)amino)pyrimidin-4-yl)-3-isopropyl-1,3-dihydro-2H-benzo[d]imidazol-2-one (Intermediate 506-A-127) was prepared. LCMS (ESI): m/z 475 [M+H]$^+$.

Preparation of Intermediate 506-A-128: The synthetic method was similar to method 5-3 of EXAMPLE 5 for the preparation of Intermediate 506-A-125, except that compound 1-(2-Chloropyrimidin-4-yl)-3-methyl-1H-benzo[d]imidazol-2 (3H)-one therein was replaced by 1-(2-Chloropyrimidin-4-yl)-3-isopropyl-1,3-dihydro-2H-benzo[d]imidazol-2-one. 1-(2-((4-((2-(Dimethylamino)ethyl)(methyl)amino)-3-aminophenyl)amino)pyrimidin-4-yl)-3-isopropyl-1H-benzo[d]imidazol-2 (3H)-one (Intermediate 506-A-128) was prepared. LCMS (ESI): m/z 461 [M+H]$^+$.

Preparation of Intermediate 506-A-132: The synthetic method was similar to method 5-3 of EXAMPLE 5 for the preparation of Intermediate 506-A-125, except that compound 4-fluoro-3-nitroaniline (103-125) therein was replaced by 4-fluoro-2-isopropyl-5-nitroaniline (103-132). 1-(2-((5-Amino-4-((2-(dimethylamino)ethyl)(methyl)amino)-2-isopropylphenyl)amino)pyrimidin-4-yl)-3-methyl-1,3-dihydro-2H-benzo[d]imidazol-2-one (Intermediate 506-A-132 was obtained. LCMS (ESI): m/z 475 [M+H]$^+$.

Preparation of Intermediate 506-A-138: The synthetic method was similar to method 5-3 of EXAMPLE 5, except that compound 1-(3-methylbut-2-enyl)-1H-benzo[d]imidazol-2(3H)-one (502-62) therein was replaced by compound 1-isopropyl-6-methoxy-1H-benzo[d]imidazol-2(3H)-one (502-138). 1-(2-((4-((2-(Dimethylamino)ethyl)(methyl)amino)-2-methoxy-5-aminophenyl)amino)pyrimidin-4-yl)-3-isopropyl-5-methoxy-1H-benzo[d]imidazol-2 (3H)-one (Intermediate 506-A-138) was obtained. LCMS (ESI): m/z 521 [M+H]$^+$.

Preparation of Intermediate 506-A-138: The synthetic method was similar to method 5-3 of EXAMPLE 5, except that compound 1-(3-methylbut-2-enyl)-1H-benzo[d]imidazol-2(3H)-one (502-62) therein was replaced by compound 1-(2-chloropyrimidin-4-yl)-5-hydroxy-3-isopropyl-1H-benzo[d]imidazol-2 (3H) (502-139). 1-(2-((4-((2-(Dimethylamino)ethyl)(methyl)amino)-2-methoxy-5-aminophenyl)amino)pyrimidin-4-yl)-5-hydroxy-3-isopropyl-1H-benzo[d]imidazol-2(3H)-one (Intermediate 506-A-139) was obtained. LCMS (ESI): m/z 507 [M+H]$^+$.

Example 6: Preparation of N-(5-((4-(1H-indol-1-yl)-5-(trifluoromethyl) pyrimidin-2-yl) amino)-2-((2-(dimethylamino)ethyl)(methyl)amino)-4-methoxyphenyl)acrylamide (Compound 5) (Prepared According to Scheme 6)

N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) (90 mg, 0.26 mmol, 1.0 eq), triethylamine (0.09 mL, 0.65 mmol, 2.5 eq), HATU (118 mg, 0.31 mmol, 1.2 eq) and acrylic acid (602-3) (23 mg, 0.31 mmol, 1.2 eq) were added into dichloromethane (15 mL) and stirred for 0.5 hour at room temperature. The stirring was then stopped when the reaction was stopped and a saturated aqueous sodium carbonate solution was added and partitioned. The aqueous phase was extracted with dichloromethane twice. The organic phase was combined and washed with diluted aqueous hydrochloric acid and saturated brine in sequence, dried, concentrated in vacuo and purified by prep-TLC (eluent: dichloromethane/methanol 25: 1) to give N-(5-((4-(1H-indol-1-yl)-5-(trifluoromethyl)pyrimidin-2-yl)amino)-2-((2-(dimethylamino)ethyl)(methyl)amino)-4-methoxyphenyl)acrylamide as a light yellow solid (25 mg, yield: 17%).

The characterization data of Compound 5 were: LCMS (ESI): m/z 554 [M+H]$^+$; m.p.: 161-162° C.; $^1$H NMR (500 MHz, DMSO-d6) δ 9.98 (s, 1H), 9.61 (s, 1H), 8.86 (s, 1H), 8.32 (s, 1H), 7.71 (s, 1H), 7.58 (s, 1H), 7.48 (s, 1H), 7.11 (s, 2H), 7.00 (s, 1H), 6.73 (s, 1H), 6.42 (s, 1H), 6.23 (d, J=16.9 Hz, 1H), 5.75 (d, J=9.9 Hz, 1H), 3.79 (s, 3H), 2.87 (s, 2H), 2.69 (s, 3H), 2.21 (s, 8H).

Example 7: Preparation of N-(5-((4-(1H-indol-1-yl)-5-methoxypyrimidin-2-yl)amino)-2-((2-(dimethylamino)ethyl)(methyl)amino)-4-methoxyphenyl)acrylamide (Compound 6) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(4-(1H-indol-1-yl)-5-methoxypyrimidin-2-yl)-N$^1$-(2-(dimethylamino)ethyl)-5-methoxy-N$^1$-methylbenzene-1,2,4-triamine (403-A-6) (270 mg, 0.58 mmol, 1.0 eq). N-(5-((4-(1H-Indol-1-yl)-5-methoxypyrimidin-2-yl)amino)-2-((2-(dimethylamino)ethyl)(methyl)amino)-4-methoxyphenyl)acrylamide was obtained as a beige solid (35 mg, yield: 12%).

The characterization data of the Compound 6 were: LCMS (ESI): m/z 516 [M+H]$^+$. m.p.: 143.3-147.8° C.; $^1$H NMR (500 MHz, DMSO-d6) δ 10.09 (s, 1H), 8.64 (s, 1H), 8.45 (s, 1H), 8.22 (s, 1H), 8.00 (d, J=19.9 Hz, 2H), 7.57 (s, 1H), 7.11 (s, 2H), 7.01 (s, 1H), 6.70 (s, 1H), 6.38 (m, 1H), 6.21 (d, J=16.6 Hz, 1H), 5.74 (d, J=9.2 Hz, 1H), 3.83 (d, J=34.2 Hz, 6H), 2.86 (s, 2H), 2.71 (s, 3H), 2.29 (s, 2H), 2.19 (s, 6H).

Example 8: Preparation of N-(5-((4-(1H-indol-1-yl)-5-methylpyrimidin-2-yl) amino)-2-((2-(dimethylamino)ethyl)(methyl)amino)-4-methoxyphenyl)acrylamide (Compound 8) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(4-(1H-indol-1-yl)-5-methylpyrimidin-2-yl)-N$^1$-(2-(dimethylamino)ethyl)-5-methoxy-N$^1$-methylbenzene-1,2,4-triamine (99 mg, 0.22 mmol, 1.0 eq). N-(5-((4-(1H-Indol-1-yl)-5-methylpyrimidin-2-yl) amino)-2-((2-(dimethylamino)ethyl)(methyl)amino)-4-methoxyphenyl)acrylamide was obtained as a beige solid (60 mg, yield: 54.5%).

The characterization data of Compound 8 were: LCMS (ESI): m/z 500 [M+H]$^+$. $^1$H NMR (500 MHz, DMSO-d6) δ 9.99 (s, 1H), 8.61 (s, 1H), 8.46 (s, 1H), 8.32 (s, 1H), 7.74 (d, J=3.4 Hz, 1H), 7.68 (d, J=7.3 Hz, 1H), 7.60 (dd, J=6.3, 2.4 Hz, 1H), 7.11 (m, 2H), 6.98 (s, 1H), 6.69 (d, J=3.3 Hz, 1H), 6.39 (dd, J=16.8, 10.1 Hz, 1H), 6.23 (dd, J=16.9, 1.8 Hz, 1H), 5.74 (m, 1H), 3.80 (s, 3H), 2.86 (s, 2H), 2.67 (d, J=9.8 Hz, 3H), 2.30 (s, 2H), 2.20 (s, 6H), 2.17 (s, 3H).

Example 9: Preparation of N-(5-(5-(dimethylamino)-4-(1H-indol-1-yl)pyrimidin-2-ylamino)-2-((2-(dimethylamino)ethyl)(methyl)amino)-4-methoxyphenyl)acrylamide (Compound 10) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(5-(dimethylamino)-4-(1H-indol-1-yl)pyrimidin-2-yl)-N$^1$-(2-(dimethylamino)ethyl)-5-methoxy-N$^1$-methylbenzene-1,2,4-triamine (403-A-10) (216 mg, 0.4695 mmol, 1.0 eq). N-(5-(5-(Dimethylamino)-4-(1H-indol-1-yl)pyrimidin-2-ylamino)-2-((2-(dimethylamino)ethyl)(methyl)amino)-4-methoxyphenyl)acrylamide was obtained as a yellow solid (60 mg, yield: 19.2%).

The characterization data of Compound 10 were: LCMS (ESI): m/z 529 [M+H]±; m.p.: 154-155° C.; $^1$H NMR (500 MHz, DMSO-d6) δ 10.03 (s, 1H), 8.69 (s, 1H), 8.38 (s, 1H), 8.13 (m, 2H), 7.87 (dd, J=6.0, 3.3 Hz, 1H), 7.57 (m, 1H), 7.10 (m, 2H), 6.98 (s, 1H), 6.69 (d, J=3.5 Hz, 1H), 6.39 (dd, J=16.9, 10.1 Hz, 1H), 6.23 (dd, J=16.9, 1.8 Hz, 1H), 5.74 (dd, J=8.7, 3.0 Hz, 1H), 3.81 (s, 3H), 2.86 (s, 2H), 2.69 (s, 3H), 2.47 (s, 6H), 2.29 (s, 2H), 2.20 (s, 6H).

Example 10: Preparation of N-(5-(4-(1H-indol-1-yl)-5-(methylamino)pyrimidin-2-ylamino)-2-((2-(dimethylamino)ethyl)(methyl)amino)-4-methoxyphenyl)acrylamide (Compound 11) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(4-(1H-indol-1-yl)-5-(methylamino)pyrimidin-2-yl)-N$^1$-(2-(dimethylamino)ethyl)-5-methoxy-N$^1$-methylbenzene-1,2,4-triamine (403-A-11) (216 mg, 0.4695 mmol, 1.0 eq). N-(5-(4-(1H-Indol-1-yl)-5-(methylamino)pyrimidin-2-ylamino)-2-((2-(dimethylamino)ethyl)(methyl)amino)-4-methoxyphenyl)acrylamide was obtained as a yellow solid (30 mg, yield: 12.4%).

The characterization data of Compound 11 were: LCMS (ESI): m/z 515 [M+H]$^+$; m.p.: 154-156° C.; $^1$H NMR (500 MHz, DMSO-d6) δ 10.03 (s, 1H), 8.85 (s, 1H), 8.17 (s, 1H), 7.85 (d, J=3.4 Hz, 1H), 7.61 (m, 3H), 7.14 (dt, J=19.9, 7.0 Hz, 2H), 6.95 (s, 1H), 6.71 (d, J=3.3 Hz, 1H), 6.38 (dd, J=16.9, 10.1 Hz, 1H), 6.24 (d, J=15.6 Hz, 1H), 5.74 (m, 1H), 4.70 (m, 1H), 3.81 (d, J=8.3 Hz, 3H), 2.85 (s, 2H), 2.68 (m, 6H), 2.26 (s, 2H), 2.19 (s, 6H).

Example 11: Preparation of N-(2-((2-(dimethylamino)ethyl)(methyl)amino)-4-methoxy-5-((4-(5-methoxy-1H-indol-1-yl)pyrimidin-2-yl)amino)phenyl)acrylamide (Compound 27) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^1$-(2-(dimethylamino)ethyl)-5-methoxy-N$^4$-(4-(5-methoxy-1H-indol-1-yl)pyrimidin-2-yl)-N$^1$-methylbenzene-1,2,4-triamine (403-A-27) (100 mg, 0.206 mmol, 1.0 eq). N-(2-((2-(Dimethylamino)ethyl)(methyl)amino)-4-methoxy-5-((4-(5-methoxy-1H-indol-1-yl)pyrimidin-2-yl)amino)phenyl)acrylamide was obtained as a yellow solid (67 mg, yield: 59.98%).

The characterization data of Compound 27 were: LCMS (ESI): m/z 516 [M+H]$^+$. m.p.: 117-118° C.; $^1$H NMR (500 MHz, DMSO-d6) δ 10.06 (s, 1H), 8.55 (d, J=12.9 Hz, 2H), 8.33 (m, 2H), 8.09 (s, 1H), 7.07 (m, 3H), 6.67 (d, J=11.2 Hz, 2H), 6.40 (dd, J=16.2, 11.0 Hz, 1H), 6.19 (d, J=16.9 Hz, 1H), 5.72 (d, J=10.0 Hz, 1H), 3.76 (s, 6H), 2.92 (s, 2H), 2.75 (d, J=1.8 Hz, 3H), 2.34 (s, 2H), 2.21 (s, 6H).

Example 12: Preparation of N-(2-((2-(dimethylamino)ethyl)(methyl)amino)-5-((4-(5-fluoro-1H-indol-1-yl)pyrimidin-2-yl)amino)-4-methoxyphenyl)acrylamide (Compound 28) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^1$-(2-(dimethylamino)ethyl)-N$^4$-(4-(5-fluoro-1H-indol-1-yl)pyrimidin-2-yl)-5-methoxy-N$^1$-methylbenzene-1,2,4-triamine (403-A-28) (400 mg, 0.9 mmol, 1.0 eq). N-(2-((2-(Dimethylamino)ethyl)(methyl)amino)-5-((4-(5-fluoro-1H-indol-1-yl)pyrimidin-2-yl)amino)-4-methoxyphenyl)acrylamide was obtained as a yellow solid (230 mg, yield: 51%).

The characterization data of Compound 28 were: LCMS (ESI): m/z 504 [M+H]$^+$. m.p.: 168-170° C.; $^1$H NMR (500 MHz, DMSO-d6) δ 10.04 (s, 1H), 8.65 (s, 1H), 8.51 (s, 1H), 8.41 (m, 2H), 8.20 (s, 1H), 7.37 (d, J=7.7 Hz, 1H), 7.12 (d, J=4.9 Hz, 1H), 7.06 (s, 1H), 6.87 (s, 1H), 6.76 (s, 1H), 6.41 (m, 1H), 6.19 (d, J=16.8 Hz, 1H), 5.73 (d, J=9.2 Hz, 1H), 3.78 (s, 3H), 2.92 (s, 2H), 2.75 (s, 3H), 2.35 (s, 2H), 2.21 (s, 6H).

Example 13: Preparation of N-(2-((2-(dimethylamino)ethyl)(methyl)amino)-5-((4-(6-fluoro-1H-indol-1-yl)pyrimidin-2-yl)amino)-4-methoxyphenyl)acrylamide (Compound 29) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^1$-(2-(dimethylamino)ethyl)-N$^4$-(4-(6-fluoro-1H-indol-1-yl)pyrimidin-2-yl)-5-methoxy-N$^1$-methylbenzene-1,2,4-triamine (403-A-29) (162 mg, 0.36 mmol, 1.0 eq). N-(2-((2-(Dimethylamino)ethyl)(methyl)amino)-5-((4-(6-fluoro-1H-indol-1-yl)pyrimidin-2-yl)amino)-4-methoxyphenyl)acrylamide was obtained as a yellow solid (60 mg, yield: 33.15%).

The characterization data of Compound 29 were: LCMS (ESI): m/z 504 [M+H]$^+$. M.p.: 164-165° C.; $^1$H NMR (500 MHz, DMSO-d6) δ 10.04 (s, 1H), 8.78 (s, 1H), 8.48 (s, 1H), 8.38 (d, J=5.7 Hz, 1H), 8.22 (d, J=9.7 Hz, 1H), 8.12 (d, J=3.7 Hz, 1H), 7.57 (dd, J=8.6, 5.7 Hz, 1H), 7.11 (d, J=5.7 Hz, 1H), 7.01 (m, 2H), 6.78 (d, J=3.6 Hz, 1H), 6.37 (dd, J=16.9, 10.2 Hz, 1H), 6.17 (dd, J=16.9, 1.8 Hz, 1H), 5.71 (m, 1H), 3.76 (s, 3H), 2.90 (s, 2H), 2.74 (s, 3H), 2.36 (s, 2H), 2.22 (s, 6H).

Example 14: Preparation of N-(2-((2-(dimethylamino)ethyl)(methyl)amino)-5-((4-(4-fluoro-1H-indol-1-yl)pyrimidin-2-yl)amino)-4-methoxyphenyl)acrylamide (Compound 30) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^1$-(2-(dimethylamino)ethyl)-N$^4$-(4-(4-fluoro-1H-indol-1-yl)pyrimidin-2-yl)-5-methoxy-N$^1$-methylbenzene-1,2,4-triamine (403-A-30) (195 mg, 0.43 mmol, 1.0 eq). N-(2-((2-(Dimethylamino)ethyl)(methyl)

amino)-5-((4-(4-fluoro-1H-indol-1-yl)pyrimidin-2-yl)amino)-4-methoxyphenyl)acrylamide was obtained as a yellow solid (60 mg, yield: 33.15%).

The characterization data of Compound 30 were: LCMS (ESI): m/z 504 [M+H]$^+$. M.p.: 165.5-166.5° C.; $^1$H NMR (500 MHz, DMSO-d6) δ 10.06 (s, 1H), 8.69 (s, 1H), 8.52 (s, 1H), 8.42 (d, J=5.6 Hz, 1H), 8.21 (dd, J=27.4, 5.8 Hz, 2H), 7.15 (d, J=5.7 Hz, 1H), 7.07 (m, 2H), 6.96 (dd, J=9.8, 8.2 Hz, 1H), 6.84 (d, J=3.6 Hz, 1H), 6.40 (dd, J=16.9, 10.2 Hz, 1H), 6.20 (dd, J=16.9, 1.8 Hz, 1H), 5.72 (dd, J=10.2, 1.6 Hz, 1H), 3.77 (s, 3H), 2.91 (t, J=5.7 Hz, 2H), 2.74 (d, J=10.0 Hz, 3H), 2.35 (d, J=5.3 Hz, 2H), 2.21 (s, 6H).

Example 15: Preparation of N-(5-((4-(5-chloro-1H-indol-1-yl)pyrimidin-2-yl)amino)-2-((2-(dimethylamino)ethyl)(methyl)amino)-4-methoxyphenyl)acrylamide (Compound 31) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(4-(5-chloro-1H-indol-1-yl)pyrimidin-2-yl)-N$^1$-(2-(dimethylamino)ethyl)-5-methoxy-N$^1$-methylbenzene-1,2,4-triamine (300 mg, 0.65 mmol, 1.0 eq). N-(5-((4-(5-Chloro-1H-indol-1-yl)pyrimidin-2-yl)amino)-2-((2-(dimethylamino)ethyl)(methyl)amino)-4-methoxyphenyl)acrylamide was obtained as a beige solid (85 mg, yield: 25%).

The characterization data of Compound 31 were: LCMS (ESI): m/z 520 [M+H]$^+$. M.p.: 150-153° C.; $^1$H NMR (500 MHz, DMSO-d6) δ 10.06 (s, 1H), 8.67 (s, 1H), 8.51 (s, 1H), 8.41 (d, J=5.6 Hz, 2H), 8.20 (d, J=3.6 Hz, 1H), 7.65 (d, J=2.1 Hz, 1H), 7.12 (d, J=5.7 Hz, 1H), 7.05 (m, 2H), 6.76 (d, J=3.5 Hz, 1H), 6.41 (dd, J=16.9, 10.2 Hz, 1H), 6.18 (dd, J=17.0, 1.8 Hz, 1H), 5.73 (dd, J=10.2, 1.6 Hz, 1H), 3.77 (d, J=7.7 Hz, 3H), 2.93 (t, J=5.7 Hz, 2H), 2.75 (d, J=8.8 Hz, 3H), 2.35 (t, J=5.5 Hz, 2H), 2.22 (s, 6H).

Example 16: Preparation of N-(5-((4-(5-cyano-1H-indol-1-yl)pyrimidin-2-yl) amino)-2-((2-(dimethylamino)ethyl)(methyl)amino)-4-methoxyphenyl)acrylamide (Compound 33) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by 1-(2-((5-amino-4-((2-(dimethylamino)ethyl)(methyl)amino)-2-methoxyphenyl)amino)pyrimidin-4-yl)-1H-indole-5-carbonitrile (403-A-33) (100 mg, 0.394 mmol, 1 eq). N-(5-((4-(5-Cyano-1H-indol-1-yl)pyrimidin-2-yl)amino)-2-((2-(dimethylamino)ethyl)(methyl)amino)-4-methoxyphenyl)acrylamide was obtained as a yellow solid (35 mg, yield: 31.53%).

The characterization data of Compound 33 were: LCMS (ESI): m/z 511 [M+H]$^+$. M.p.: 127-128° C.; $^1$H NMR (500 MHz, DMSO-d6) δ 10.08 (s, 1H), 8.83 (s, 1H), 8.59 (s, 1H), 8.46 (m, 2H), 8.32 (d, J=3.7 Hz, 1H), 8.14 (d, J=1.1 Hz, 1H), 7.40 (d, J=8.6 Hz, 1H), 7.18 (d, J=5.7 Hz, 1H), 7.07 (s, 1H), 6.90 (d, J=3.6 Hz, 1H), 6.41 (dd, J=17.0, 10.2 Hz, 1H), 6.17 (dd, J=16.9, 1.8 Hz, 1H), 5.73 (dd, J=10.2, 1.7 Hz, 1H), 3.78 (s, 3H), 2.92 (t, J=5.8 Hz, 2H), 2.76 (s, 3H), 2.34 (t, J=5.7 Hz, 2H), 2.21 (s, 6H).

Example 17: Preparation of N-{2-[(2-Dimethylamino-ethyl)-methyl-amino]-4-methoxy-5-[4-(5-nitro-indol-1-yl)-pyrimidin-2-ylamino]-phenyl}-acryl amide (Compound 34) (Prepared According to Scheme 6)

N$^1$-(2-(dimethylamino)ethyl)-5-methoxy-N$^1$-methyl-N$^4$-(4-(5-nitro-1H-indol-1-yl)pyrimidin-2-yl)benzene-1,2,4-triamine (403-A-34) (0.13 g, 0.27 mmol) and triethylamine (55 mg, 055 mmol) were dissolved in tetrahydrofuran (10 mL) and cooled to −70° C. Acryloyl chloride (25 mg, 0.27 mmol) was then added dropwise slowly while stirring. The mixture was reacted at −70° C. for 2 hours and methanol (1 mL) and water (15 mL) were added. The mixture was extracted with dichloromethane (15 mL) three times and the organic phase was dried, concentrated and purified by column chromatography (dichloromethane/methanol=10:1) to give N-{2-[(2-dimethylamino-ethyl)-methyl-amino]-4-methoxy-5-[4-(5-nitro-indol-1-yl)-pyrimidin-2-ylamino]-phenyl}-acryl amide as a yellow solid (90 mg, yield: 62.2%).

The characterization data of Compound 34 were: LCMS (ESI): m/z 531[M+H]$^+$. $^1$H NMR (500 MHz, DMSO-d6) δ 10.11 (s, 1H), 8.80 (s, 1H), 8.53 (m, 4H), 8.36 (d, J=3.6 Hz, 1H), 7.88 (d, J=8.0 Hz, 1H), 7.19 (d, J=5.6 Hz, 1H), 7.09 (s, 1H), 7.04 (d, J=3.6 Hz, 1H), 6.39 (dd, J=16.9, 10.2 Hz, 1H), 6.17 (dd, J=17.0, 1.7 Hz, 1H), 5.71 (m, 1H), 3.78 (s, 3H), 2.94 (t, J=5.7 Hz, 2H), 2.77 (s, 3H), 2.35 (t, J=5.7 Hz, 2H), 2.21 (s, 6H).

Example 18: Preparation of N-(2-((2-(dimethylamino)ethyl)(methyl)amino)-5-((4-(5-hydroxy-1H-indol-1-yl)pyrimidin-2-yl)amino)-4-methoxyphenyl) acrylamide (Compound 36) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by 1-(2-((5-amino-4-((2-(dimethylamino)ethyl)(methyl)amino)-2-methoxyphenyl)amino)pyrimidin-4-yl)-1H-indol-5-ol (403-A-36) (111 mg, 0.248 mmol, eq). N-(2-((2-(dimethylamino)ethyl)(methyl)amino)-5-((4-(5-hydroxy-1H-indol-1-yl)pyrimidin-2-yl)amino)-4-methoxyphenyl)acrylamide was obtained as a yellow solid (55 mg, yield: 44.12%).

The characterization data of Compound 36 were: LCMS (ESI): m/z 502 [M+H]$^+$. M.p.: 218-219° C.; $^1$H NMR (500 MHz, DMSO-d6) δ 10.08 (s, 1H), 9.00 (s, 1H), 8.53 (d, J=10.0 Hz, 2H), 8.33 (d, J=5.7 Hz, 1H), 8.17 (d, J=8.8 Hz, 1H), 8.03 (d, J=3.6 Hz, 1H), 7.05 (d, J=4.7 Hz, 2H), 6.88 (d, J=2.3 Hz, 1H), 6.58 (m, 2H), 6.39 (dd, J=16.9, 10.2 Hz, 1H), 6.20 (dd, J=16.9, 1.8 Hz, 1H), 5.73 (d, J=11.7 Hz, 1H), 3.77 (s, 3H), 2.91 (t, J=5.6 Hz, 2H), 2.76 (s, 3H), 2.34 (t, J=5.4 Hz, 2H), 2.22 (s, 6H).

Example 19: Preparation of N-(2-((2-(dimethylamino)ethyl)(methyl)amino)-5-((4-(5-(2-hydroxyethoxy)-1H-indol-1-yl)pyrimidin-2-yl)amino)-4-methoxyphenyl)acrylamide (Compound 37) (Prepared According to Scheme 6)

N$^4$-(4-(5-(2-((tert-butyldiphenylsilyl)oxy)ethoxy)-1H-indol-1-yl)pyrimidin-2-yl)-N$^1$-(2-(dimethylamino)ethyl)-5-methoxy-N$^1$-methylbenzene-1,2,4-triamine (403-A-37) (320 mg, 0.41 mmol, 1.0 eq), triethylamine (0.1 mL, 0.8 mmol, 2.0 eq), HATU (182 mg, 0.48 mmol, 1.2 eq) and acrylic acid (35 mg, 0.48 mmol, 1.2 eq) were added into dichloromethane (25 mL) and stirred at room temperature for 0.5 hour. The stirring was then stopped when the reaction was stopped and a saturated aqueous sodium carbonate solution was added and the mixture partitioned. The aqueous phase was extracted with dichloromethane twice. The organic phase was combined and washed with diluted aqueous hydrochloric acid and saturated brine in sequence, dried, concentrated in vacuo and purified by prep-TLC (eluent: dichloromethane/methanol 40/1 to 15/1) to give N-(5-((4-(5-(2-((tert-butyldiphenyl silyl)oxy)ethoxy)-1H-indol-1-yl)pyrimidin-2-yl)amino)-2-((2-(dimethylamino)ethyl)(methyl)amino)-4-methoxyphenyl)acrylamide as a yellow solid (200 mg, yield: 62%). MS (ESI): m/z 784 (M+H)$^+$.

The compound obtained above (200 mg, 0.25 mmol, 1.0 eq) was dissolved in tetrahydrofuran (20 mL) and TBAF (300 mg, 1.15 mmol, 4.6 eq) was added and stirred at room temperature for 1 hour, which was then concentrated in vacuo, extracted with dichloromethane which was then washed with water six times, dried over anhydrous sodium sulfate, concentrated in vacuo and purified by silica gel column chromatography (eluent: dichloromethane/methanol: 40/1~15/1) to give N-(2-((2-(dimethylamino)ethyl)(methyl)amino)-5-((4-(5-(2-hydroxyethoxy)-1H-indol-1-yl)pyrimidin-2-yl)amino)-4-methoxyphenyl)acrylamide as a yellow solid (30 mg, yield: 22%).

The characterization data of Compound 37 were: LCMS (ESI): m/z 546 [M+H]$^+$. m.p.: 65-67° C.; $^1$H NMR (500 MHz, DMSO-d6) δ 10.06 (s, 1H), 8.55 (d, J=14.9 Hz, 2H), 8.32 (dd, J=28.8, 7.0 Hz, 2H), 8.09 (d, J=3.1 Hz, 1H), 7.07 (dd, J=13.9, 8.1 Hz, 3H), 6.68 (t, J=7.7 Hz, 2H), 6.40 (dd, J=16.9, 10.2 Hz, 1H), 6.20 (d, J=16.8 Hz, 1H), 5.72 (d, J=10.1 Hz, 1H), 4.80 (s, 1H), 3.98 (t, J=4.8 Hz, 2H), 3.77 (s, 3H), 3.72 (d, J=3.6 Hz, 2H), 2.92 (s, 2H), 2.75 (s, 3H), 2.35 (s, 2H), 2.21 (s, 6H).

Example 20: Preparation of N-(2-((2-(dimethylamino)ethyl)(methyl)amino)-4-methoxy-5-((4-(5-(2-methoxyethoxy)-1H-indol-1-yl)pyrimidin-2-yl)amino)phenyl)acrylamide (Compound 38) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^1$-(2-(dimethylamino)ethyl)-5-methoxy-N$^4$-(4-(5-(2-methoxyethoxy)-1H-indol-1-yl)pyrimidin-2-yl)-N$^1$-methylbenzene-1,2,4-triamine (403-A-38) (140 mg, 0.28 mmol, 1.0 eq). N-(2-((2-(Dimethylamino)ethyl)(methyl)amino)-4-methoxy-5-((4-(5-(2-methoxyethoxy)-1H-indol-1-yl)pyrimidin-2-yl)amino)phenyl)acrylamide was obtained as a yellow solid (30 mg, yield: 19%).

The characterization data of Compound 38 were: LCMS (ESI): m/z 560 [M+H]$^+$. m.p.: 59-61° C.; $^1$H NMR (500 MHz, DMSO-d6) δ 10.03 (s, 1H), 8.56 (s, 2H), 8.35 (s, 2H), 8.10 (s, 1H), 7.09 (s, 3H), 6.69 (s, 2H), 6.43 (s, 1H), 6.21 (s, 1H), 5.73 (s, 1H), 4.09 (s, 3H), 3.73 (d, J=54.8 Hz, 7H), 2.95 (s, 2H), 2.75 (s, 3H), 2.39 (m, 2H), 2.25 (s, 6H).

Example 21: Preparation of N-(2-((2-(dimethylamino)ethyl)(methyl)amino)-5-((4-(5-(hydroxymethyl)-1H-indol-1-yl)pyrimidin-2-yl)amino)-4-methoxyphenyl)acrylamide (Compound 39) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by (1-(2-((5-amino-4-((2-(dimethylamino)ethyl)(methyl)amino)-2-methoxyphenyl)amino)pyrimidin-4-yl)-1H-indol-5-yl)methanol (403-A-38) (120 mg, 0.26 mmol, 1.0 eq). N-(2-((2-(Dimethylamino)ethyl)(methyl)amino)-5-((4-(5-(hydroxymethyl)-1H-indol-1-yl)pyrimidin-2-yl)amino)-4-methoxyphenyl)acryl amide was obtained as a yellow solid (25 mg, yield: 19%).

The characterization data of Compound 39 were: LCMS (ESI): m/z 516 [M+H]$^+$. m.p.: 67-68° C.; $^1$H NMR (500 MHz, DMSO-d6) δ 10.08 (s, 1H), 8.57 (s, 2H), 8.35 (d, J=26.2 Hz, 2H), 8.11 (s, 1H), 7.51 (s, 1H), 7.08 (d, J=26.0 Hz, 3H), 6.74 (s, 1H), 6.39 (s, 1H), 6.19 (d, J=16.3 Hz, 1H), 5.73 (s, 1H), 5.07 (s, 1H), 4.53 (s, 2H), 3.78 (s, 3H), 2.92 (s, 2H), 2.76 (s, 3H), 2.35 (s, 2H), 2.22 (s, 6H).

Example 22: Preparation of 1-(2-((5-acrylamido-4-((2-(dimethylamino)ethyl)(methyl)amino)-2-methoxyphenyl)amino)pyrimidin-4-yl)-1H-indole-5-carboxamide (Compound 41) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by 1-(2-((5-amino-4-((2-(dimethylamino)ethyl)(methyl)amino)-2-methoxyphenyl)amino)pyrimidin-4-yl)-1H-indole-5-carboxamide (100 mg, 0.21 mmol, eq). 1-(2-((5-Acrylamido-4-((2-(dimethylamino)ethyl)(methyl)amino)-2-methoxyphenyl)amino)pyrimidin-4-yl)-1H-indole-5-carboxamide was obtained as a beige solid (60 mg, yield: 54.3%).

The characterization data of Compound 41 were: LCMS (ESI): m/z 529 [M+H]$^+$. m.p.: 121.3-125.1° C.; $^1$H NMR (500 MHz, DMSO-d6) δ 10.05 (s, 1H), 8.68 (s, 1H), 8.52 (s, 1H), 8.42 (d, J=5.6 Hz, 2H), 8.21 (d, J=3.6 Hz, 1H), 8.13 (s, 1H), 7.88 (s, 1H), 7.65 (d, J=8.8 Hz, 1H), 7.16 (t, J=8.9 Hz, 2H), 7.06 (s, 1H), 6.84 (d, J=3.5 Hz, 1H), 6.40 (dd, J=16.8, 10.2 Hz, 1H), 6.19 (d, J=17.0 Hz, 1H), 5.71 (d, J=10.5 Hz, 1H), 3.78 (s, 3H), 2.93 (s, 2H), 2.77 (s, 3H), 2.36 (s, 2H), 2.21 (s, 6H).

Example 23: Preparation of N-(5-((4-(3-chloro-1H-indol-1-yl)pyrimidin-2-yl)amino)-2-((2-(dimethylamino)ethyl)(methyl)amino)-4-methoxyphenyl)acrylamide (Compound 46) (Prepared According to Scheme 6)

The synthetic method was similar to that described in EXAMPLE 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(4-(3-chloro-1H-indol-1-yl)pyrimidin-2-yl)-N$^1$-(2-(dimethylamino)ethyl)-5-methoxy-N$^1$-methylbenzene-1,2,4-triamine (403-A-46) (216 mg, 0.46 mmol, 1 eq). N-(5-((4-(3-Chloro-1H-indol-1-yl)pyrimidin-2-yl)amino)-2-((2-(dimethylamino)ethyl)(methyl)amino)-4-methoxyphenyl)acrylamide was obtained as a pale yellow solid (50 mg, yield: 29%).

The characterization data of Compound 46 were: LCMS (ESI): m/z 520 [M+H]$^+$. m.p.: 142-144° C.; $^1$H NMR (500 MHz, DMSO-d6) δ 10.05 (s, 1H), 8.67 (s, 1H), 8.56 (s, 1H), 8.43 (s, 3H), 7.55 (d, J=7.2 Hz, 1H), 7.28 (s, 1H), 7.21 (s, 1H), 7.15 (d, J=5.1 Hz, 1H), 7.06 (s, 1H), 6.41 (s, 1H), 6.22

(d, J=16.5 Hz, 1H), 5.73 (d, J=9.5 Hz, 1H), 3.78 (s, 3H), 2.94 (s, 2H), 2.72 (d, J=29.5 Hz, 3H), 2.37 (s, 2H), 2.24 (s, 6H).

Example 24: Preparation of N-(5-(4-(5-chloro-3-methyl-2-oxo-2,3-dihydro-1H-benzo[d]imidazol-1-yl)pyrimidin-2-ylamino)-2-((2-(dimethylamino) ethyl)(methyl)amino)-4-methoxyphenyl)acrylamide (Compound 51) (Prepared According to Scheme 7)

1-(2-((5-amino-4-((2-(dimethylamino)ethyl)(methyl) amino)-2-methoxyphenyl)amino)pyrimidin-4-yl)-5-chloro-3-methyl-1H-benzo[d]imidazol-2(3H)-one (506-A-51) (140 mg, 0.28 mmol, 1.0 eq), triethylamine (57 mg, 0.56 mmol, 2.0 eq) and 2-(-azobenzotriazole)-N,N,N',N'-tetramethyl-uronium hexafluorophosphate (117 mg, 0.308 mmol, 1.1 eq) were dissolved in dichloromethane (25 mL) and acrylic acid (22 mg, 0.308 mmol, 1.1 eq) was then added and reacted at room temperature. After reaction for half an hour, water (30 mL) was added and extracted. The organic phase was washed with aqueous sodium carbonate solution, dried over anhydrous sodium sulfate, and rotary evaporated. The residue was purified by silica gel column chromatography (dichloromethane/methanol: 500:1~150:1) to give N-(5-(4-(5-chloro-3-methyl-2-oxo-2,3-dihydro-1H-benzo[d]imidazol-1-yl)pyrimidin-2-ylamino)-2-((2-(dimethylamino)ethyl) (methyl)amino)-4-methoxyphenyl)acrylamide as a beige solid (23 mg, yield: 14.8%).

The characterization data of Compound 51 were: LCMS (ESI): m/z 551 [M+H]$^+$. m.p.: 70-71° C.; $^1$H NMR (500 MHz, DMSO-d6) δ 10.02 (s, 1H), 8.72 (s, 1H), 8.42 (m, 2H), 8.08 (s, 1H), 7.65 (d, J=5.6 Hz, 1H), 7.36 (s, 1H), 7.05 (s, 1H), 6.87 (d, J=8.5 Hz, 1H), 6.40 (dd, J=17.0, 10.2 Hz, 1H), 6.17 (d, J=16.9 Hz, 1H), 5.72 (d, J=10.1 Hz, 1H), 3.75 (s, 3H), 3.35 (s, 3H), 2.92 (s, 2H), 2.74 (s, 3H), 2.34 (s, 2H), 2.21 (s, 6H).

Example 25: Preparation of N-(5-((4-(5-cyano-3-methyl-2-oxo-2,3-dihydro-1H-benzo[d]imidazol-1-yl)pyrimidin-2-yl)amino)-2-((2-(dimethylamino) ethyl)(methyl)amino)-4-methoxyphenyl)acrylamide (Compound 52) (Prepared According to Scheme 7)

The synthetic method was similar to that described in EXAMPLE 24, except that 1-(2-(5-amino-4-((2-(dimethylamino)ethyl)(methyl)amino)-2-methoxyphenylamino)pyrimidin-4-yl)-5-chloro-3-methyl-1H-benzo[d]imidazol-2(3H)-one (506-A-51) was replaced by 1-(2-((5-amino-4-((2-(dimethylamino)ethyl)(methyl)amino)-2-methoxyphenyl) amino)pyrimidin-4-yl)-3-methyl-2-oxo-2,3-dihydro-1H-benzo[d]imidazole-5-carbonitrile (506-A-52) (65.4 mg, 0.136 mmol, 1 eq). N-(5-((4-(5-Cyano-3-methyl-2-oxo-2,3-dihydro-1H-benzo[d]imidazol-1-yl)pyrimidin-2-yl)amino)-2-((2-(dimethylamino)ethyl)(methyl)amino)-4-methoxyphenyl)acrylamide was obtained as a yellow solid (40 mg, yield: 55.06%).

The characterization data of Compound 52 were: LCMS (ESI): m/z 542 [M+H]$^+$. m.p.: 183-185° C.; $^1$H NMR (500 MHz, DMSO-d6) δ 10.00 (s, 1H), 8.79 (s, 1H), 8.48 (d, J=5.3 Hz, 1H), 8.39 (s, 1H), 8.23 (s, 1H), 7.77 (s, 1H), 7.62 (d, J=5.2 Hz, 1H), 7.31 (d, J=7.3 Hz, 1H), 7.05 (s, 1H), 6.41 (dd, J=16.7, 10.2 Hz, 1H), 6.17 (d, J=17.0 Hz, 1H), 5.72 (d, J=10.1 Hz, 1H), 3.77 (s, 3H), 3.39 (s, 3H), 2.92 (s, 2H), 2.75 (s, 3H), 2.35 (s, 2H), 2.21 (s, 6H).

Example 26: Preparation of N-(2-((2-(dimethylamino)ethyl) (methyl)amino)-4-methoxy-5-((4-(5-methoxy-3-methyl-2-oxo-2,3-dihydro-1H-benzo[d] imidazol-1-yl)pyrimidin-2-yl) amino)phenyl)acryl amide (Compound 53) (Prepared According to Scheme 7)

The synthetic method was similar to that described in EXAMPLE 24, except that 1-(2-(5-amino-4-((2-(dimethylamino)ethyl)(methyl)amino)-2-methoxyphenylamino)pyrimidin-4-yl)-5chloro-3-methyl-1H-benzo[d]imidazol-2 (3H)-one (506-A-51) therein was replaced by 1-(2-((5-amino-4-((2-(dimethylamino)ethyl)(methyl)amino)-2-methoxyphenyl)amino)pyrimidin-4-yl)-5-methoxy-3-methyl-1H-benzo[d]imidazol-2(3H)-one (506-A-53) (170 mg, 0.35 mmol, 1 eq). N-(2-((2-(Dimethylamino)ethyl) (methyl)amino)-4-methoxy-5-((4-(5-methoxy-3-methyl-2-oxo-2,3-dihydro-1H-benzo[d]imidazol-1-yl)pyrimidin-2-yl) amino)phenyl)acrylamide was obtained as a beige solid (80 mg, yield: 42%).

The characterization data of Compound 53 were: LCMS (ESI): m/z 547 [M+H]$^+$. m.p.: 75-87° C.; $^1$H NMR (500 MHz, DMSO-d6) δ 10.04 (s, 1H), 8.65 (s, 1H), 8.40 (m, 2H), 7.98 (d, J=7.7 Hz, 1H), 7.69 (d, J=5.7 Hz, 1H), 7.05 (s, 1H), 6.84 (d, J=2.3 Hz, 1H), 6.39 (dd, J=16.9, 10.1 Hz, 2H), 6.18 (dd, J=17.0, 1.6 Hz, 1H), 5.73 (m, 1H), 3.76 (t, J=8.5 Hz, 6H), 3.34 (s, 3H), 2.92 (t, J=5.5 Hz, 2H), 2.75 (s, 3H), 2.35 (d, J=5.2 Hz, 2H), 2.21 (s, 6H).

Example 27: Preparation of N-(2-((2-(dimethylamino)ethyl) (methyl)amino)-4-methoxy-5-((5-methoxy-4-(3-methyl-2-oxo-2,3-dihydro-1H-benzo [d]imidazol-1-yl)pyrimidin-2-yl)amino)phenyl) acrylamide (Compound 57) (Prepared According to Scheme 7)

The synthetic method was similar to that described in EXAMPLE 24, except that 1-(2-(5-amino-4-((2-(dimethylamino)ethyl)(methyl)amino)-2-methoxyphenylamino)pyrimidin-4-yl)-5chloro-3-methyl-1H-benzo[d]imidazol-2 (3H)-one (506-A-51) therein was replaced by 1-(2-((5-amino-4-((2-(dimethylamino)ethyl)(methyl)amino)-2-methoxyphenyl) amino)-5-methoxypyrimidin-4-yl)-3-methyl-1H-benzo[d]imidazol-2(3H)-one (506-A-57) (400 mg, 0.81 mmol, 1.0 eq). N-(2-((2-(Dimethylamino)ethyl) (methyl)amino)-4-methoxy-5-((5-methoxy-4-(3-methyl-2-oxo-2,3-dihydro-1H-benzo[d]imidazol-1-yl)pyrimidin-2-yl) amino)phenyl)acrylamide was obtained as a yellow solid (15 mg, yield: 45.08%).

The characterization data of Compound 57 were: LCMS (ESI): m/z 547 [M+H]$^+$; m.p.: 168-172° C.; $^1$H NMR (500 MHz, DMSO-d6) δ 9.99 (s, 1H), 8.63 (s, 1H), 8.58 (s, 1H), 8.20 (s, 1H), 7.21 (d, J=7.8 Hz, 1H), 7.13 (t, J=7.6 Hz, 1H), 7.08 (d, J=7.7 Hz, 1H), 7.01 (t, J=7.6 Hz, 1H), 6.96 (s, 1H), 6.37 (dd, J=16.9, 10.1 Hz, 1H), 6.22 (d, J=17.0 Hz, 1H), 5.73 (d, J=10.5 Hz, 1H), 3.81 (d, J=9.0 Hz, 6H), 3.37 (s, 3H), 2.83 (t, J=5.6 Hz, 2H), 2.68 (s, 3H), 2.27 (t, J=5.4 Hz, 2H), 2.18 (s, 6H).

Example 28: Preparation of (E)-N-(5-((4-(1H-indol-1-yl)pyrimidin-2-yl)amino)-2-((2-(dimethylamino) ethyl)(methyl)amino)-4-methoxyphenyl)but-2-enamide (Compound 66) (Prepared According to Scheme 6)

(E)-but-2-enoic acid (602-66) (24 mg, 0.277 mmol, 1.2 eq), triethylamine (58.3 mg, 0.58 mmol, 2.5 eq), and HATU (114 mg, 0.3 mmol, 1.3 eq) were dissolved in dichloromethane (10 mL) at room temperature. After stirring for half an hour, $N^4$-(4-(1H-indol-1-yl)pyrimidin-2-yl)-$N^1$-(2-(dimethylamino)ethyl)-5-methoxy-$N^1$-methylbenzene-1,2,4-triamine (403-A-1) (100 mg, 0.232 mmol, 1 eq) in dichloromethane (2 mL) was added dropwise to the reaction and stirred for 1 hour. The reaction solution was extracted with water and ethyl acetate. The organic phase was washed with brine, dried over anhydrous sodium sulfate, concentrated in vacuo and purified by silica gel column chromatography (eluent: dichloromethane/methanol: 80/1) to give (E)-N-(5-((4-(1H-Indol-1-yl)pyrimidin-2-yl)amino)-2-((2-(dimethylamino)ethyl)(methyl)amino)-4-methoxyphenyl)but-2-enamide (50 mg, 0.1 mmol, yield: 43.1%).

The characterization data of of Compound 66 were: LCMS (ESI): m/z 500 [M+H]$^+$. m.p.: 150.2-152.8° C.; $^1$H NMR (500 MHz, DMSO-d6) δ 9.86 (s, 1H), 8.57 (d, J=20.3 Hz, 2H), 8.38 (d, J=5.6 Hz, 2H), 8.13 (d, J=3.5 Hz, 1H), 7.58 (d, J=7.7 Hz, 1H), 7.10 (m, 4H), 6.74 (m, 2H), 6.07 (d, J=15.2 Hz, 1H), 3.76 (s, 3H), 2.90 (t, J=5.3 Hz, 2H), 2.74 (s, 3H), 2.35 (t, J=5.4 Hz, 2H), 2.22 (s, 6H), 1.87 (d, J=6.7 Hz, 3H).

Example 29: Preparation of (E)-N-(5-((4-(1H-indol-1-yl)pyrimidin-2-yl)amino)-2-((2-(dimethylamino)ethyl)(methyl)amino)-4-methoxyphenyl)pent-2-enamide (Compound 67) (Prepared According to Scheme 6)

The synthetic method was similar to that described in EXAMPLE 28, except that (E)-but-2-enoic acid (602-66) therein was replaced by trans-2-pentenoic acid (602-67) (26 mg, 0.25 mmol, 1.2 eq). (E)-N-(5-((4-(1H-Indol-1-yl)pyrimidin-2-yl)amino)-2-((2-(dimethylamino)ethyl)(methyl)amino)-4-methoxyphenyl)pent-2-enamide was obtained as a slightly yellow solid (19 mg, yield: 18%).

The characterization data of Compound 67 were: LCMS (ESI): m/z 514 [M+H]$^+$. m.p.: 124.3-126.2° C.; $^1$H NMR (500 MHz, DMSO-d6) δ 9.89 (s, 1H), 8.65 (s, 1H), 8.50 (s, 1H), 8.38 (d, J=5.7 Hz, 2H), 8.13 (d, J=3.6 Hz, 1H), 7.58 (d, J=7.7 Hz, 1H), 7.10 (ddd, J=35.6, 16.6, 9.3 Hz, 4H), 6.80 (m, 2H), 6.08 (dd, J=17.2, 10.2 Hz, 1H), 3.77 (s, 3H), 2.94 (s, 2H), 2.74 (s, 3H), 2.24 (dd, J=22.1, 15.0 Hz, 8H), 1.23 (s, 2H), 1.05 (t, J=7.4 Hz, 3H).

Example 30: Preparation of N-(5-((4-(1H-indol-1-yl)pyrimidin-2-yl)amino)-2-((2-(dimethylamino)ethyl)(methyl)amino)-4-methoxyphenyl)methacryl amide (Compound 68) (Prepared According to Scheme 6)

The synthetic method was similar to that described in EXAMPLE 28, except that (E)-but-2-enoic acid (602-66) therein was replaced by methacrylic acid (602-68) (24 mg, 0.28 mmol, 1.2 eq). N-(5-((4-(1H-Indol-1-yl)pyrimidin-2-yl)amino)-2-((2-(dimethylamino)ethyl)(methyl)amino)-4-methoxyphenyl)methacrylamide was obtained as a beige solid (70 mg, yield: 60%).

The characterization data of Compound 68 were: LCMS (ESI): m/z 500 [M+H]$^+$. m.p.: 145.7-147.1° C.; NMR (500 MHz, DMSO-d6) δ 9.81 (s, 1H), 8.59 (s, 1H), 8.53 (s, 1H), 8.40 (d, J=5.7 Hz, 2H), 8.14 (d, J=3.7 Hz, 1H), 7.59 (d, J=7.6 Hz, 1H), 7.12 (m, 4H), 6.77 (d, J=3.6 Hz, 1H), 5.79 (s, 1H), 5.50 (s, 1H), 3.79 (s, 3H), 3.01 (s, 2H), 2.71 (s, 3H), 2.17 (s, 8H), 1.97 (s, 3H).

Example 31: Preparation of (E)-N-(5-((4-(1H-indol-1-yl)pyrimidin-2-yl)amino)-2-((2-(dimethylamino)ethyl)(methyl)amino)-4-methoxyphenyl)-4-(dimethylamino)but-2-enamide (Compound 69) (Prepared According to Scheme 6)

The synthetic method was similar to that described in Example 28, except that (E)-but-2-enoic acid (602-66) therein was replaced by trans-4-dimethylaminocrotonic acid hydrochloride (602-69)(37 mg, 0.22 mmol, 1.2 eq). (E)-N-(5-((4-(1H-Indol-1-yl)pyrimidin-2-yl)amino)-2-((2-(dimethylamino)ethyl)(methyl)amino)-4-methoxyphenyl)-4-(dimethylamino)but-2-enamide was obtained as a brown solid (40 mg, yield: 40%).

The characterization data of Compound 69 were: LCMS (ESI): m/z 543[M+H]$^+$. m.p.: 116.2-118.1° C.; $^1$H. NMR (500 MHz, DMSO-d$_6$) δ 9.92 (s, 1H), 8.50 (m, 4H), 8.13 (s, 1H), 7.59 (s, 1H), 7.08 (d, J=44.8 Hz, 4H), 6.72 (d, J=41.2 Hz, 2H), 6.30 (s, 1H), 3.79 (s, 3H), 3.29 (s, 2H), 3.12 (s, 2H), 2.99 (s, 2H), 2.73 (s, 3H), 2.35 (s, 6H), 2.22 (s, 6H).

Example 32: Preparation of (E)-N-(5-(4-(1H-indol-1-yl)pyrimidin-2-ylamino)-2-((2-(dimethylamino)ethyl)(methyl)amino)-4-methoxyphenyl)-4-(piperidin-1-yl)but-2-enamide (Compound 70) (Prepared According to Scheme 6)

$N^4$-(4-(1H-indol-1-yl)pyrimidin-2-yl)-$N^1$-(2-(dimethylamino)ethyl)-5-methoxy-$N^1$-methylbenzene-1,2,4-triamine (403-1) (145 mg, 0.336 mmol, 1.0 eq) was dissolved in MeCN (30 mL). N, N-diisopropylethylamine (87 mg, 0.672 mmol, 2.0 eq), HATU (128 mg, 0.336 mmol, 1.0 eq) and (E)-4-(piperidin-1-yl)but-2-enoic acid (602-70)(100 mg, crude) were then added in sequence, and the mixture was stirred at room temperature for two hours. After the reaction was completed, saturated aqueous sodium carbonate solution was added to quench the reaction and extracted with dichloromethane (3×80 mL). The organic phase was combined, dried over anhydrous sodium sulfate, concentrated and purified by silica gel column chromatography (eluent: dichloromethane/methanol: 60:1 to 15:1) to give (E)-N-(5-(4-(1H-indol-1-yl)pyrimidin-2-ylamino)-2-((2-(dimethylamino)ethyl)(methyl)amino)-4-methoxyphenyl)-4-(piperidin-1-yl)but-2-enamide as a gray solid (60 mg, yield: 30.6%).

The characterization data of Compound 70 were: MS (ESI): m/z 583[M+H]$^+$. $^1$H NMR (500 MHz, DMSO-d$_6$) δ 9.92 (s, 1H), 8.57 (s, 1H), 8.42 (m, 3H), 8.13 (d, J=3.6 Hz, 1H), 7.58 (d, J=7.4 Hz, 1H), 7.13 (m, 3H), 7.03 (s, 1H), 6.77 (d, J=3.5 Hz, 1H), 6.69 (m, 1H), 6.36 (s, 1H), 3.79 (s, 3H), 3.16 (s, 2H), 3.04 (s, 2H), 2.71 (s, 3H), 2.42 (s, 12H), 1.54 (s, 4H), 1.40 (s, 2H).

Example 33: Preparation of (N-(5-((4-(1H-indol-1-yl)pyrimidin-2-yl)amino)-2-((2-(dimethylamino)ethyl)(methyl)amino)-4-methoxyphenyl)but-2-ynamide) (Compound 73) (Prepared According to Scheme 6)

The synthetic method was similar to that described in Example 28, except that (E)-but-2-enoic acid (602-66) therein was replaced by 2-butynoic acid (604-73) (21 mg, 0.25 mmol, 1.2 eq), N-(5-((4-(1H-Indol-1-yl)pyrimidin-2-yl)amino)-2-((2-(dimethylamino)ethyl)(methyl)amino)-4-methoxyphenyl)but-2-ynamide was obtained as a slightly yellow solid (48 mg, yield: 46%).

The characterization data of Compound 73 were: LCMS (ESI): m/z 498[M+H]$^+$. m.p.: 189.7-191.8° C.; $^1$H NMR (500 MHz, DMSO-d$_6$) δ 10.95 (s, 1H), 8.60 (s, 1H), 8.39 (m, 3H), 8.11 (d, J=3.6 Hz, 1H), 7.59 (d, J=7.6 Hz, 1H), 7.13 (m, 4H), 6.77 (d, J=3.5 Hz, 1H), 3.77 (s, 3H), 2.90 (s, 2H), 2.75 (s, 3H), 2.31 (d, J=24.4 Hz, 8H), 2.03 (s, 3H).

Example 34: Preparation of (N-(5-((4-(1H-indol-1-yl)pyrimidin-2-yl)amino)-2-((2-(dimethylamino) ethyl)(methyl)amino)-4-methoxyphenyl)pent-2-ynamide) (Compound 74) (Prepared According to Scheme 6)

The synthetic method was similar to that described in Example 28, except that (E)-but-2-enoic acid (602-66) therein was replaced by 2-pentynoic acid (25 mg, 0.25 mmol, 1.2 eq). N-(5-((4-(1H-Indol-1-yl)pyrimidin-2-yl) amino)-2-((2-(dimethylamino)ethyl)(methyl) amino)-4-methoxyphenyl)pent-2-ynamide was obtained as a slightly yellow solid (27 mg, yield: 25%).

The characterization data of Compound 74 were: LCMS (ESI): m/z 512[M+H]$^+$. m.p.: 149.4-151.7° C.; $^1$H NMR (500 MHz, DMSO-d$_6$) δ 10.92 (s, 1H), 8.60 (s, 1H), 8.39 (d, J=5.6 Hz, 3H), 8.11 (d, J=3.6 Hz, 1H), 7.59 (d, J=7.6 Hz, 1H), 7.13 (m, 4H), 6.77 (d, J=3.5 Hz, 1H), 3.78 (s, 3H), 2.96 (s, 2H), 2.74 (s, 3H), 2.41 (dt, J=27.1, 13.5 Hz, 8H), 1.24 (s, 2H), 1.16 (t, J=7.5 Hz, 3H).

Example 35: Preparation of N-(5-(4-(1H-indol-1-yl) pyrimidin-2-ylamino)-2-(3-(dimethylamino)azetidin-1-yl)-4-methoxyphenyl)acrylamide (Compound 77) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^1$-(4-(1H-indol-1-yl)pyrimidin-2-yl)-4-(3-(dimethylamino)azetidin-1-yl)-6-methoxybenzene-1,3-diamine (403-C-77) (179 mg, 0.416 mmol, 1.0 eq), N-(5-(4-(1H-Indol-1-yl)pyrimidin-2-ylamino)-2-(3-(dimethylamino)azetidin-1-yl)-4-methoxyphenyl)acrylamide was obtained as a beige solid (45 mg, yield: 22%).

The characterization data of Compound 77 were: LCMS (ESI): m/z 484[M+H]$^+$. m.p.: 81-83° C.; $^1$H NMR (500 MHz, DMSO-d$_6$) δ 9.26 (s, 1H), 8.41 (s, 2H), 8.34 (d, J=5.6 Hz, 1H), 8.07 (d, J=3.6 Hz, 1H), 7.58 (d, J=7.5 Hz, 1H), 7.46 (s, 1H), 7.17 (dt, J=19.2, 7.2 Hz, 2H), 7.06 (d, J=5.7 Hz, 1H), 6.76 (d, J=3.5 Hz, 1H), 6.47 (dd, J=17.1, 10.2 Hz, 1H), 6.20 (m, 2H), 5.66 (d, J=11.8 Hz, 1H), 3.97 (t, J=7.0 Hz, 2H), 3.78 (s, 3H), 3.59 (t, J=6.6 Hz, 2H), 3.08 (m, 1H), 2.09 (s, 6H).

Example 36: Preparation of (S)—N-(5-((4-(1H-indol-1-yl)pyrimidin-2-yl)amino)-2-(3-(dimethylamino)pyrrolidin-1-yl)-4-methoxyphenyl)acrylamide (Compound 78) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N1-methylbenzene-1,2,4-triamine (403-A-5) therein was replaced by (S)—N$^1$-(4-(1H-indol-1-yl)pyrimidin-2-yl)-4-(3-(dimethylamino)pyrrolidin-1-yl)-6-methoxybenzene-1,3-diamine (403-C-78) (130 mg, 0.293 mmol, 1.0 eq), (S)—N-(5-((4-(1H-Indol-1-yl)pyrimidin-2-yl)amino)-2-(3-(dimethylamino)pyrrolidin-1-yl)-4-methoxyphenyl) acrylamide was obtained as a yellow solid (100 mg, yield: 68.49%).

The characterization data of Compound 78 were: LCMS (ESI): m/z 498 [M+H]$^+$; m.p.: 161-162° C.; $^1$H NMR (500 MHz, DMSO-d$_6$) δ 9.32 (s, 1H), 8.43 (s, 2H), 8.35 (d, J=5.6 Hz, 1H), 8.08 (d, J=3.5 Hz, 1H), 7.58 (d, J=8.5 Hz, 2H), 7.16 (d, J=3.6 Hz, 2H), 7.07 (d, J=5.7 Hz, 1H), 6.76 (d, J=3.4 Hz, 1H), 6.51 (m, 2H), 6.17 (d, J=17.0 Hz, 1H), 5.66 (d, J=10.3 Hz, 1H), 3.79 (s, 3H), 3.39 (dd, J=15.9, 9.0 Hz, 1H), 3.22 (dd, J=16.5, 7.4 Hz, 3H), 2.71 (s, 1H), 2.18 (s, 6H), 2.09 (s, 1H), 1.74 (dd, J=20.0, 10.1 Hz, 1H).

Example 37: Preparation of (R)—N-(5-((4-(1H-indol-1-yl)pyrimidin-2-yl)amino)-2-(3-(dimethylamino)pyrrolidin-1-yl)-4-methoxyphenyl)acrylamide (Compound 79) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N1-methylbenzene-1,2,4-triamine (403-A-5) therein was replaced by (R)—N$^1$-(4-(1H-indol-1-yl)pyrimidin-2-yl)-4-(3-(dimethylamino)pyrrolidin-1-yl)-6-methoxybenzene-1,3-diamine (403-C-79) (135 mg, 0.305 mmol, 1.0 eq). (R)—N-(5-((4-(1H-Indol-1-yl)pyrimidin-2-yl)amino)-2-(3-(dimethylamino)pyrrolidin-1-yl)-4-methoxyphenyl) acrylamide was obtained as a yellow solid (69 mg, yield: 56.67%).

The characterization data of Compound 79 were: LCMS (ESI): m/z 498 [M+H]$^+$; m.p.: 161-162° C.; $^1$H NMR (500 MHz, DMSO-d$_6$) δ 9.32 (s, 1H), 8.43 (s, 2H), 8.35 (d, J=5.6 Hz, 1H), 8.08 (d, J=3.6 Hz, 1H), 7.58 (d, J=9.0 Hz, 2H), 7.16 (m, 2H), 7.07 (d, J=5.7 Hz, 1H), 6.76 (d, J=3.5 Hz, 1H), 6.51 (m, 2H), 6.17 (d, J=17.1 Hz, 1H), 5.67 (d, J=10.3 Hz, 1H), 3.79 (s, 3H), 3.39 (dd, J=15.9, 9.2 Hz, 1H), 3.22 (dd, J=16.3, 7.3 Hz, 3H), 2.71 (m, 1H), 2.18 (s, 6H), 2.09 (s, 1H), 1.74 (dd, J=20.4, 9.6 Hz, 1H).

Example 38: Preparation of N-(5-(4-(1H-indol-1-yl) pyrimidin-2-ylamino)-4-methoxy-2-(methyl(2-(pyrrolidin-1-yl)ethyl)amino)phenyl)acrylamide (Compound 80) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N1-methylbenzene-1,2,4-triamine (403-A-5) therein was replaced by N$^4$-(4-(1H-indol-1-yl)pyrimidin-2-yl)-5-methoxy-N$^1$-methyl-N$^1$-(2-(pyrrolidin-1-yl)ethyl)benzene-1,2,4-triamine (403-B-80) (169 mg, 0.369 mmol, 1.0 eq), N-(5-(4-(1H-Indol-1-yl)pyrimidin-2-ylamino)-4-methoxy-2-(methyl(2-(pyrrolidin-1-yl)ethyl)amino)phenyl) acrylamide was obtained as a yellow solid (25 mg, yield: 13.3%).

The characterization data of Compound 80 were: LCMS (ESI): m/z 512 [M+H]$^+$. m.p.: 151-153° C.; $^1$H NMR (500 MHz, DMSO-d$_6$) δ 9.75 (s, 1H), 8.59 (s, 1H), 8.48 (s, 1H), 8.39 (d, J=5.6 Hz, 2H), 8.13 (d, J=3.7 Hz, 1H), 7.58 (d, J=7.6 Hz, 1H), 7.11 (ddd, J=30.8, 17.7, 11.4 Hz, 4H), 6.76 (d, J=3.6 Hz, 1H), 6.45 (m, 1H), 6.19 (d, J=16.9 Hz, 1H), 5.73 (m, 1H), 3.78 (s, 3H), 3.00 (s, 2H), 2.74 (s, 3H), 2.50 (d, J=1.7 Hz, 6H), 1.73 (s, 4H).

Example 39: Preparation of N-{5-(4-indol-1-yl-pyrimidin-2-ylamino)-4-methoxy-2-[methyl-(2-morpholin-4-yl-ethyl)-amino]-phenyl}-acryl amide (Compound 82) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(4-(1H-indol-1-yl)pyrimidin-2-yl)-5-methoxy-N$^1$-methyl-N$^1$-(2-morpholin-4-yl-ethyl)benzene-1,2,4-triamine (403-B-82) (0.12 g, 0.25 mmol). N-{5-(4-Indol-1-yl-pyrimidin-2-ylamino)-4-methoxy-2-[methyl-(2-morpholin-4-yl-ethyl)-amino]-phenyl}-acrylamide was obtained as a yellow solid (25 mg, yield: 13.3%).

The characterization data of Compound 82 were: LCMS (ESI): m/z 528[M+H]$^+$; $^1$H NMR (500 MHz, DMSO-d$_6$) δ 9.29 (s, 1H), 8.58 (s, 1H), 8.39 (m, 3H), 8.12 (d, J=3.7 Hz, 1H), 7.58 (d, J=7.2 Hz, 1H), 7.12 (m, 3H), 7.01 (s, 1H), 6.76 (d, J=3.6 Hz, 1H), 6.61 (dd, J=16.9, 10.2 Hz, 1H), 6.19 (dd, J=17.0, 1.7 Hz, 1H), 5.73 (d, J=10.6 Hz, 1H), 3.79 (s, 3H), 3.55 (m, 4H), 3.03 (t, J=6.6 Hz, 2H), 2.74 (s, 3H), 2.41 (t, J=6.6 Hz, 2H), 2.34 (s, 4H).

Example 40: Preparation of N-(5-((4-(1H-indol-1-yl)pyrimidin-2-yl)amino)-4-methoxy-2-(4-methylpiperazin-1-yl) phenyl)acrylamide (Compound 84) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N1-methylbenzene-1,2,4-triamine (403-A-5) therein was replaced by N$^1$-(4-(1H-indol-1-yl)pyrimidin-2-yl)-6-methoxy-4-(4-methylpiperazin-1-yl)benzene-1,3-diamine (403-C-84) (180 mg, 0.41 mmol, 1.0 eq). N-(5-((4-(1H-Indol-1-yl)pyrimidin-2-yl)amino)-4-methoxy-2-(4-methylpiperazin-1-yl) phenyl)acrylamide was obtained as a light yellow solid (40 mg, yield: 20%).

The characterization data of Compound 84 were: LCMS (ESI): m/z 484[M+H]$^+$; m.p.: 204-205° C.; $^1$H NMR (500 MHz, DMSO-d$_6$) δ 9.03 (s, 1H), 8.63 (s, 1H), 8.39 (t, J=8.8 Hz, 2H), 8.21 (s, 1H), 8.12 (d, J=3.5 Hz, 1H), 7.58 (d, J=7.3 Hz, 1H), 7.14 (m, 3H), 6.90 (s, 1H), 6.77 (d, J=3.4 Hz, 1H), 6.62 (dd, J=16.9, 10.2 Hz, 1H), 6.18 (d, J=17.1 Hz, 1H), 5.71 (d, J=10.3 Hz, 1H), 3.78 (s, 3H), 2.91 (s, 4H), 2.58 (s, 4H), 2.28 (s, 3H).

Example 41: Preparation of N-(2-((2-(dimethylamino)ethyl)(methyl)amino)-4-methoxy-5-((4-(5-methoxy-1H-pyrrolo[3,2-b]pyridin-1-yl)pyrimidin-2-yl)amino)phenyl)acrylamide (Compound 20) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N1-methylbenzene-1,2,4-triamine (403-A-5) therein was replaced by N$^1$-(2-(dimethylamino)ethyl)-5-methoxy-N$^4$-(4-(5-methoxy-1H-pyrrolo[3,2-b]pyri din-1-yl)pyrimidin-2-yl)-N$^1$-methylbenzene-1,2,4-triamine (403-A-20) (132 mg, 0.286 mmol, 1.0 eq). N-(2-((2-(Dimethylamino)ethyl)(methyl)amino)-4-methoxy-5-((4-(5-methoxy-1H-pyrrolo[3,2-b]pyridin-1-yl)pyrimidin-2-yl)amino)phenyl)acrylamide was obtained as a white solid (90 mg, yield: 61.05%).

The characterization data of Compound 20 were: LCMS (ESI): m/z 517 [M+H]$^+$. m.p.: 177-178° C.; $^1$H NMR (500 MHz, DMSO-d$_6$) δ 10.05 (s, 1H), 8.71 (s, 1H), 8.61 (s, 1H), 8.49 (s, 1H), 8.40 (d, J=5.0 Hz, 1H), 8.32 (s, 1H), 7.14 (d, J=5.1 Hz, 1H), 7.05 (s, 1H), 6.74 (s, 1H), 6.43 (m, 2H), 6.18 (d, J=16.8 Hz, 1H), 5.72 (d, J=9.8 Hz, 1H), 3.87 (s, 3H), 3.76 (s, 3H), 2.91 (s, 2H), 2.75 (s, 3H), 2.34 (s, 2H), 2.21 (s, 6H).

Example 42: Preparation of N-(2-((2-(dimethylamino)ethyl)(methyl) amino)-5-((4-(5-fluoro-3-methyl-2-oxo-2,3-dihydro-1H-benzo[d]imidazol-1-yl)pyrimidin-2-yl)amino)-4-methoxyphenyl) acrylamide (Compound 50) (Prepared According to Scheme 7)

Step 42a: Preparation of 5-fluoro-N$^1$-methylbenzene-1,2-diamine (Intermediate 501-50): Under an ice bath condition, 2,4-difluoronitrobenzene (10 g, 62.9 mmol, 1.0 eq) was dissolved in tetrahydrofuran (150 mL) and was then added 40% aqueous solution of methylamine (9.8 g, 125 mmol, 2.0 eq) was added dropwise quickly. The mixture was reacted at room temperature for 4 hours and the LCMS check indicated reaction completion. Petroleum ether (50 mL) and ethyl acetate (50 mL) were added to the reaction, washed with water, 2 mol/L hydrochloric acid, aqueous sodium bicarbonate solution and saturated brine, dried over sodium sulfate and rotary evaporated to give 5-fluoro-N-methyl-2-nitroaniline as a yellow solid (10.7 g, yield: 100%). The characterization data of compound were: LCMS (ESI): m/z 171 [M+H]$^+$. The compound obtained above (10.5 g, 61.8 mmol, 1.0 eq), iron powder (17.3 g, 309 mmol, 5.0 eq), ammonium chloride (16.5 g, 309 mmol, 5.0 eq) and water (50 mL) were dissolved in ethanol (200 mL) and placed in an 85° C. oil bath and reacted for 3 hours. The LCMS check indicated reaction completion and the reaction was cooled to room temperature and poured into water (200 mL) and then dichloromethane (200 mL) was added, stirred for 5 min, filtered through celite and the filtrate was partitioned. The organic phase was dried over anhydrous sodium sulfate and the solvent was rotary evaporated to give 5-fluoro N$^1$-methylbenzene-1,2-diamineas a red liquid product (8.5 g, yield: 98.2%). The characterization data o Step 42b: Preparation of 6-fluoro-1-methyl-1H-benzo[d]imidazol-2(3H)-one (Intermediate 502-50): 5-Fluoro-N$^1$-methylbenzene-1,2-diamine (501-50) (4.2 g, 30.0 mmol, 1.0 eq) was dissolved in dichloromethane (100 mL) and then triethylamine (6.1 g, 60.0 mmol, 2.0 eq) was added. Under nitrogen protection, the reaction was cooled to about 0° C. with an ice bath and then triphosgene (3.1 g, 10.5 mmol, 0.35 eq) in dichloromethane (50 mL) was added dropwise to the above reaction mixture while controlling the temperature below 5° C. After addition, the mixture was reacted for about half an hour while controlling the temperature around 0° C. in an ice bath. The LCMS check indicated reaction completion and methanol (30 mL) was added and stirred for 10 min and then poured into water (100 mL) and partitioned. The water phase was extracted with dichloromethane/methanol=3/1(100 mL). The organic phase was combined, dired over anhydrous sodium sulfate and rotary evaporated. Dichloromethane (100 mL) was added to the residue to form crystals which was filtered and the filter cake was washed with dichloromethane and dried under vacuum to give 6-fluoro-1-methyl-1H-benzo [d]imidazol-2(3H)-one as a pink solid (4.2 g, yield: 84.0%). The characterization data of this compound were: LCMS (ESI): m/z 167 [M+H]$^+$.

Step. 42c: Preparation of 1-(2-chloropyrimidin-4-yl)-5-fluoro-3-methyl-1H-benzo[d]imidazol-2(3H)-one (Intermediate 503-50): 6-Fluoro-1-methyl-1H-benzo[d]imidazol-2(3H)-one (7.0 g, 42.2 mmol, 1.0 eq) and 2,4-dichloropyrimidine (9.4 g, 63.3 mmol, 1.5 eq) were dissolved in DMF (200 mL) and to it was added Cesium carbonate (20.7 g, 63.3 mmol, 1.5 eq). The mixture was reacted for 4 hours while controlling the temperature below 20° C. with an ice bath and then poured into water (600 mL), stirred for 30 minutes (cooled to the room temperature) and filtered. The residue was washed with water, petroleum ether (200 mL) and methanol (200 mL). The solid was collected and slurried in petroleum ether/ethyl acetate=2/1 (150 mL) with heat. After cooling to room temperature, the crystals were completely precipitated out and filtered. The filter cake was washed with petroleum ether/ethyl acetate=2/1 and dried to give 1-(2-chloropyrimidin-4-yl)-5-fluoro-3-methyl-1H-benzo[d]imidazol-2(3H)-one as a white soli (10.1 g, yield: 86.3%). The characterization data of this compound were: LCMS (ESI): m/z 279 [M+H]$^+$.

Step 42d: Preparation of 1-(2-((4-((2-(dimethylamino)ethyl)(methyl)amino)-2-methoxy-5-nitrophenyl)amino)pyrimidin-4-yl)-5-fluoro-3-methyl-1H-benzo[d]imidazol-2(3H)-one (Intermediate 505-A-50): 1-(2-Chloropyrimidin-4-yl)-5-fluoro-3-methyl-1H-benzo[d]imidazol-2(3H)-one (503-50) (10 g, 35.9 mmol, 1.0 eq) and 4-fluoro-2-methoxy-5-nitroaniline (103) (7.3 g, 39.5 mmol, 1.1 eq) were dissolved in isopropanol (400 mL) and to it was added concentrated hydrochloric acid (8 mL) dropwise. The mixture was heated to 85° C. and reacted for 48 hours. The LCMS check indicated reaction completion and the reaction was cooled to room temperature and water (100 mL) was added. The pH was adjusted to >8 by the addition of a sodium hydroxide aqueous solution (2 mol/L) and stirred for 10 minutes and filtered. The filter cake was washed with methanol and ethyl acetate, dried in vacuum to give the product 1-(2-(4-fluoro-2-methoxy-5-nitroanilino)pyrimidin-4-yl)-1H-benzo[d]imidazol-2(3H)-one as a light yellow solid (12.0 g, yield: 77.9%). The characterization data of this compound were: LCMS (ESI): m/z 429 [M+H]$^+$. The compound obtained above (6.5 g, 15.2 mmol, 1.0 eq), N,N,N-trimethylethylenediamine (3.1 g, 30.4 mmol, 2.0 eq) and N,N-diisopropylethylamine (5.9 g, 45.6 mmol, 3.0 eq) were dissolved in tetrahydrofuran (100 mL), and then N-methylpyrrolidone (20 mL) was added. The reaction system was heated to reflux and stirred to react for 18 hours and then cooled to room temperature and added ethyl acetate (100 mL), which was then washed with water and saturated brine, dried over anhydrous magnesium sulfate. The solvent was rotary evaporated to give a crude product as a yellow solid. The crude product was slurried in methanol and filtered. The filter cake was washed with methanol to give 1-(2-((4-((2-(dimethylamino)ethyl)(methyl)amino)-2-methoxy-5-nitrophenyl)amino)pyrimidin-4-yl)-5-fluoro-3-methyl-1H-benzo[d]imidazol-2(3H)-one as a yellow solid (7.0 g, yield: 90.9%). The characterization data of this compound were: LCMS (ESI): m/z 511 [M+H]$^+$.

Step. 42e: Preparation of 1-(2-((5-amino-4-((2-(dimethylamino)ethyl)(methyl)amino)-2-methoxyphenyl)amino)pyrimidin-4-yl)-5-fluoro-3-methyl-1H-benzo[d]imidazol-2(3H)-one (Intermediate 506-A-50): 1-(2-((4-((2-(dimethylamino)ethyl)(methyl)amino)-2-methoxy-5-nitrophenyl)amino)pyrimidin-4-yl)-5-fluoro-3-methyl-1H-benzo[d]imidazol-2(3H)-one (505-A-50) (7.0 g, 13.7 mmol, 1.0 eq), iron powder (3.8 g, 68.5 mmol, 5.0 eq), ammonium chloride (3.7 g, 68.5 mmol, 5.0 eq) and water (20 mL) were dissolved in ethanol (100 mL) and heated to 85° C. to react for 3 hours. The LCMS check indicated reaction completion and 1-(2-((5-amino-4-((2-(dimethylamino)ethyl)(methyl)amino)-2-methoxyphenyl)amino)pyrimidin-4-yl)-5-fluoro-3-methyl-1H-benzo[d]imidazol-2(3H)-one was obtained. The characterization data of this compound were: LCMS (ESI): m/z 481 [M+H]$^+$.

Step. 42f: Preparation of N-(2-((2-(dimethylamino)ethyl)(methyl) amino)-5-((4-(5-fluoro-3-methyl-2-oxo-2,3-dihydro-1H-benzo[d]imidazol-1-yl)pyrimidin-2-yl)amino)-4-methoxyphenyl)acrylamide (Compound 50): Method 1: The reaction solution of 1-(2-(5-amino-4-((2-dimethylamino ethyl)(methyl)amino)-2-methoxyanilino)pyrimidin-4-yl) 5-fluoro-3-methyl-1H-benzo[d]imidazol-2(3H)-one (506-A-50) obtained above was cooled to about 0° C. with an ice salt bath, and then 3-chloropropionyl chloride (3.5 g, 27.4 mmol, 2.0 eq) in tetrahydrofuran (20 mL) was added dropwise. After addition, the reaction was stirred for 30 minutes while controlling the temperature around 0° C. The LCMS check indicated reaction was not completed and N—N-diisopropylethylamine (5.3 g, 41.1 mmol, 3.0 eq) was added. After stirring for 10 minutes, additional 3-chloropropionyl chloride (3.5 g, 27.4 mmol, 2.0 eq) in tetrahydrofuran (20 mL) was added. After addition, the reaction was stirred for about 30 minutes while controlling the temperature around 0° C. The LCMS check indicated reaction completion and water (200 mL) and dichloromethane (200 mL) was then added, stirred for 10 minutes and then filtered on celite in bush funnel. The filtrate was partitioned and the water phase was extracted with dichloromethane (100 mL). The organic phases were combined and rotary evaporated to give an off white residue which was slurried in ethyl acetate (100 mL), filtered and washed with ethyl acetate to give a white intermediate. The intermediate was dissolved in acetonitrile (100 mL), and then triethylamine (10 mL) was added and the reaction was refluxed for 18 hours. The LCMS check indicated reaction completion. The reaction was cooled to room temperature and water (100 mL) was added, and stirred for 1 hour to allow the solid to precipitate out completely and filtered. The filter cake was washed with water and petroleum ether. The filter cake was dissolved in dichloromethane (50 mL), dried over anhydrous sodium sulfate, filtered and the solvent was rotary evaporated to give the product N-(2-((2-(dimethylamino)ethyl)(methyl)amino)-5-((4-(5-fluoro-3-methyl-2-oxo-2,3-dihydro-1H-benzo[d]imidazol-1-yl)pyrimidin-2-yl)amino)-4-methoxyphenyl)acrylamide as a white solid (4.7 g, yield: 75.1%). Method 2: 1-(2-(5-Amino-4-(2-dimethylaminoethyl)(methyl)amino)-2-methoxyanilino)5-fluoro-3-methyl-1H-benzo[d]imidazol-2(3H)-one (506-A-50) (100 mg, 0.21 mmol, 1 eq), 2-(7-azobenzotriazole)-N, N, N', N'-tetramethyluronium hexafluorophosphate (103 mg, 0.27 mmol, 1.3 eq) and triethylamine (64 mg, 0.63 mmol, 3 eq) were dissolved in dichloromethane (20 mL). To the mixture was added acrylic acid (18 mg, 0.252 mmol, 1.2 eq.) in dichloromethane (10 mL) dropwise slowly. After stirring for 2 hours, the reaction mixture was concentrated and purified by silica gel column chromatography (eluent: dichloromethane/methanol=100:1) to give N-(2-((2-(dimethylamino)ethyl)(methyl) amino)-5-((4-(5-fluoro-3-methyl-2-oxo-2,3-dihydro-1H-benzo[d]imidazol-1-yl)pyrimidin-2-yl)amino)-4-methoxyphenyl)acrylamide as a white solid (80 mg, yield: 71.4%).

The characterization data of Compound 50 were: LCMS (ESI): m/z 535 [M+H]$^+$. m.p.: 208-210° C.; $^1$H NMR (500 MHz, DMSO-d$_6$) δ 10.01 (s, 1H), 8.72 (s, 1H), 8.42 (m, 2H), 8.11 (s, 1H), 7.66 (d, J=5.6 Hz, 1H), 7.20 (dd, J=8.9, 2.6 Hz, 1H), 7.04 (s, 1H), 6.65 (t, J=8.2 Hz, 1H), 6.40 (dd, J=16.9, 10.2 Hz, 1H), 6.18 (dd, J=17.0, 1.9 Hz, 1H), 5.72 (dd, J=10.2, 1.7 Hz, 1H), 3.75 (d, J=4.4 Hz, 3H), 3.34 (d, J=8.6 Hz, 3H), 2.91 (t, J=5.9 Hz, 2H), 2.75 (s, 3H), 2.34 (dd, J=11.2, 5.4 Hz, 2H), 2.20 (s, 6H).

Example 43: Preparation of N-(2-((2-(dimethylamino) ethyl)(methyl)amino)-4-methoxy-5-(4-(3-(3-methylbut-2-enyl)-2-oxo-2,3-dihydro-1H-benzo[d] imidazol-1-yl)pyrimidin-2-ylamino)phenyl) acrylamide (Compound 62) (Prepared According to Scheme 7)

The synthetic method was similar to that described in Example 24, except that 1-(2-(5-amino-4-((2-(dimethylamino)ethyl)(methyl)amino)-2-methoxyphenylamino)pyrimidin-4-yl)-5chloro-3-methyl-1H-benzo[d]imidazol-2(3H)-one (506-A-51) therein was replaced by 1-(2-(5-amino-4-((2-(dimethylamino)ethyl)(methyl)amino)-2-methoxyphenyl amino)pyrimidin-4-yl)-3-(3-methylbut-2-enyl)-1H-benzo[d]imidazol-2(3H)-one (506-A-62) (110 mg, 0.2 mmol, 1.0 eq). N-(2-((2-(Dimethylamino)ethyl)(methyl)amino)-4-methoxy-5-(4-(3-(3-methylbut-2-enyl)-2-oxo-2,3-dihydro-1H-benzo[d]imidazol-1-yl)pyrimidin-2-ylamino)phenyl)acrylamide was obtained as a beige solid (60 mg, yield: 49%).

The characterization data of Compound 62 were: LCMS (ESI): m/z 571 [M+H]$^+$. m.p.: 187-188° C.; $^1$H NMR (500 MHz, DMSO-d$_6$) δ 10.03 (s, 1H), 8.70 (s, 1H), 8.42 (d, J=5.5 Hz, 2H), 8.10 (s, 1H), 7.67 (d, J=5.4 Hz, 1H), 7.13 (d, J=10.0 Hz, 2H), 7.04 (s, 1H), 6.88 (s, 1H), 6.39 (dd, J=16.8, 10.2 Hz, 1H), 6.18 (d, J=16.8 Hz, 1H), 5.72 (d, J=10.1 Hz, 1H), 5.24 (s, 1H), 4.47 (d, J=6.2 Hz, 2H), 3.75 (s, 3H), 2.90 (s, 2H), 2.74 (s, 3H), 2.37 (d, J=28.5 Hz, 2H), 2.21 (s, 6H), 1.80 (d, J=20.1 Hz, 3H), 1.68 (s, 3H).

Example 44: Preparation of N-(5-((4-(3-(cyclopropylmethyl)-2-oxo-2,3-dihydro-1H-benzo[d]imidazol-1-yl)pyrimidin-2-yl)amino)-2-((2-(dimethylamino)ethyl)(methyl)amino)-4-methoxyphenyl) acrylamide (Compound 63) (Prepared According to Scheme 7)

The synthetic method was similar to that described in Example 24, except that 1-(2-(5-amino-4-((2-(dimethylamino)ethyl)(methyl)amino)-2-methoxyphenylamino)pyrimidin-4-yl)-5chloro-3-methyl-1H-benzo[d]imidazol-2(3H)-one (506-A-51) therein was replaced by 1-(2-((5-amino-4-((2-(dimethylamino)ethyl)(methyl)amino)-2-methoxyphenyl)amino)pyrimidin-4-yl)-3-(cyclopropylmethyl)-1H-benzo[d]imidazol-2 (3H)-one (506-A-63) (529 mg, 1.05 mmol, 1.0 eq). N-(5-((4-(3-(cyclopropylmethyl)-2-oxo-2,3-dihydro-1H-benzo[d]imidazol-1-yl)pyrimidin-2-yl)amino)-2-((2-(dimethylamino)ethyl)(methyl)amino)-4-methoxyphenyl)acrylamide was obtained as a cream colored solid (300 mg, yield: 51.4%).

The characterization data of Compound 63 were: LCMS (ESI): m/z 557 [M+H]$^+$. m.p.: 68-72° C.; $^1$H NMR (500 MHz, DMSO-d$_6$) δ 10.04 (s, 1H), 8.70 (s, 1H), 8.43 (d, J=5.6 Hz, 2H), 8.10 (d, J=7.1 Hz, 1H), 7.67 (d, J=5.6 Hz, 1H), 7.30 (d, J=7.9 Hz, 1H), 7.15 (t, J=7.7 Hz, 1H), 7.05 (s, 1H), 6.89 (t, J=7.8 Hz, 1H), 6.39 (dd, J=16.9, 10.2 Hz, 1H), 6.18 (d, J=16.9 Hz, 1H), 5.72 (d, J=10.3 Hz, 1H), 3.77 (m, 5H), 2.91 (t, J=5.5 Hz, 2H), 2.75 (s, 3H), 2.34 (s, 2H), 2.21 (s, 6H), 0.47 (m, 2H), 0.40 (m, 2H).

Example 45: Preparation of (E)-N-(5-(4-(1H-indol-1-yl)pyrimidin-2-ylamino)-2-((2-(dimethylamino)ethyl)(methyl)amino)-4-methylphenyl)-4-methoxybut-2-enamide (Compound 71) (Prepared According to Scheme 6)

N$^4$-(4-(1H-indol-1-yl)pyrimidin-2-yl)-N$^1$-(2-(dimethylamino)ethyl)-5-methoxy-N$^1$-methylbenzene-1,2,4-triamine (403-1) (200 mg, 0.464 mmol, 1.0 eq) was dissolved in acetonitrile (50 mL) and N,N-diisopropylethylamine (120 mg, 0.928 mmol, 2.0 eq), (E)-4-bromobut-2-enoic acid (602-71) (92 mg, 0.5568 mmol, 1.2 eq) and 2-(7-azobenzotriazole)-N,N,N',N'-tetramethyluronium hexafluorophosphate (211 mg, 0.5568 mmol, 1.2 eq) were added in sequence, and then stirred at room temperature for 4 hours. When the reaction was completed, aqueous sodium carbonate solution was added and extracted with dichloromethane (3×100 mL). The organic layers were combined and concentrated in vacuo. The residue was purified by silica gel column chromatography (eluent: dichloromethane/methanol: 50:1 to 30:1) to give (E)-N-(5-((4-(1H-indol-1-yl)pyrimidin-2-yl)amino)-2-((2-(dimethylamino)ethyl)(methyl)amino)-4-methylphenyl)-4-bromobut-2-enamide as a yellow oil (200 mg, yield: 74.5%). MS (ESI): m/z 578 (M+1)$^+$. The compound obtained above (200 mg, 0.346 mmol, 1.0 eq) was dissolved in methanol (25 mL) and then sodium methoxide (38 mg, 0.692 mmol, 2.0 eq) was added and stirred at room temperature overnight. When the reaction was completed, water was added and extracted with dichloromethane (100 mL×3). The organic layers were combined and concentrated in vacuo. The residue was purified by silica gel column chromatography (eluent: dichloromethane/methanol: 50/1) to give (E)-N-(5-(4-(1H-indol-1-yl)pyrimidin-2-ylamino)-2-((2-(dimethylamino)ethyl)(methyl)amino)-4-methylphenyl)-4-methoxybut-2-enamide as a yellow solid (40 mg, yield: 21%).

The characterization data of Compound 71 were: LCMS (ESI): m/z 530 [M+H]$^+$. m.p.: 193-200° C.; $^1$H NMR (500 MHz, CDCl$_3$) δ 9.51 (s, 1H), 8.48 (d, J=5.6 Hz, 1H), 8.24 (d, J=8.3 Hz, 1H), 8.12 (s, 1H), 7.62 (d, J=7.4 Hz, 2H), 7.28 (m, 3H), 7.21 (t, J=7.2 Hz, 1H), 6.97 (m, 2H), 6.74 (m, 2H), 4.16 (d, J=2.8 Hz, 2H), 3.90 (s, 3H), 3.43 (s, 3H), 3.08 (s, 2H), 2.64 (m, 11H).

Example 46: Preparation of N-(5-(4-(1H-indol-1-yl)pyrimidin-2-ylamino)-4-methoxy-2-(methyl(2-(piperidin-1-yl)ethyl)amino)phenyl)acrylamide (Compound 81) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(4-(1H-indol-1-yl)pyrimidin-2-yl)-5-methoxy-N$^1$-methyl-N$^1$-(2-(piperidin-1-yl)ethyl)benzene-1,2,4-triamine (150 mg, 0.318 mmol, 1.0 eq) (403-B-81). N-(5-((4-(1H-Indol-1-yl)pyrimidin-2-ylamino)-4-methoxy-2-(methyl(2-(piperidin-1-yl)ethyl)amino)phenyl) acrylamide was obtained as a yellow solid (25 mg, yield: 10.3%).

The characterization data of Compound 81 were: LCMS (ESI): m/z 526 [M+H]$^+$; m.p.: 131-136° C.; $^1$H NMR (500 MHz, DMSO-d$_6$) δ 9.38 (s, 1H), 8.57 (s, 1H), 8.39 (m, 3H), 8.12 (d, J=3.7 Hz, 1H), 7.58 (d, J=7.2 Hz, 1H), 7.12 (m, 3H), 7.00 (s, 1H), 6.76 (d, J=3.6 Hz, 1H), 6.59 (dd, J=16.8, 10.2 Hz, 1H), 6.19 (m, 1H), 5.73 (m, 1H), 3.79 (s, 3H), 3.03 (d, J=5.1 Hz, 2H), 2.72 (s, 3H), 2.35 (m, 6H), 1.49 (s, 4H), 1.36 (d, J=19.9 Hz, 2H).

Example 47: Preparation of N-(2-((2-(dimethylamino)ethyl)(methyl) amino)-5-(4-(5-fluoro-3-isopropyl-2-oxo-2,3-dihydro-1H-benzo[d]imidazol-1-yl)pyrimidin-2-ylamino)-4-methoxyphenyl) acrylamide (Compound 91) (Prepared According to Scheme 7)

Step 47a: Preparation of 5-fluoro-N$^1$-isopropylbenzene-1,2-diamine (Intermediate 501-91): 2,4-Difluoronitrobenzene (10 g, 62.9 mmol, 1.0 eq), isopropylamine (4.8 g, 81.8 mmol, 1.5 eq) and potassium carbonate (17.4 g, 125.8 mmol, 2.0 eq) were dissolved in DMF (150 mL) and reacted at room temperature for 18 hours. The LCMS check indicated reaction completion and the reaction was poured into water (400 mL) and stirred for 30 minutes to allow crystallize to precipitate out completely. The mixture was filtered and the filter cake was wash with water. The filter cake was collected and dried in vacuum to give the product 5-fluoro-N-isopropyl-2-nitroaniline as a yellow solid (11.5 g, yield: 92.4%). The characterization data of this compound were: LCMS (ESI): m/z 199 [M+H]$^+$. The compound obtained above (6.1 g, 62.9 mmol, 1.0 eq), iron powder (8.6 g, 154 mmol, 5.0 eq), ammonium chloride (8.2 g, 154 mmol, 3.0 eq) and water (20 mL) were dissolved in ethanol (100 mL). Under nitrogen protection condition, the reaction was heated to 85° C. and reacted for 3 hours. The LCMS check indicated reaction completion. The reaction solution temperature was lowered to room temperature, and the reaction solution was poured into water (200 mL) and then dichloromethane was added (200 mL). The mixture was stirred for 5 minutes and filtered through celite and the filtrate was partitioned. The organic phase was dried over anhydrous sodium sulfate and the solvent was rotary evaporated to give the product 5-fluoro-N$^1$-isopropylbenzene-1,2-diamine as a red oil (11.5 g, yield: 92.4%). The characterization data of this compound were: LCMS (ESI): m/z 169 [M+H]$^+$.

Step 47b: Preparation of 6-fluoro-1-isopropyl-1H-benzo[d]imidazol-2(3H)-one (Intermediate 502-91): 5-Fluoro-N$^1$-isopropylbenzene-1,2-diamine (501-91) (4.5 g, 26.8 mmol, 1.0 eq) was dissolved in dichloromethane (100 mL) and triethylamine (5.5 g, 53.6 mmol, 2.0 eq) was added. Under nitrogen protection, the reaction temperature was lowered to about 0° C. in an ice bath. Triphosgene (2.8 g, 9.38 mmol, 0.35 eq) in dichloromethane (50 mL) was added dropwise to the above reaction mixture with the control of temperature below 5° C. After addition, the mixture was reacted for about half an hour while controlling the temperature around 0° C. in an ice bath. The LCMS check indicated reaction completion and methanol (30 mL) was added and stirred for 10 minutes to quench the reaction. The reaction mixture was washed with water and saturated brine, dried over anhydrous magnesium sulfate and rotary evaporated to give the product 6-fluoro-1-isopropyl-1H-benzo[d]imidazol-2(3H)-one as a brown solid (4.6 g, yield: 88.5%). The characterization data of this compound were: LCMS (ESI): m/z 195 [M+H]$^+$.

Step 47c: Preparation of 1-(2-chloropyrimidin-4-yl)-5-fluoro-3-isopropyl-1H-benzo[d]imidazol-2 (3H)-one (Intermediate 503-91): 6-Fluoro-1-isopropyl-1H-benzo [d]imidazol-2(3H)-one (502-91) (4.6 g, 23.7 mmol, 1.0 eq) and 2,4-dichloropyrimidine (5.3 g, 35.6 mmol, 1.5 eq) were dissolved in DMF (80 mL) and cesium carbonate (11.6 g, 35.6 mmol, 1.5 eq) was then added and the mixture was reacted at room temperature overnight. The reaction was poured into water (100 mL) and stirred for 30 minutes (cooled to room temperature), filtered and the residue was washed with water and petroleum ether (200 mL). The solid was collected and slurried in methanol (100 mL), filtered and the filter cake was washed with methanol. The solid was collected and dried in vaccum to give the product 1-(2-chloropyrimidin-4-yl)-5-fluoro-3-isopropyl-1H-benzo[d]imidazol-2(3H)-one as a pink solid (6.1 g, yield: 83.6%). The characterization data of this compound were: LCMS (ESI): m/z 307 [M+H]$^+$.

Step 47d: Preparation of 1-(2-((4-((2-(dimethylamino) ethyl)(methyl)amino)-2-methoxy-5-nitrophenyl)amino)pyrimidin-4-yl)-5-fluoro-3-isopropyl-1H-benzo[d]imidazol-2 (3H)-one (Intermediate 505-A-91): 1-(2-Chloropyrimidin-4-yl)-5-fluoro-3-isopropyl-1H-benzo[d]imidazol-2(3H)-one (503-91) (2.8 g, 9.13 mmol, 1.0 eq) and 4-Fluoro-2-methoxy-5-nitroaniline (103) (1.87 g, 10.0 mmol, 1.1 eq) were dissolved in isopropyl alcohol (100 mL) and concentrated hydrochloric acid (2.0 mL) was then added dropwise and heated to 85° C. to react for 18 hours. The LCMS check indicated reaction completion and the reaction temperature was lowered to room temperature and filtration was performed. The filter cake was washed with petroleum ether (100 mL). The solid was collected and dried in vacuum to give the product 1-(2-((4-fluoro-2-methoxy-5-nitrophenyl) amino)pyrimidin-4-yl)-5-fluoro-3-isopropyl-1H-benzo[d] imidazol-2(3H)-one as a earthy yellow solid (3.4 g, yield: 81.0%). The characterization data of this compound were: LCMS (ESI): m/z 457 [M+H]$^+$. The compound obtained above (3.4 g, 7.46 mmol, 1.0 eq), N,N,N-trimethylethylenediamine (1.5 g, 14.92 mmol, 2.0 eq) and N,N-diisopropylethylamine (2.9 g, 22.38 mmol, 3.0 eq) were dissolved in tetrahydrofuran (80 mL). The reaction system was heated to reflux to react for 18 hours. The reaction temperature was lowered to room temperature and then ethyl acetate (100 mL) was added, which was then washed with water and saturated brine, dried over anhydrous magnesium sulfate and rotary evaporated to give 1-(2-((4-((2-(dimethylamino) ethyl)(methyl)amino)-2-methoxy-5-nitrophenyl)amino)pyrimidin-4-yl)-5-fluoro-3-isopropyl-1H-benzo[d]imidazol-2 (3H)-one as a yellow solid (3.7 g, yield: 92.5%). The characterization data of this compound were: LCMS (ESI): m/z 539 [M+H]$^+$.

Step 47e: Preparation of 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2 (3H)-one (Intermediate 506-A-91): 1-(2-((4-((2-(Dimethylamino)ethyl)(methyl)amino)-2-methoxy-5-nitrophenyl)amino)pyrimidin-4-yl)-5-fluoro-3-isopropyl-1H-benzo[d]imidazol-2(3H)-one (505-A-91) (3.7 g, 6.88 mmol, 1.0 eq), iron powder (1.9 g, 34.4 mmol, 5.0 eq), ammonium chloride (1.8 g, 34.4 mmol, 3.0 eq) and water (12 mL) were dissolved in ethanol (60 mL) and heated to 85° C. to react for 3 hours. The LCMS check indicated reaction completion to give 1-(2-((5-amino-4-((2-(dimethylamino) ethyl)(methyl)amino)-2-methoxyphenyl)amino)pyrimidin-4-yl)-5-fluoro-3-isopropyl-1H-benzo[d]imidazol-2(3H)-one (11.5 g, yield: 92.4%). The characterization data of this compound were: LCMS (ESI): m/z 509 [M+H]$^+$.

Step 47f: Preparation of N-(2-((2-(dimethylamino)ethyl) (methyl)amino)-5-(4-(5-fluoro-3-isopropyl-2-oxo-2,3-dihydro-1H-benzo[d]imidazol-1-yl)pyrimidin-2-ylamino)-4-methoxyphenyl)acrylamide (Compound 91):

Method 1: The reaction solution of 1-(2-((5-amino-4-((2-(dimethylamino)ethyl)(methyl)amino)-2-methoxyphenyl) amino)pyrimidin-4-yl)-5-fluoro-3-isopropyl-1H-benzo[d] imidazol-2 (3H)-one (506-A-91) obtained above was cooled to about 0° C. with an ice-salt bath and to it 3-Chloropropionyl chloride (1.8 g, 13.76 mmol, 2.0 eq) in tetrahydrofuran (10 mL) was added dropwise. After addition, the reaction was stirred for 30 minutes while controlling the temperature around 0° C. The LCMS check indicated reaction completion and to the reaction water (100 mL) and dichloromethane (100 mL) was added and stirred for 10 minutes, filtered through celite in bush funnel and the filtrate was partitioned. The water phase was extracted with dichloromethane (50 mL). The organic phase was combined and the solvent was rotary evaporated to give a milk white residue which was slurried in ethyl acetate (50 mL), filtered and washed with ethyl acetate to give a white intermediate. The intermediate was dissolved in acetonitrile (50 mL), and then triethylamine (10 mL) was added and refluxed to react for 18 hours. The LCMS check indicated reaction completion. The temperature was lowered to room temperature and the mixture was poured into water (300 mL) and stirred for 1 hour to allow the solid to precipitate out completely and then filtered. The filter cake was washed with water and dissolved in dichloromethane (50 mL) which was washed with saturated brine, dried over anhydrous sodium sulfate and rotary evaporated to give the product N-(2-((2-(dimethylamino)ethyl) (methyl)amino)-5-(4-(5-fluoro-3-isopropyl-2-oxo-2,3-dihydro-1H-benzo[d]imidazol-1-yl)pyrimidin-2-ylamino)-4-methoxyphenyl) acrylamide as a white solid (2.9 g, yield: 75.1%). Method 2: 1-(2-((5-Amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) (400 mg, 0.787 mmol, 1.0 eq) was dissolved in dichloromethane (50 mL) and triethylamine (0.328 mL, 2.36 mmol, 3.0 eq) was then added. The mixture temperature was lowered to −70° C. and a solution of 3-chloropropionyl chloride (601-1) (109 mg, 1.18 mmol, 1.5 eq) in dichloromethane (10 mL) was added dropwise. The mixture was reacted for 15 minutes and then quenched with methanol, extracted with dichloromethane which was then dried over anhydrous sodium sulfate and concentrated in vacuo. The residue was purified by silica gel column chromatography (eluent: dichloromethane/methanol=400/1 to 150/1) to give N-(2-((2-(dimethylamino)ethyl) (methyl)amino)-5-(4-(5-fluoro-3-isopropyl-2-oxo-2,3-dihydro-1H-benzo[d]imidazol-1-yl)pyrimidin-2-ylamino)-4-methoxyphenyl)acrylamide as a white solid (224 mg, yield: 50%).

The characterization data of Compound 91 were: LCMS (ESI): m/z 563 [M+H]+. m.p.: 225-227° C.; 1H NMR (500 MHz, DMSO-d6) δ 10.01 (s, 1H), 8.70 (s, 1H), 8.41 (m, 2H), 8.11 (s, 1H), 7.62 (d, J=5.6 Hz, 1H), 7.32 (d, J=9.3 Hz, 1H), 7.04 (s, 1H), 6.65 (t, J=8.9 Hz, 1H), 6.40 (dd, J=16.9, 10.2 Hz, 1H), 6.18 (d, J=16.8 Hz, 1H), 5.72 (d, J=10.3 Hz, 1H), 4.64 (m, 1H), 3.76 (s, 3H), 2.90 (d, J=5.2 Hz, 2H), 2.74 (s, 3H), 2.34 (s, 2H), 2.20 (s, 6H), 1.47 (d, J=6.9 Hz, 6H).

Example 48: Preparation of N-(5-(4-(3-cyclopropyl-5-fluoro-2-oxo-2,3-dihydrobenzo[d]imidazol-1-yl)pyrimidin-2-ylamino)-2-((2-(dimethylamino)ethyl)(methyl)amino)-4-methoxyphenyl)acrylamide (Compound 98) (Prepared According to Scheme 7)

The synthetic method was similar to method 2 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((5-amino-4-((2-(dimethylamino)ethyl) (methyl)amino)-2-methoxyphenylamino)pyrimidin-4-yl)-3-cyclopropyl-5-fluoro-1H-benzo[d]imidazol-2(3H)-one (868 mg, 1.72 mmol, 1.0 eq) (506-A-98). N-(5-(4-(3-Cyclopropyl-5-fluoro-2-oxo-2,3-dihydrobenzo[d]imidazol-1-yl)pyrimidin-2-ylamino)-2-((2-(dimethylamino)ethyl)(methyl)amino)-4-methoxyphenyl)acrylamide was obtained as a yellow solid (300 mg, yield: 31.1%).

The characterization data of Compound 98 were: LCMS (ESI): m/z 561 [M+H]+. m.p.: 181-184° C.; 1H NMR (500 MHz, DMSO-d6) δ 10.01 (s, 1H), 8.69 (s, 1H), 8.41 (m, 2H), 8.08 (s, 1H), 7.62 (d, J=5.6 Hz, 1H), 7.11 (dd, J=8.8, 2.6 Hz, 1H), 7.04 (s, 1H), 6.66 (t, J=8.4 Hz, 1H), 6.40 (dd, J=16.9, 10.2 Hz, 1H), 6.18 (dd, J=16.9, 1.8 Hz, 1H), 5.73 (dd, J=14.6, 4.4 Hz, 1H), 3.75 (s, 3H), 2.91 (t, J=5.2 Hz, 3H), 2.74 (s, 3H), 2.34 (s, 2H), 2.20 (s, 6H), 1.07 (m, 2H), 0.93 (m, 2H).

Example 49: Preparation of N-(5-((4-(5-chloro-3-cyclopropyl-2-oxo-2,3-dihydro-1H-benzo[d]imidazol-1-yl)pyrimidin-2-yl)amino)-2-((2-(dimethylamino)ethyl)(methyl)amino)-4-methoxyphenyl) acrylamide (Compound 99) (Prepared According to Scheme 7)

The synthetic method was similar to method 2 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((5-amino-4-((2-(dimethylamino)ethyl)(methyl)amino)-2-methoxyphenyl)amino)pyrimidin-4-yl)-5-chloro-3-cyclopropyl-1,3-dihydro-2H-benzo[d]imidazol-2-one (160 mg, 0.31 mmol) (506-A-99). N-(5-((4-(5-Chloro-3-cyclopropyl-2-oxo-2,3-dihydro-1H-benzo[d]imidazol-1-yl)pyrimidin-2-yl)amino)-2-((2-(dimethylamino)ethyl)(methyl)amino)-4-methoxyphenyl)acrylamide was obtained as a yellow solid (40 mg, yield: 23%).

The characterization data of Compound 99 were: LCMS (ESI): m/z 577 [M+H]+. m.p.: 124-126° C.; 1H NMR (500 MHz, DMSO-d6) δ 10.03 (s, 1H), 8.70 (s, 1H), 8.42 (m, 2H), 8.04 (s, 1H), 7.60 (d, J=5.2 Hz, 1H), 7.26 (s, 1H), 7.05 (s, 1H), 6.87 (d, J=8.1 Hz, 1H), 6.39 (dd, J=16.6, 10.3 Hz, 1H), 6.18 (d, J=16.8 Hz, 1H), 5.72 (d, J=9.9 Hz, 1H), 3.75 (s, 3H), 2.91 (s, 3H), 2.74 (s, 3H), 2.34 (s, 2H), 2.21 (s, 6H), 1.07 (d, J=5.5 Hz, 2H), 0.93 (s, 2H).

Example 50: Preparation of N-(5-((4-(5-cyano-3-cyclopropyl-2-oxo-2,3-dihydro-1H-benzo[d]imidazol-1-yl)pyrimidin-2-yl)amino)-2-((2-(dimethylamino)ethyl)(methyl)amino)-4-methoxyphenyl) acrylamide (Compound 101) (Prepared According to Scheme 7)

The synthetic method was similar to method 2 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((5-amino-4-((2-(dimethylamino)ethyl)(methyl)amino)-2-methoxyphenyl)amino)pyrimidin-4-yl)-3-cyclopropyl-2-oxo-2,3-dihydro-1H-benzo[d]imidazole-5-carbonitrile (506-A-101) (200 mg, 0.39 mmol, 1.0 eq). N-(5-((4-(5-Cyano-3-cyclopropyl-2-oxo-2,3-dihydro-1H-benzo[d]imidazol-1-yl)pyrimidin-2-yl)amino)-2-((2-(dimethylamino)ethyl)(methyl)amino)-4-methoxyphenyl)acrylamide was obtained as a light yellow solid (130 mg, yield: 56%).

The characterization data of Compound 101 were: LCMS (ESI): m/z 568 [M+H]+. m.p.: 177-179° C.; 1H NMR (500 MHz, DMSO-d6) δ 9.92 (s, 1H), 8.77 (s, 1H), 8.47 (d, J=5.5 Hz, 1H), 8.30 (s, 1H), 8.21 (s, 1H), 7.68 (s, 1H), 7.57 (d, J=5.5 Hz, 1H), 7.35 (d, J=7.2 Hz, 1H), 7.03 (s, 1H), 6.56 (s, 1H), 6.19 (d, J=16.8 Hz, 1H), 5.72 (d, J=10.3 Hz, 1H), 3.78 (s, 3H), 2.97 (m, 3H), 2.65 (m, 5H), 2.36 (s, 6H), 1.09 (d, J=5.8 Hz, 2H), 0.95 (s, 2H).

Example 51: Preparation of N-(5-((4-(3-cyclopropyl-5-methoxy-2-oxo-2,3-dihydro-1H-benzo[d]imidazol-1-yl)pyrimidin-2-yl)amino)-2-((2-(dimethylamino)ethyl)(methyl)amino)-4-methoxyphenyl) acrylamide (Compound 102) (Prepared According to Scheme 7)

The synthetic method was similar to method 2 of step 47f in EXAMPLE 47, except that 1-(2-((5-amino-4-((2-(dimethylamino)ethyl)(methyl)amino)-2-methoxyphenyl)amino) pyrimidin-4-yl)-5-fluoro-3-isopropyl-1H-benzo[d]imidazol-2(3H)-one (506-A-91) therein was replaced by 1-(2-((5-amino-4-((2-(dimethylamino)ethyl)(methyl)amino)-2-methoxyphenyl)amino)pyrimidin-4-yl)-3-cyclopropyl-5-methoxy-1,3-dihydro-2H-benzo[d]imidazol-2-one (506-A-102) (420 mg, 0.81 mmol, 1.0 eq). N-(5-((4-(3-Cyclopropyl-5-methoxy-2-oxo-2,3-dihydro-1H-benzo[d]imidazol-1-yl)pyrimidin-2-yl)amino)-2-((2-(dimethylamino)ethyl)(methyl)amino)-4-methoxyphenyl)acrylamide was obtained as beige solid (250 mg, yield: 54%).

The characterization data of Compound 102 were: LCMS (ESI): m/z 573 [M+H]$^+$. m.p.: 144-146° C.; $^1$H NMR (500 MHz, DMSO-d$_6$) δ 10.04 (s, 1H), 8.63 (s, 1H), 8.39 (m, 2H), 7.96 (d, J=8.5 Hz, 1H), 7.64 (d, J=5.6 Hz, 1H), 7.05 (s, 1H), 6.80 (d, J=2.3 Hz, 1H), 6.39 (m, 2H), 6.18 (dd, J=16.9, 1.4 Hz, 1H), 5.72 (d, J=11.1 Hz, 1H), 3.75 (d, J=7.1 Hz, 6H), 2.89 (m, 3H), 2.75 (s, 3H), 2.34 (t, J=5.7 Hz, 2H), 2.20 (s, 6H), 1.07 (q, J=6.9 Hz, 2H), 0.92 (m, 2H).

Example 52: Preparation of N-(5-(4-(3-(cyclopropylmethyl)-5-fluoro-2-oxo-2,3-dihydro-1H-benzo[d]imidazol-1-yl)pyrimidin-2-ylamino)-2-((2-(dimethylamino)ethyl)(methyl)amino)-4-methoxyphenyl) acrylamide (Compound 105) (Prepared According to Scheme 7)

The synthetic method was similar to method 2 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-(5-amino-4-((2-(dimethylamino)ethyl)(methyl)amino)-2-methoxyphenylamino)pyrimidin-4-yl)-3-(cyclopropylmethyl)-5-fluoro-1H-benzo[d]imidazol-2(3H)-one (506-A-105) (520 mg, 1.0 mmol, 1.0 eq). N-(5-(4-(3-(Cyclopropylmethyl)-5-fluoro-2-oxo-2,3-dihydro-1H-benzo[d]imidazol-1-yl)pyrimidin-2-ylamino)-2-((2-(dimethylamino)ethyl)(methyl)amino)-4-methoxyphenyl) acrylamide was obtained as a beige solid (180 mg, yield: 31%).

The characterization data of Compound 105 were: LCMS (ESI): m/z 563 [M+H]$^+$. m.p.: 168-169° C.; $^1$H NMR (500 MHz, DMSO-d$_6$) δ 10.02 (s, 1H), 8.72 (s, 1H), 8.42 (m, 2H), 8.11 (s, 1H), 7.65 (d, J=4.9 Hz, 1H), 7.31 (d, J=7.8 Hz, 1H), 7.05 (s, 1H), 6.66 (s, 1H), 6.40 (dd, J=16.3, 10.2 Hz, 1H), 6.18 (d, J=16.9 Hz, 1H), 5.72 (d, J=9.6 Hz, 1H), 3.76 (s, 5H), 2.91 (s, 2H), 2.75 (s, 3H), 2.34 (s, 2H), 2.20 (s, 6H), 1.23 (s, 1H), 0.45 (m, 4H).

Example 53: Preparation of N-(2-((2-(dimethylamino)ethyl) (methyl)amino)-4-methyl-5-((4-(3-methyl-2-oxo-2,3-dihydro-1H-benzo[d]imidazol-1-yl)pyrimidin-2-yl)amino)phenyl)acrylamide (Compound 118) (Prepared According to Scheme 7)

The synthetic method was similar to method 2 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-(5-amino-4-((2-(dimethylamino)ethyl)(methyl)amino)-2-methylphenyl amino)pyrimidin-4-yl)-3-methyl-1,3-dihydro-2H-benzo[d]imidazol-2-one (506-A-118) (72 mg, 0.16 mmol, 1.0 eq). N-(2-((2-(Dimethylamino)ethyl) (methyl)amino)-4-methyl-5-((4-(3-methyl-2-oxo-2,3-dihydro-1H-benzo[d]imidazol-1-yl)pyrimidin-2-yl)amino)phenyl)acrylamide was obtained as a white solid (15 mg, yield: 18.7%).

The characterization data of Compound 118 were: LCMS (ESI): m/z 501 [M+H]$^+$. m.p.: 208-210° C.; $^1$H NMR (500 MHz, DMSO-d$_6$) δ 10.11 (s, 1H), 9.06 (s, 1H), 8.42 (d, J=5.6 Hz, 1H), 8.33 (s, 1H), 7.96 (s, 1H), 7.69 (d, J=5.6 Hz, 1H), 7.16 (m, 3H), 6.80 (d, J=7.0 Hz, 1H), 6.40 (dd, J=16.8, 10.3 Hz, 1H), 6.20 (d, J=16.9 Hz, 1H), 5.74 (d, J=11.2 Hz, 1H), 3.35 (s, 3H), 2.87 (s, 2H), 2.72 (s, 3H), 2.36 (s, 2H), 2.18 (m, 9H).

Example 54: Preparation of N-{2-[(2-dimethyl-amino-ethyl)-methyl-amino]-4-(2-methoxy-ethoxy)-5-[4-(3-methyl-2-oxo-2,3-dihydro-benzoimidazol-1-yl)-pyrimidin-2-ylamino]-phenyl}-acrylamide (Compound 120) (Prepared According to Scheme 7)

The synthetic method was similar to that described in Example 24, except that 1-(2-(5-amino-4-((2-(dimethylamino)ethyl)(methyl)amino)-2-methoxyphenylamino)pyrimidin-4-yl)-5chloro-3-methyl-1H-benzo[d]imidazol-2(3H)-one (506-A-51) therein was replaced by 1-{2-[5-Amino-4-[(2-dimethylamino-ethyl)-methyl-amino]-2-(2-methoxy-ethoxy)-phenyl amino]-pyrimidin-4-yl}-3-methyl-1,3-dihydro-benzoimidazol-2-one (506-A-120) (250 mg, 0.49 mmol, 1.0 eq). N-{2-[(2-Dimethylamino-ethyl)-methyl-amino]-4-(2-methoxy-ethoxy)-5-[4-(3-methyl-2-oxo-2,3-dihydro-benzoimidazol-1-yl)-pyrimidin-2-ylamino]-phenyl}-acrylamide (28 mg, yield: 10.2%) was obtained as a white waxy solid.

The characterization data of Compound 120 were: LCMS (ESI): m/z 561 [M+H]$^+$. m.p.: 71-78° C.; $^1$H NMR (500 MHz, DMSO-d$_6$) δ 10.04 (s, 1H), 8.60 (s, 1H), 8.52 (s, 1H), 8.45 (d, J=5.6 Hz, 1H), 8.10 (d, J=7.4 Hz, 1H), 7.71 (d, J=5.6 Hz, 1H), 7.17 (m, 2H), 7.07 (s, 1H), 6.90 (t, J=7.6 Hz, 1H), 6.39 (dd, J=16.9, 10.2 Hz, 1H), 6.18 (dd, J=16.9, 1.8 Hz, 1H), 5.72 (m, 1H), 4.08 (m, 2H), 3.52 (m, 2H), 3.38 (d, J=9.6 Hz, 3H), 3.19 (s, 3H), 2.89 (t, J=5.7 Hz, 2H), 2.72 (s, 3H), 2.33 (s, 2H), 2.21 (s, 6H).

Example 55: Preparation of N-(5-((4-(5-chloro-1H-pyrrolo[3,2-b]pyridin-1-yl) pyrimidin-2-yl)amino)-2-((2-(dimethylamino)ethyl)(methyl)amino)-4-methoxyphenyl)acrylamide (Compound 124) (Prepared According to Scheme 6)

The synthetic method was similar to that described in Example 6, except that N$^4$-(4-(1H-indol-1-yl)-5-(trifluoromethyl)pyrimidin-2-yl)-N$^1$-(2-(dimethylamino)ethyl)-5-methoxy-N$^1$-methylbenzene-1,2,4-triamine (403-A-5) therein was replaced by N$^4$-(4-(5-chloro-1H-pyrrolo[3,2-b]pyridin-1-yl)pyrimidin-2-yl)-N$^1$-(2-(dimethylamino)ethyl)-5-methoxy-N$^1$-methylbenzene-1,2,4-triamine (200 mg, 0.43 mmol, 1.0 eq). N-(5-((4-(5-Chloro-1H-pyrrolo[3,2-b]pyridin-1-yl) pyrimidin-2-yl)amino)-2-((2-(dimethylamino) ethyl)(methyl)amino)-4-methoxyphenyl)acrylamide was obtained as a beige solid (140 mg, yield: 63%).

The characterization data of Compound 124 were: LCMS (ESI): m/z 521 [M+H]$^+$. m.p.: 127-129° C.; $^1$H NMR (500 MHz, DMSO) δ 10.12 (s, 1H), 9.03 (s, 1H), 8.37 (d, J=5.6 Hz, 2H), 8.29 (s, 1H), 8.08 (d, J=3.6 Hz, 1H), 7.56 (d, J=7.7 Hz, 1H), 7.24 (s, 1H), 7.10 (m, 2H), 6.98 (t, J=7.5 Hz, 1H), 6.75 (d, J=3.6 Hz, 1H), 6.40 (dd, J=16.9, 10.2 Hz, 1H), 6.19

(dd, J=16.9, 1.7 Hz, 1H), 5.74 (dd, J=10.2, 1.6 Hz, 1H), 2.89 (t, J=5.3 Hz, 2H), 2.74 (s, 3H), 2.36 (s, 2H), 2.20 (d, J=23.4 Hz, 9H).

Example 56: Preparation of N-(2-((2-(dimethylamino)ethyl)(methyl)amino)-5-((4-(3-methyl-2-oxo-2,3-dihydro-1H-benzo[d]imidazol-1-yl)pyrimidin-2-yl)amino)phenyl)acrylamide (Compound 125) (Prepared According to Scheme 7)

The synthetic method was similar to method 2 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((3-amino-4-((2-(dimethylamino)ethyl)(methyl)amino)phenyl)amino) pyrimidin-4-yl)-3-methyl-1,3-dihydro-2H-benzo[d]imidazol-2-one (506-A-125) (110 mg, 0.26 mmol, 1.0 eq). N-(2-((2-(Dimethylamino)ethyl)(methyl)amino)-5-((4-(3-methyl-2-oxo-2,3-dihydro-1H-benzo[d]imidazol-1-yl)pyrimidin-2-yl)amino)phenyl)acrylamide was obtained as a white solid (50 mg, 0.1 mmol, yield: 38.5%).

The characterization data of Compound 125 were: LCMS (ESI): m/z 487 [M+H]$^+$. m.p.: 190-193° C.; $^1$H NMR (500 MHz, DMSO-d$_6$) δ 10.18 (s, 1H), 9.63 (s, 1H), 8.51 (dd, J=17.1, 9.4 Hz, 3H), 7.76 (d, J=5.6 Hz, 1H), 7.53 (d, J=8.2 Hz, 1H), 7.25 (m, 3H), 7.07 (t, J=7.0 Hz, 1H), 6.40 (dd, J=16.9, 10.1 Hz, 1H), 6.24 (d, J=16.8 Hz, 1H), 5.77 (d, J=10.2 Hz, 1H), 3.39 (s, 3H), 2.84 (t, J=5.5 Hz, 2H), 2.66 (d, J=23.7 Hz, 3H), 2.29 (t, J=5.1 Hz, 2H), 2.22 (d, J=12.1 Hz, 6H).

Example 57: Preparation of N-(2-((2-(dimethylamino)ethyl)(methyl)amino)-5-((4-(3-isopropyl-2-oxo-2,3-dihydro-1H-benzo[d]imidazol-1-yl)pyrimidin-2-yl)amino)-4-methylphenyl)acrylamide (Compound 127) (Prepared According to Scheme 7)

The synthetic method was similar to method 1 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((5-amino-4-((2-(dimethylamino)ethyl)(methyl)amino)-2-methylphenyl)amino)pyrimidin-4-yl)-3-isopropyl-1,3-dihydro-2H-benzo[d]imidazol-2-one (506-A-127) (360 mg, 0.77 mmol, 1.0 eq). N-(2-((2-(Dimethylamino)ethyl)(methyl)amino)-5-((4-(3-isopropyl-2-oxo-2,3-dihydro-1H-benzo[d]imidazol-1-yl)pyrimidin-2-yl)amino)-4-methylphenyl)acryl amide was obtained as a white solid (15 mg, yield: 8%).

The characterization data of Compound 127 were: LCMS (ESI): m/z 529 [M+H]$^+$. m.p.: 179-181° C.; $^1$H NMR (500 MHz, DMSO-d6) δ 10.12 (s, 1H), 9.04 (s, 1H), 8.38 (d, J=43.5 Hz, 2H), 7.97 (s, 1H), 7.65 (s, 1H), 7.33 (d, J=6.6 Hz, 1H), 7.23 (s, 1H), 7.09 (s, 1H), 6.77 (s, 1H), 6.40 (m, 1H), 6.20 (d, J=16.5 Hz, 1H), 5.74 (d, J=8.9 Hz, 1H), 4.66 (s, 1H), 2.86 (s, 2H), 2.72 (s, 3H), 2.34 (s, 2H), 2.18 (d, J=32.8 Hz, 9H), 1.47 (d, J=5.0 Hz, 6H).

Example 58: Preparation of N-(2-((2-(dimethylamino)ethyl)(methyl)amino)-5-((4-(3-isopropyl-2-oxo-2,3-dihydro-1H-benzo[d]imidazol-1-yl)pyrimidin-2-yl)amino)phenyl)acrylamide (Compound 128) (Prepared According to Scheme 7)

The synthetic method was similar to method 1 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((4-((2-(dimethylamino)ethyl)(methyl)amino)-3-aminophenyl)amino)pyrimidin-4-yl)-3-isopropyl-1H-benzo[d]imidazol-2(3H)-one (506-A-128) (650 mg, 1.33 mmol, 1.0 eq). N-(2-((2-(Dimethylamino)ethyl)(methyl)amino)-5-((4-(3-isopropyl-2-oxo-2,3-dihydro-1H-benzo[d]imidazol-1-yl)pyrimidin-2-yl)amino)phenyl)acrylamide was obtained as a white solid (390 mg, yield: 54%).

The characterization data of Compound 128 were: LCMS (ESI): m/z 515 [M+H]$^+$; m.p.: 85-90° C.; $^1$H NMR (500 MHz, DMSO-d6) δ 10.19 (s, 1H), 9.62 (s, 1H), 8.51 (dd, J=16.1, 5.7 Hz, 3H), 7.73 (d, J=5.6 Hz, 1H), 7.53 (dd, J=8.6, 1.7 Hz, 1H), 7.40 (d, J=7.9 Hz, 1H), 7.27 (d, J=8.7 Hz, 1H), 7.19 (t, J=7.7 Hz, 1H), 7.05 (t, J=7.8 Hz, 1H), 6.40 (dd, J=16.9, 10.1 Hz, 1H), 6.25 (dd, J=16.9, 1.8 Hz, 1H), 5.77 (m, 1H), 4.71 (dd, J=13.9, 7.0 Hz, 1H), 2.83 (t, J=5.6 Hz, 2H), 2.68 (s, 3H), 2.29 (t, J=5.6 Hz, 2H), 2.20 (s, 6H), 1.51 (d, J=6.9 Hz, 6H).

Example 59: Preparation of N-(2-((2-(dimethylamino)ethyl)(methyl)amino)-4-isopropyl-5-((4-(3-methyl-2-oxo-2,3-dihydro-1H-benzo[d]imidazol-1-yl)pyrimidin-2-yl)amino)phenyl)acrylamide (Compound 132) (Prepared According to Scheme 7)

The synthetic method was similar to method 1 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((4-((2-(dimethylamino)ethyl)(methyl)amino)-2-isopropyl-5-aminophenyl)amino)pyrimidin-4-yl)-3-methyl-1,3-dihydro-2H-benzo[d]imidazol-2-one (506-A-132) (500 mg, 0.99 mmol, 1.0 eq). N-(2-((2-(Dimethylamino)ethyl)(methyl)amino)-4-isopropyl-5-((4-(3-methyl-2-oxo-2,3-dihydro-1H-benzo[d]imidazol-1-yl)pyrimidin-2-yl)amino)phenyl)acryl amide was obtained as a yellow solid (73 mg, yield: 16%).

The characterization data of Compound 132 were: LCMS (ESI): m/z 529 [M+H]$^+$; $^1$H NMR (500 MHz, DMSO-d6) δ 10.08 (s, 1H), 9.02 (s, 1H), 8.40 (d, J=5.6 Hz, 1H), 8.24 (s, 1H), 7.83 (s, 1H), 7.66 (d, J=5.6 Hz, 1H), 7.28 (s, 1H), 7.13 (m, 2H), 6.73 (s, 1H), 6.40 (dd, J=16.9, 10.2 Hz, 1H), 6.19 (dd, J=16.9, 1.7 Hz, 1H), 5.73 (d, J=11.6 Hz, 1H), 3.34 (s, 3H), 3.13 (dt, J=13.7, 6.8 Hz, 1H), 2.92 (dd, J=23.6, 18.3 Hz, 2H), 2.76 (s, 3H), 2.37 (s, 2H), 2.21 (s, 6H), 1.09 (t, J=9.4 Hz, 6H).

Example 60: Preparation of N-(2-((2-(dimethylamino)ethyl) (methyl)amino)-5-((4-(3-isopropyl-2-oxo-2,3-dihydro-1H-benzo[d]imidazol-1-yl)-5-methoxypyrimidin-2-yl)amino)-4-methoxyphenyl)acrylamide (Compound 133) (Prepared According to Scheme 7)

The synthetic method was similar to method 1 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((4-((2-(dimethylamino)ethyl)(methyl)amino)-2-methoxy-5-aminophenyl)amino)-5-methoxypyrimidin-4-yl)-3-isopropyl-1H-benzo[d]imidazol-2(3H)-one (506-A-133) (660 mg, 1.2 mmol, 1.0 eq). N-(2-((2-(Dimethylamino) ethyl) (methyl)amino)-5-((4-(3-isopropyl-2-oxo-2,3-dihydro-1H-benzo[d]imidazol-1-yl)-5-methoxypyrimidin-2-yl)amino)-4-methoxyphenyl)acrylamide was obtained as a white solid (310 mg, yield: 42.7%).

The characterization data of Compound 133 were: LCMS (ESI): m/z 575 [M+H]$^+$. m.p.: 92-95° C.; $^1$H NMR (500 MHz, DMSO-d6) δ 10.00 (s, 1H), 8.65 (s, 1H), 8.58 (s, 1H), 8.20 (s, 1H), 7.36 (d, J=7.9 Hz, 1H), 7.03 (m, 4H), 6.30 (ddd, J=18.4, 17.0, 5.8 Hz, 1H), 5.74 (d, J=11.4 Hz, 1H), 4.64 (m, 1H), 3.81 (d, J=6.0 Hz, 6H), 2.83 (t, J=5.7 Hz, 2H), 2.68 (s, 3H), 2.27 (t, J=5.7 Hz, 2H), 2.18 (s, 6H), 1.49 (d, J=6.9 Hz, 6H).

Example 61: Preparation of N-(5-((5-(dimethylamino)-4-(3-isopropyl-2-oxo-2,3-dihydro-1H-benzo[d]imidazol-1-yl)pyrimidin-2-yl)amino)-2-((2-(dimethylamino)ethyl)(methyl)amino)-4-methoxyphenyl)acrylamide (Compound 135) (Prepared According to Scheme 7)

The synthetic method was similar to method 1 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((5-amino-4-((2-(dimethylamino)ethyl)(methyl)amino)-2-methoxyphenyl) amino)-5-(dimethylamino)pyrimidin-4-yl)-3-isopropyl-1,3-dihydro-2H-benzo[d]imidazol-2-one. N-(5-((5-(Dimethylamino)-4-(3-isopropyl-2-oxo-2,3-dihydro-1H-benzo[d]imidazol-1-yl)pyrimidin-2-yl)amino)-2-((2-(dimethylamino)ethyl)(methyl)amino)-4-methoxyphenyl)acrylamide was obtained as a white solid (90 mg, yield: 13.9%).

The characterization data of Compound 135 were: LCMS (ESI): m/z 588 [M+H]$^+$. m.p.: 114.6-116.2° C.; $^1$H NMR (500 MHz, DMSO) δ 10.15 (s, 1H), 9.69 (s, 1H), 8.48 (s, 1H), 8.41 (s, 1H), 8.10 (s, 1H), 7.36 (d, J=7.9 Hz, 1H), 7.07 (t, J=7.7 Hz, 1H), 6.98 (t, J=7.6 Hz, 1H), 6.88 (d, J=6.3 Hz, 2H), 6.22 (d, J=16.9 Hz, 1H), 5.69 (d, J=10.6 Hz, 1H), 4.63 (dt, J=13.8, 6.9 Hz, 1H), 3.82 (s, 3H), 3.15 (d, J=63.2 Hz, 4H), 2.71 (d, J=42.9 Hz, 6H), 2.55 (s, 3H), 2.50 (s, 6H), 1.47 (d, J=6.9 Hz, 6H).

Example 62: Preparation of N-(2-((2-(dimethylamino) ethyl)(methyl)amino)-5-((4-(3-isopropyl-5-methoxy-2-oxo-2,3-dihydro-1H-benzo[d]imidazol-1-yl)pyrimidin-2-yl)amino)-4-methoxyphenyl)acrylamide (Compound 138) (Prepared According to Scheme 7)

The synthetic method was similar to method 1 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((4-((2-(dimethylamino)ethyl)(methyl) amino)-2-methoxy-5-aminophenyl)amino)pyrimidin-4-yl)-3-isopropyl-5-methoxy-1H-benzo[d]imidazol-2(3H)-one (506-A-138) (1.3 g, 2.36 mmol, 1.0 eq). N-(2-((2-(Dimethylamino)ethyl)(methyl)amino)-5-((4-(3-isopropyl-5-methoxy-2-oxo-2,3-dihydro-1H-benzo[d]imidazol-1-yl)pyrimidin-2-yl)amino)-4-methoxyphenyl)acrylamide was obtained as a white solid (940 mg, yield: 65.7%).

The characterization data of Compound 138 were: LCMS (ESI): m/z 575 [M+H]$^+$; m.p.: 95-98° C.; $^1$H NMR (500 MHz, DMSO-d6) δ 10.04 (s, 1H), 8.63 (s, 1H), 8.40 (m, 2H), 8.00 (d, J=8.5 Hz, 1H), 7.66 (d, J=5.7 Hz, 1H), 7.05 (s, 1H), 6.90 (d, J=2.4 Hz, 1H), 6.40 (m, 2H), 6.19 (dd, J=17.0, 1.8 Hz, 1H), 5.73 (dd, J=14.4, 4.3 Hz, 1H), 4.64 (m, 1H), 3.75 (s, 6H), 2.91 (t, J=5.7 Hz, 2H), 2.75 (s, 3H), 2.34 (t, J=5.6 Hz, 2H), 2.20 (s, 6H), 1.47 (d, J=6.9 Hz, 6H).

Example 63: Preparation of N-(2-((2-(dimethylamino) ethyl)(methyl)amino)-5-((4-(5-hydroxy-3-isopropyl-2-oxo-2,3-dihydro-1H-benzo[d]imidazol-1-yl)pyrimidin-2-yl)amino)-4-methoxyphenyl) acrylamide (Compound 139) (Prepared According to Scheme 7)

The synthetic method was similar to method 1 of step 47f in EXAMPLE 47, except that 1-(2-((5-amino-4-((2-(dimethylamino)ethyl)(methyl)amino)-2-methoxyphenyl)amino)pyrimidin-4-yl)-5-fluoro-3-isopropyl-1H-benzo[d]imidazol-2(3H)-one (506-A-91) therein was replaced by 1-(2-((4-((2-(dimethylamino)ethyl)(methyl)amino)-2-methoxy-5-aminophenyl)amino)pyrimidin-4-yl)-5-hydroxy-3-isopropyl-1H-benzo[d]imidazol-2(3H)-one (35 mg, 0.065 mmol, 1.0 eq). N-(2-((2-(Dimethylamino)ethyl)(methyl) amino)-5-((4-(5-hydroxy-3-isopropyl-2-oxo-2,3-dihydro-1H-benzo[d]imidazol-1-yl)pyrimidin-2-yl)amino)-4-methoxyphenyl)acrylamide was obtained as a white solid (20 mg, yield: 54.8%).

The characterization data of Compound 139 were: LCMS (ESI): m/z 561 [M+H]$^+$; m.p.: 115-117° C.; $^1$H NMR (500 MHz, DMSO) δ 10.06 (s, 1H), 9.35 (s, 1H), 8.62 (s, 1H), 8.38 (d, J=15.4 Hz, 2H), 7.89 (s, 1H), 7.66 (s, 1H), 7.03 (s, 1H), 6.69 (s, 1H), 6.26 (dd, J=67.7, 30.1 Hz, 3H), 5.73 (s, 1H), 4.58 (s, 1H), 3.74 (s, 3H), 2.90 (s, 2H), 2.75 (s, 3H), 2.34 (s, 2H), 2.18 (d, J=26.7 Hz, 6H), 1.45 (s, 6H).

Experimental Examples

I. Enzyme Activity Inhibition Assay
1. Assay Methods
(1) Mutant EGFR T790M/L858R Activity Inhibition Assay The activity of Mutant EGFR T790M/L858R protein kinase was tested by Caliper mobility shift assay (see J Biomol Screen 14:31, 2009).

The assay procedure is as follows. The object compound was dissolved in DMSO, and then diluted by a kinase buffer (50 mM HEPES-pH7.5, 0.0015% Brij-35, 10 mM MgCl$_2$, 2 mM DTT). 5 μl of the compound dissolved in 10% DMSO at a concentration of 5-fold of the final reaction concentration was added to a 384 well plate. 5 μl of 10% DMSO was used in a no-compound control well, while 5 μl of a kinase buffer was used in a no-enzyme activity control well. 10μ of 2.5-fold diluted EGFR T790M L858R (Invitrogen, Cat. No PR8911A, Lot. 1498821A) enzyme solution was added, followed by incubation at room temperature for 10 minutes. Then 10 μl of a 2.5-fold diluted substrate solution of Peptide FAM-P22 (GL Biochem, Cat. No. 112393, Lot. No. P130408-ZB112393) was further added. After 60 minutes of incubation at 28° C., the reaction was stopped by adding 25 μl of a stop solution (100 mM HEPES, pH 7.5, 0.015% Brij-35, 0.2% Coating Reagent #3). The conversion rate was read on Caliper EZ Reader II (Caliper Life Sciences). The conversion rate was then converted to inhibitory rate.

As used herein, "max" refers to the conversion rate of the DMSO no-compound control well, and "min" refers to the conversion rate of the no-enzyme activity control well. A curve was obtained by plotting the inhibitory rate as a function of the compound concentration. The XLFit excel add-in version 4.3.1 software was used to fit the curve and calculate the IC50. Inhibitory rate %=(max−conversion rate)/(max−min)×100.

(2) Mutant EGFR T790M Activity Inhibition Assay

The activity of Mutant EGFR T790M protein kinase was tested by Caliper mobility shift assay (see J Biomol Screen 14:31, 2009).

The assay procedure is as follows. The object compound was dissolved in DMSO, and then diluted by a kinase buffer (50 mM HEPES-pH7.5, 0.0015% Brij-35, 10 mM $MgCl_2$, 2 mM DTT). 5 μl of the compound dissolved in 10% DMSO at a concentration of 5-fold of the final reaction concentration was added to a 384 well plate. 5 μl of 10% DMSO was used in a no-compound control well, while 5 μl of a kinase buffer was used in a no-enzyme activity control well. 10μ of 2.5-fold diluted mutant EGFR T790M (Invitrogen, Cat. No PR8052A, Lot. 1229180E) enzyme solution was added, followed by incubation at room temperature for 10 minutes. Then 10 μl of a 2.5-fold diluted substrate solution of Peptide FAM-P22 (GL Biochem, Cat. No. 112393, Lot. No. P130408-ZB112393) was further added. After 60 minutes of incubation at 28° C., the reaction was stopped by adding 25 μl of a stop solution (100 mM HEPES, pH 7.5, 0.015% Brij-35, 0.2% Coating Reagent #3). The conversion rate was read on Caliper EZ Reader II (Caliper Life Sciences). The conversion rate was then converted to inhibitory rate.

As used herein, "max" refers to the conversion rate of the DMSO no-compound control well, and "min" refers to the conversion rate of the no-enzyme activity control well. A curve was obtained by plotting the inhibitory rate as a function of the compound concentration. The XLFit excel add-in version 4.3.1 software was used to fit the curve and calculate the IC50. Inhibitory rate %=(max−conversion rate)/(max−min)×100.

2. Assay Results

The median inhibitory concentration ($IC_{50}$) of each compound in the above assay was calculated. The assay results are shown in Table 1 below.

TABLE 1

Results of enzyme activity inhibition ($IC_{50}$)

| Compound | EGFR T790M/L858R | EGFR T790M | Compound | EGFR T790M/L858R | EGFR T790M |
|---|---|---|---|---|---|
| 5 | IV | | 6 | IV | |
| 8 | V | | 10 | IV | |
| 11 | IV | | 20 | V | |
| 27 | V | | 28 | V | |
| 29 | V | | 30 | V | |
| 31 | V | | 33 | V | |
| 34 | IV | | 36 | V | |
| 37 | V | | 38 | V | |
| 39 | V | | 41 | V | |
| 46 | IV | | 50 | V | |
| 51 | V | | 52 | V | |
| 53 | V | | 57 | IV | |
| 62 | V | | 63 | V | |
| 66 | III | | 67 | II | |
| 68 | III | | 69 | V | |
| 70 | IV | | 71 | IV | |
| 73 | IV | | 74 | IV | |
| 77 | IV | | 78 | IV | |
| 79 | V | | 80 | IV | |
| 81 | IV | | 82 | IV | |
| 84 | III | | 91 | V | |
| 98 | V | | 99 | IV | |
| 101 | V | | 102 | V | |
| 105 | V | | 118 | V | |
| 120 | IV | | 124 | V | |
| 125 | V | | 127 | V | |

TABLE 1-continued

Results of enzyme activity inhibition ($IC_{50}$)

| Compound | EGFR T790M/L858R | EGFR T790M | Compound | EGFR T790M/L858R | EGFR T790M |
|---|---|---|---|---|---|
| 128 | V | | 132 | IV | |
| 133 | IV | | 135 | IV | |
| 138 | IV | | 139 | V | |
| AZD9291 | V | V | | | |
| CO-1686 | IV | IV | | | |

As used herein, I>100 nM, 100 nM≥II>50 nM, 50 nM≥III>10 nM, 10 nM≥IV>1 nM, V≤1 nM.

As can be seen from the above table, these compounds can selectively inhibit the mutant T790M EGFR, including single-point mutation T790M and double-point mutation (such as T790M/L858R).

II. Inhibition assay on tumor cell proliferation

1. Assay Methods

By using a CellTiter-Glo luminescence cell viability test kit (Promega, # G7572), the content of adenosine triphosphate (ATP) was determined to assess the cell viability.

Human non-small-cell lung cancer tumor cell line H1975 carries L858R and T790M epidermal growth factor receptor (EGFR) double mutation. Human colon cancer cell line LOVO and human non-small-cell lung cancer H358 express wild-type EGFR. Human non-small-cell lung cancer cell line HCC827 carries deletion mutation in exon 19 (ex19del). Those cell lines are purchased from Shanghai Fudan IBS Cell Resource Center and American Tissue Culture Collection (ATCC).

The assay procedure is as follows. The cells in a cell culture plate were digested with a pancreatic enzyme, re-suspended in a DPBS culture medium, and had the cell density counted by Scepter automated cytometer (Millipore # PHCC00000). The cells were diluted to a solution of 44,000 cells per ml. The cell solution with adjusted density was added to the cell assay plate at 90 microliters per well. The plate was placed in an incubator with 5% $CO_2$ at 37° C. for 24 hours of incubation, and then added with different concentrations of subject compounds. The cells were incubated for 72 hours with the compounds in presence of 10% bovine serum. The content of ATP was determined by a CellTiter-Glo® Luminescent Cell Viability Assay kit (see the manufacturer's instruction for details) to evaluate cell-growth inhibition.

Briefly, 30 μl of CellTiter-Glo® reagent was added to each well, and then shaken for 10 minutes to induce cell lysis. The fluorescent signal was detected and recorded by Fluoroskan Ascent FL (Thermo). The max signal value was obtained from the cells treated by dimethyl sulfoxide for 72 hours. The min signal value was obtained from the medium alone (the number of the cells was 0). Inhibitory rate %=(max signal value−compound signal value)/(max signal value−min signal value)×100. The data was processed by GraphPad Prism V5.0 software (GraphPad Software, San Diego, Calif.). Sigmoidal dose-response curve fitting was performed to calculate the $IC_{50}$ value.

2. Assay Results

The $IC_{50}$ of each compound in the above assay was calculated. The assay results are as shown in Table 2 below.

TABLE 2

Results (IC$_{50}$) of inhibition assay on tumor cell proliferation

| Compound | H1975 | HCC827 | LOVO | H358 |
|---|---|---|---|---|
| 5 | V | | I | II |
| 6 | V | | I | I |
| 8 | V | | I | II |
| 10 | V | | I | II |
| 20 | V | | | II |
| 27 | V | | I | II |
| 28 | V | | I | II |
| 29 | V | | I | II |
| 30 | V | | I | II |
| 31 | V | | | I |
| 33 | V | | I | II |
| 34 | V | | I | II |
| 36 | V | | I | II |
| 37 | V | | I | II |
| 38 | V | | I | II |
| 39 | V | V | I | II |
| 41 | V | | I | II |
| 46 | IV | | I | I |
| 50 | V | | | II |
| 51 | V | | I | II |
| 52 | V | | I | II |
| 53 | IV | | I | III |
| 57 | IV | | I | I |
| 62 | V | | | II |
| 63 | V | | | I |
| 69 | III | | II | II |
| 70 | II | | II | II |
| 73 | III | | I | I |
| 77 | IV | | I | |
| 78 | IV | | I | I |
| 79 | III | | I | I |
| 80 | V | | I | I |
| 82 | III | | | I |
| 91 | V | | | II |
| 98 | V | | | II |
| 99 | V | | | II |
| 101 | V | | | II |
| 102 | V | | | II |
| 105 | V | | | II |
| 118 | V | | | II |
| 124 | V | | | II |
| 125 | V | | | I |
| 127 | V | | | I |
| 128 | V | | | II |
| 132 | V | | | I |
| 133 | V | | | I |
| 135 | IV | | | I |
| 138 | V | | | II |
| 139 | V | | | II |
| AZD9291 | V | V | I | II |
| CO-1686 | IV | II | I | II |

As used herein, I>1 µM, 1 µM≥II>0.1 µM, 0.1 µM≥III>0.05 µM, 0.05 µM≥IV>0.01 µM, V≤0.01 µM. AZD9291 and CO-1686 are positive control drugs.

As can be seen from the above table, these compounds have strong inhibitory activity on cell proliferation of L858R/T790M EGFR mutation cells (such as H1975), and also have strong inhibiting activity on HCC827 with deletion mutation in exon 19. However, these compounds have weak inhibitory activity on cell proliferation of wild-type EGFR cell (such as LOVO and H358), thus having high selectivity.

III. Pharmacokinetic (PK) Experiments

1. Assay Methods

Male SD rats weighing 250-300 g, or male beagles weighing 9-10 kg, were fasted overnight before the experiment. The object compounds were dissolved in 30% sulfobutylated beta-cyclodextrin (SBE-β-CD), and orally administrated to the rats at a dose of 20 mg/kg or to the beagles at a dose of 5 mg/kg. Blood samples were taken at 15 minutes, 30 minutes, 1 hour, 2 hours, 3 hours, 4 hours, 6 hours, 8 hours and 24 hours after administration. 0.3 ml of blood was collected at every time point, placed in a centrifuge tube containing K2-EDTA (ethylenediamine tetraacetic acid dipotassium) and centrifuged (2,000 g, 10 minutes, 4° C.) to collect plasma, which was then stored in an ultra cold storage freezer at −80° C. 50 µL of plasma sample was mixed with 5 µL of internal standard (IS), and then extracted with ethyl acetate. After vacuum drying, the residue was re-dissolved in acetonitrile. The sample was filtered and injected into LC-MS/MS for analysis.

2. Assay Results

The compounds 20, 50, 62, 91 and 124 provided by the present disclosure were well absorbed, with high blood exposure in rats after oral administration. The $T_{max}$ of these compounds was 1.0 to 3.7 hours, the half time ($T_{1/2}$) was 3.0 to 6.8 hours, and the $C_{max}$ was 84.0–349.7 ng/ml (table 3). The $C_{max}$ of compound 50 and compound 90 in beagles after oral administration was 428.0 and 109.2 ng/ml, respectively, with AUC0-24 of 1423.4 and 785.6 hr×ng/ml, respectively (Table 4). As used in the table, $T_{max}$ refers to time to reach peaks, $C_{max}$ refers to maximum blood plasma concentrations, $T_{1/2}$ refers to half-life, $AUC_{0-24}$ refers to area under the concentration-time curve from 0 to 24 hours, and $AUC_{inf}$ refers to area under the concentration-time curve from 0 to infinity.

TABLE 3

Pharmacokinetics in rats after oral administration (20 mg/kg)

| | Compound | | | | |
|---|---|---|---|---|---|
| PK parameter | 20 | 50 | 62 | 91 | 124 |
| $T_{max}$ (hr) | 1.67 | 1.0 | 3.7 | 1.0 | 1.7 |
| $C_{max}$ (ng/ml) | 349.7 | 172.7 | 84.0 | 292.3 | 327.0 |
| $T_{1/2}$ (hr) | 3.7 | 3.1 | 6.8 | 3.0 | 6.1 |
| $AUC_{0-24}$ (hr × ng/mL) | 1437.7 | 561.4 | 834.4 | 1341.5 | 1695.1 |
| $AUC_{inf}$ (hr × ng/mL) | 1449.75 | 597.5 | 920.4 | 1346.0 | 1789.2 |

TABLE 4

Pharmacokinetics in beagles after oral administration (5 mg/kg)

| | Compound | |
|---|---|---|
| PK parameter | 50 | 91 |
| $T_{max}$ (hr) | 1 | 1.67 |
| $C_{max}$ (ng/ml) | 428 | 109.2 |
| $T_{1/2}$ (hr) | 1.45 | 4.37 |
| $AUC_{0-24}$ (hr × ng/mL) | 1423.4 | 785.6 |
| $AUC_{inf}$ (hr × ng/mL) | 1465.2 | 813.5 |

IV. Human H1975 Non-Small-Cell Lung Cancer Tumor Xenograft Mouse Model

Balb/C nude mice were purchased from Beijing Vital River Laboratory Animal Technology Co., Ltd., and housed in SPF animal room. The human non-small-cell lung cancer cell line H1975 in a culture dish was collected by trypsin-EDTA (0.25% trypsin, 1 mM EDTA), and then washed with a serum-free PBS solution. Lastly, the cells were implanted after diluted in a serum-free medium. Only the single cell suspension with a survival rate over 90% (Trypan blue rejection) can be used for injection. 5 million cells suspended in a 0.1 ml serum-free culture were injected into the front right flanking subcutaneous region of each mouse by using a 1 ml syringe and a 25G needle, and the blood vessel was carefully avoided. The tumor size was measured in about one week after implantation. A caliper rule was used to measure the tumor size. The tumor volume was calculated by the following formula: tumor volume=(length×width$^2$)/2.

V. Pharmacokinetic Experiments of Tumor Model

1. Assay Methods

When the volume of H1975 xenograft tumor reached a volume of about 400 mm$^3$, the animals were divided into 6 oral administration groups, that is, excipient control group (0 hour) and groups of 30 minutes, 2 hours, 4 hours, 8 hours, and 24 hours after administration (3 animals at each time point). The compound 91 was dissolved in 30% sulfobutylated beta-cyclodextrin (SBE-β-CD) and 1 N HCl (pH 3-4) at a concentration of 3 mg/ml, and gavage administration at a dose of 30 mg/kg was performed. The mice were euthanized by $CO_2$ at the above time points. Then their blood was collected from the heart and placed in a centrifuge tube containing K2-EDTA, and subjected to plasma collection by centrifugation. The tumor tissue was collected, cooled in liquid nitrogen immediately, and then stored under −80° C. until pharmacokinetic analysis.

Pharmacokinetic analysis was performed as below: the plasma sample and tumor tissue homogenate sample were mixed with 5 microliter of internal standard (IS), and then extracted with ethyl acetate. After vacuum drying, the residue was re-dissolved in acetonitrile. The sample was filtered and injected into LC-MS/MS for analysis.

2. Assay Results

As shown in FIG. 1 and the table below, the compound 91 was absorbed quickly after oral administration. The plasma peak time and the tumor tissue peak time were 0.5 hour and 4 hours, respectively. The $C_{max}$ values were 1723.3 ng/ml and 868.0 ng/ml, respectively. The $AUC_{0-24h}$ (6434.6 ng/ml*hr) of tumor tissue and $AUC_{0-24h}$ (5095.6 ng/ml*hr) of plasma were similar.

TABLE 5

Pharmacokinetic parameters of compound 91 in H1975 xenograft tumor mice after oral administration (30 mg/kg)

| PK parameter | Plasma | Tumor |
|---|---|---|
| $t_{1/2}$ (h) | 3.1 | 5.5 |
| $T_{max}$ (h) | 0.5 | 4.0 |
| $C_{max}$ (ng/ml) | 1723.3 | 868.0 |
| $AUC_{0-24}$ (ng/ml * h) | 5095.6 | 6434.6 |
| $AUC_{0-inf}$ (ng/ml * h) | 5127.6 | 6838.2 |

VI. Pharmacodynamic Experiments of Tumor Model

1. Assay Method

When the H1975 xenograft tumor reached a volume of about 2,000 mm$^3$, the animals were divided into 4 oral administration groups, that is, excipient control group (0 hour) and groups of 2 hours, 4 hours, and 8 hours after administration (3 to 4 animals at each time point). The compound 91 was dissolved in 30% sulfobutylated beta-cyclodextrin (SBE-β-CD) and 1N HCl (pH 3-4) at a concentration of 3 mg/ml. Gavage administration at a dose of 30 mg/kg was performed. The mice were euthanized by $CO_2$ at the above time points. The tumor tissues were collected, immediately cooled in liquid nitrogen, and then stored under −80° C.

20 mg of tumor tissue was homogenized in 300 μl of protein extract (RIPA, CST, #9806). A phosphatase inhibitor (1:100 v/v, Protease Inhibitor Cocktail, sigma, # P8340) and 100 mM/L PMSF (1:100 v/v) were also added to the protein extract. The tissue lysate was centrifuged at 12,000 rpm for 15 minutes at 4° C. Then 200 μl of supernatant was collected and stored at −80° C. The protein concentration was determined by Bradford method (Beyotime, # P0006). After a loading buffer (Beyotime, # P0015L) was added and heated for 5 minutes at 100° C., the protein was separated by 8%-10% SDS-PAGE electrophoresis and transferred to a PVDF membrane. The membrane was blocked with 5% BSA (Beyotime, # ST023) for 60 minutes, added with a β-actin Antibody (CST, #4970), a Mouse Anti-EGFR Antibody (BD, #610017), or a Human Phospho-EGFR/ErbB1 (Y1068) Mouse Antibody (R&D, # MAB3570), incubated overnight at 4° C., and then washed using 1×TBST solution for 3×5 minutes. The membrane was incubated with a fluorescent secondary antibody IRDye@800CW Goat (polyclonal) Anti-Mouse lgG (H+L), Highly Cross Adsorbed (LI-COR, 926-32210) and IRDye@680CW Goat (polyclonal) Anti-Rabbit lgG (H+L), and Highly Cross Adsorbed (LI-COR, #926-68071) at room temperature in dark for 2 hours, and washed again under the same wash condition as described above. Lastly, the membrane was placed in LI-COR Odyssey infrared fluorescent scanning imaging system for imaging and detection.

2. Assay Results

Figure 2:
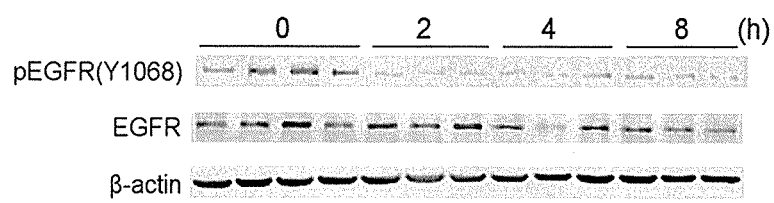
FIG. 2 shows inhibition of EGFR phosphorylation in a T790 mutant H1975 tumor xenograft mice by oral administration of the compound 91, according to an Experimental Example.

As shown in FIG. 2, after oral administration of compound 91 at a dose of 30 mg/kg, the phosphorylation of non-small-cell lung cancer cell line H1975 EGFR with L858R and T790MEGFR double mutation was inhibited. The inhibition effect was strong at 2 hours and 4 hours, and there was still an obvious inhibition effect at 8 hours.

VII. The Potency Assay of Tumor Model

1. Assay Method

This experiment studied the inhibition of tumor growth in H1975 xenograft tumor model by the compounds 20, 50, 91, and 118. When the mean volume of H1975 tumor reached about 260 mm$^3$, the animals were divided into 5 oral administration groups, that is, excipient control group and groups of oral administration of compound 20, compound 50, compound 91, and compound 118, respectively (n=8/group). These compounds were dissolved in 30% sulfobutylated beta-cyclodextrin (SBE-β-CD) and 1N HCl (pH 3-4). Gavage administration at a dose of 10 mg/kg was performed once a day for 16 consecutive days.

Further assay was performed to assess the dose-effect relationship of the inhibition of H1975 transplantation tumor growth by the compounds 51 and 91. The animals were divided in 8 oral administration groups, that is, excipient control group, AZD9291 positive control group (maximum tolerance of 25 mg/kg), and oral administration groups of compounds 50 and 91 at 10 mg/kg, 20 mg/kg and 40 mg/kg, respectively (n=7/group). These compounds were dissolved in 30% sulfobutylated beta-cyclodextrin (SBE-β-CD) and 1N HCl (pH 3-4), respectively. Gavage administration at a dose of 10 mg/kg was performed once a day for 22 consecutive days.

2. Assay Results

Figure 3:
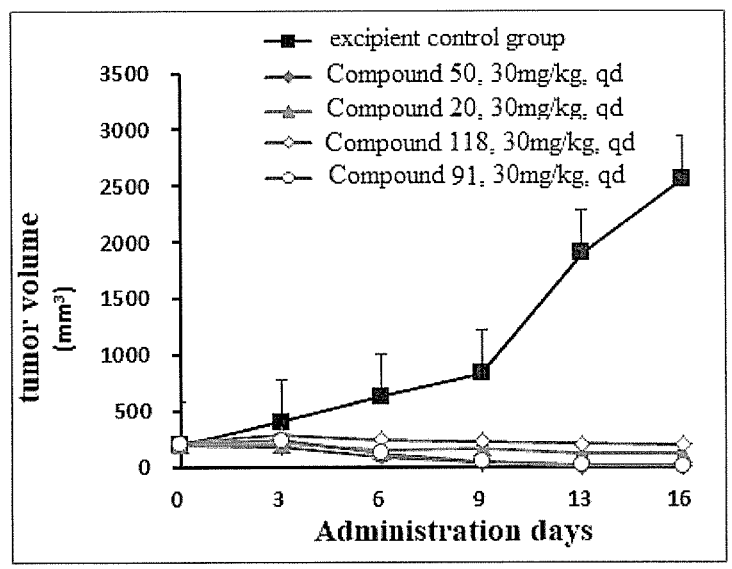
FIG. 3 shows a graph of dose-effect relationship of inhibition of tumor growth (variation in tumor volume) by compounds 20, 50, 91, and 118 in an H1975 xenograft tumor with T790M mutation, according to an Experimental Example.

The experiment was ended for the vehicle control group in 16 days after oral administration due to a tumor volume of larger than 2,000 mm$^3$. As shown in FIG. 3, oral administration of compounds 20, 50, 91, and 118 at a dose of 30 mg/kg qd can inhibit the growth of H1975 xenograft tumor, causing tumor regression. In 16 days after administrating compounds 50 and 91, the tumor substantially disappeared (the T/C values were −97% and −95%, respectively; P<0.001). The weight of each administration group had no significantly loss relative to that before the administration.

Figure 4:
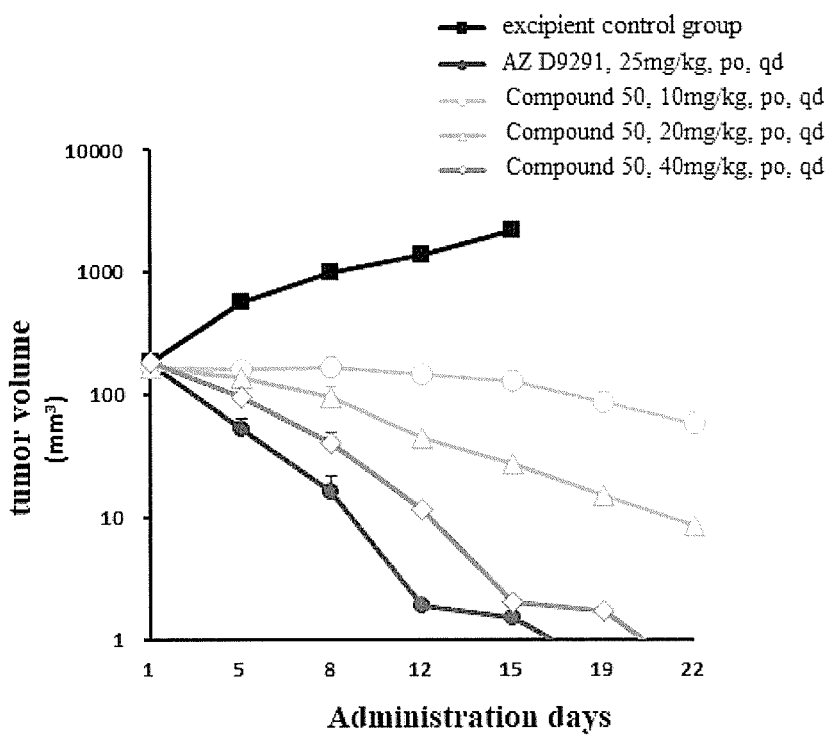
FIG. 4 shows a graph of dose-dependent inhibition of H1975 xenograft tumor with T790M mutation by the compound 50, according to an Experimental Example.
Figure 5:
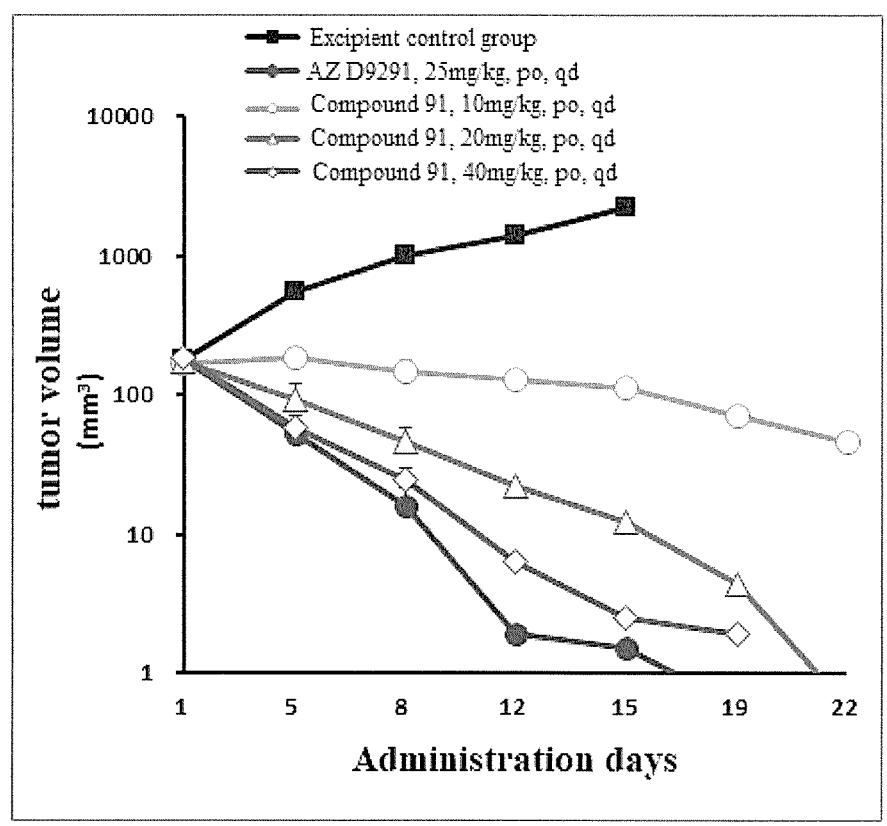
FIG. 5 shows a graph of dose-dependent inhibition of H1975 xenograft tumor with T790M mutation by the compound 91, according to an Experimental Example.

Oral administration of compound 50 and compound 91 dose dependently inhibited the growth of H1975 xenograft tumor. After administration at a high dose (40 mg/kg) of compound 50 and compound 91 for 22 consecutive days, the tumor disappeared completely. A ¼ maximum tolerable dose (10 mg/kg) can still lead to a shrinkage of tumor (the T/C values were −65% and −73%, respectively). Those two compounds had minor effect on weight in each dose group, with the maximum weight loss of less than 5%, as shown in FIGS. 4-5 and the table below.

TABLE 6

Anti-tumor activity and effect on body weight of compound 51 and compound 91 in H1975 xenograft tumor model.

| Administration group | N | T/C value (%) | P value | Weight change (%) |
|---|---|---|---|---|
| Vehicle control group, po, qd | 7 | / | / | 4.2 |
| AZD9291, 25 mg/kg, po, qd | 7 | −100 | <0.001 | −7.2 |
| Compound 50, 10 mg/kg, po, qd | 7 | −65 | <0.001 | 0.0 |
| Compound 50, 20 mg/kg, po, qd | 7 | −95 | <0.001 | −2.0 |
| Compound 50, 40 mg/kg, po, qd | 7 | −100 | <0.001 | −4.4 |
| Compound 91, 10 mg/kg, po, qd | 7 | −73 | <0.001 | 1.6 |
| Compound 91, 20 mg/kg, po, qd | 7 | −100 | <0.001 | 1.2 |
| Compound 91, 40 mg/kg, po, qd | 7 | −100 | <0.001 | −3.5 |

Any feature describe in the above embodiments can be of any combination. For the purpose of brevity, all possible combinations of all features described in the above embodiments are not described. However, all such combinations should be considered as being contained within the scope of the present specification as long as such combinations are not contradictory.

The detailed embodiments described herein are only for the purpose of illustrating the present disclosure, and are not intended to limit the scope of the present disclosure in any way. It would be understood by a person skilled in the art that various changes and modifications can be made to the embodiments described herein without departing from the scope and spirit of the present disclosure. Such changes and modifications are contemplated by the present disclosure, the scope of which should only be defined by the following claims.

The invention claimed is:

1. A 2,4-bis(nitrogen-containing group)-substituted pyrimidine compound of formula III or a pharmaceutically acceptable salt or a stereoisomer thereof:

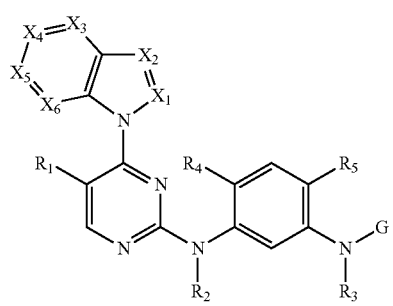

III wherein $R_1$ is selected from the group consisting of H, C1-C6 alkyl, C3-C6 cycloalkyl, C3-C6 cycloalkyl-substituted methyl, halo-substituted C1-C4 alkyl, hydroxyl-substituted C1-C4 alkyl, C1-C3 alkoxy-substituted C1-C4 alkyl, amino-substituted C1-C4 alkyl, C1-C3 alkylamino-substituted C1-C4 alkyl, halogen, nitro, hydroxyl, C1-C6 alkoxy, C1-C6 alkylthio, cyano, amino, C1-C3 alkyl-substituted amino, and carboxyl;

$R_2$ and $R_3$ are each independently selected from the group consisting of H and C1-C6 alkyl;

$R_4$ is selected from the group consisting of H, OH, C1-C6 alkyl, C1-C6 alkoxy, hydroxyl-substituted C1-C4 alkyl, and C1-C3 alkoxy-substituted C1-C4 alkoxy;

$R_5$ is selected from the group consisting of groups below:

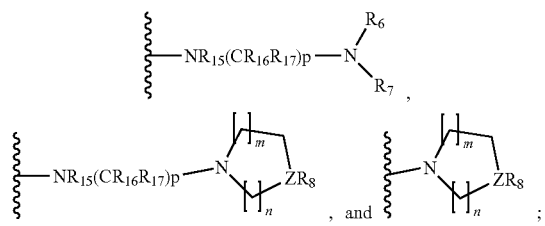

$R_{15}$ is selected from the group consisting of H and C1-C6 alkyl;

$R_{16}$ and $R_{17}$ are each independently selected from the group consisting of H, C1-C6 alkyl, and C1-C6 alkoxy;

Z is selected from the group consisting of C, N, and O, and when Z is O, $R_8$ does not exist;

m is selected from 0, 1, or 2;

n is selected from 1, 2, or 3;

p is selected from 1, 2, 3, 4, 5, or 6;

$R_6$, $R_7$, and $R_8$ are each independently selected from the group consisting of H, C1-C6 alkyl, C3-C6 cycloalkyl, C3-C6 cycloalkyl-substituted methyl, benzyl, phenyl, methylsulfonyl, halo-substituted C1-C4 alkyl, hydroxyl-substituted C1-C4 alkyl, C1-C3 alkoxy-substituted C1-C4 alkyl, amino-substituted C1-C4 alkyl, C1-C3 alkylamino-substituted C1-C4 alkyl, amino, C1-C3 alkyl-substituted amino, hydroxyl, and C1-C6 alkoxy;

$X_1$ is selected from the group consisting of N, and C—$R_9$;

$R_9$ is selected from the group consisting of H, C1-C6 alkyl, halo-substituted C1-C6 alkyl, halogen, cyano, and amino;

$X_2$ is C—$R_{10}$;

$R_{10}$ is selected from the group consisting of H, halogen, C1-C6 alkyl, C2-C6 alkenyl, C2-C6 alkynyl, C3-C6 cycloalkyl, C3-C6 cycloalkyl-substituted methyl, and halo-substituted C1-C6 alkyl;

$X_3$ is N;

$X_4$, $X_5$, and $X_6$ are each independently selected from the group consisting of N, and C—$R_{11}$;

$R_{11}$ is selected from the group consisting of H, C1-C6 alkyl, hydroxyl-substituted C1-C4 alkoxy, C1-C3 alkoxy-substituted C1-C4 alkoxy, C3-C6 cycloalkyl, C3-C6 cycloalkyl-substituted methyl, halo-substituted C1-C4 alkyl, hydroxyl-substituted C1-C4 alkyl, C1-C3 alkoxy-substituted C1-C4 alkyl; amino-substituted C1-C4 alkyl, C1-C3 alkylamino-substituted C1-C4 alkyl, halogen, nitro, hydroxyl, C1-C6 alkoxy, C1-C6 alkylthio, cyano, amino, C1-C3 alkyl-substituted amino, C1-C3 alkyl-substituted amido group, and carboxyl;

G is selected from the group consisting of following groups:

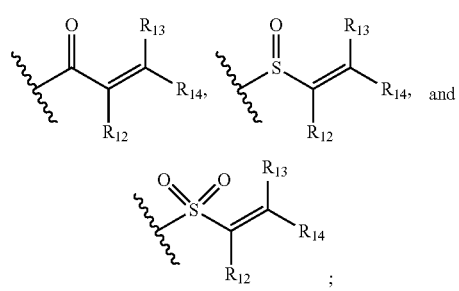

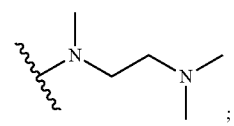

$R_{12}$ and $R_{13}$ are each independently selected from the group consisting of H, and C1-C6 alkyl;

$R_{14}$ is selected from the group consisting of H, C1-C6 alkyl, C1-C3 alkoxy-substituted C1-C4 alkyl, amino-substituted C1-C4 alkyl, C1-C3 alkylamino-substituted C1-C4 alkyl, and heterocycle-substituted C1-C4 alkyl; and if $R_1$ is selected from the group consisting of H, halogen, and cyano, $R_4$ is C1-C6 alkoxy, G is

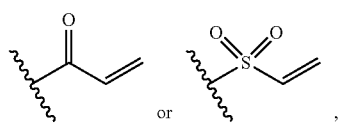

and $R_{11}$ is selected from the group consisting of H, C1-C6 alkyl, C3-C6 cycloalkyl, and halo-substituted C1-C6 alkyl, then $R_{10}$ is not selected from any one in the group consisting of C1-C6 alkyl, C3-C6 cycloalkyl, and halo-substituted C1-C6 alkyl.

2. The 2,4-bis(nitrogen-containing group)-substituted pyrimidine compound or pharmaceutically acceptable salt or stereoisomer thereof according to claim 1, wherein $X_5$ and $X_6$ are each independently selected from the group consisting of N and CH;

$X_4$ is C—$R_{11}$; and $R_{11}$ is defined as in claim 1.

3. The 2,4-bis(nitrogen-containing group)-substituted pyrimidine compound or pharmaceutically acceptable salt or stereoisomer thereof according to claim 1, wherein $X_1$ and $X_2$ are each CH;

$X_4$ is defined as in claim 1;

$X_5$ and $X_6$ are each CH; and $R_1$, $R_2$, $R_3$, $R_4$, $R_5$, and G are each defined as in claim 1.

4. The 2,4-bis(nitrogen-containing group)-substituted pyrimidine compound or pharmaceutically acceptable salt or stereoisomer thereof according to claim 1, wherein $X_1$ and $X_2$ are each CH;

$X_5$ and $X_6$ are each CH;

$X_4$ is C—$R_{11}$;

$R_{11}$ is selected from the group consisting of C1-C6 alkoxy, halogen, and cyano;

$R_1$, $R_2$, and $R_3$ are each H;

$R_4$ is a methoxy group;

$R_5$ is a following group:

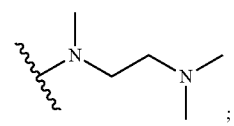

and

G is a following group:

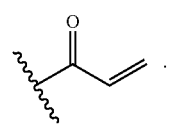 [SMILES: *C(=O)C=C]

5. The 2,4-bis(nitrogen-containing group)-substituted pyrimidine compound or pharmaceutically acceptable salt or stereoisomer thereof according to claim 1, wherein $R_1$ is selected from the group consisting of H, F, Cl, Br, methyl, trifluoromethyl, methoxy, cyano, hydroxyl, and dimethylamino;

$R_2$ and $R_3$ are each H;

$R_4$ is selected from the group consisting of H, methoxy, ethoxy, methyl, ethyl, OH, and methoxyethoxy;

$R_{12}$ and $R_{13}$ are each H; and $R_{14}$ is selected from the group consisting of H, C1-C6 alkyl, C1-C3 alkoxy-substituted C1-C4 alkyl, amino-substituted C1-C4 alkyl, C1-C3 alkylamino-substituted C1-C4 alkyl, and heterocycle-substituted C1-C4 alkyl.

6. The 2,4-bis(nitrogen-containing group)-substituted pyrimidine compound or pharmaceutically acceptable salt or stereoisomer thereof according to claim 1, wherein $R_5$ is selected from the group consisting of following groups:

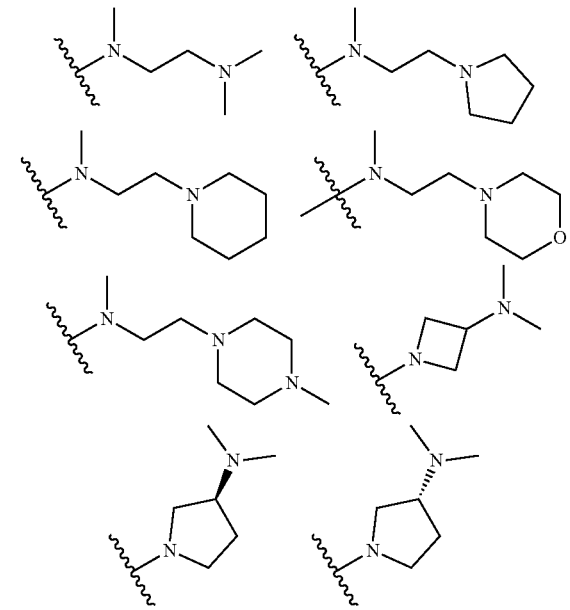

-continued

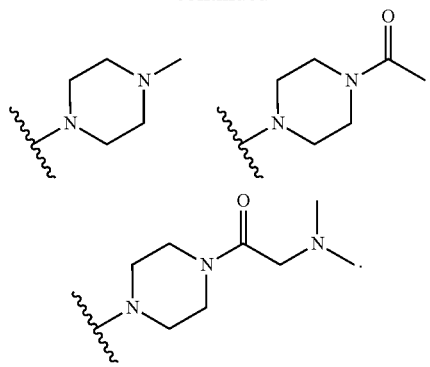

7. The 2,4-bis(nitrogen-containing group)-substituted pyrimidine compound or pharmaceutically acceptable salt or stereoisomer thereof according to claim 1, wherein said compound is selected from the group consisting of following compounds:

compound 20

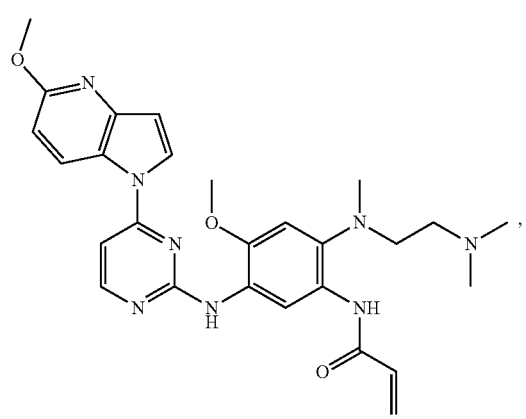

-continued compound 124

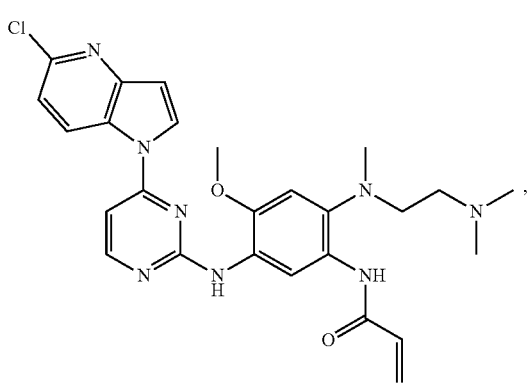

compound 126

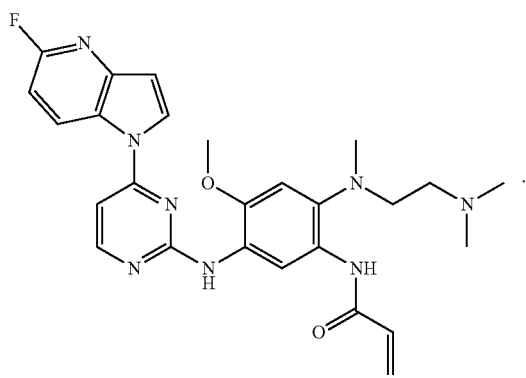

8. A pharmaceutical composition for treatment of a tumor, comprising the 2,4-bis(nitrogen-containing group)-substituted pyrimidine compound or pharmaceutically acceptable salt or stereoisomer thereof according to claim 1 as an active component, and a pharmaceutically acceptable carrier, wherein said tumor is non-small-cell lung cancer with T790M EGFR mutation.

* * * * *